US006440409B1

(12) United States Patent
Milne et al.

(10) Patent No.: US 6,440,409 B1
(45) Date of Patent: Aug. 27, 2002

(54) METHOD FOR EFFICIENT AND HIGHLY SELECTIVE CONTROL OF MICROORGANISMS

(75) Inventors: G. Todd Milne, Brookline; Gerald R. Fink, Chestnut Hill, both of MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/293,549

(22) Filed: Apr. 16, 1999

Related U.S. Application Data

(60) Provisional application No. 60/082,089, filed on Apr. 17, 1998.

(51) Int. Cl.[7] .......................... A61K 48/00; C12N 1/68; C12N 1/14

(52) U.S. Cl. ....................... 424/93.2; 435/6; 435/254.11

(58) Field of Search ............................. 435/6, 254.11; 424/93.2, 93.5

(56) References Cited

U.S. PATENT DOCUMENTS

| | | | | |
|---|---|---|---|---|
| 5,643,745 A | * | 7/1997 | Stuart | ......................... 435/69.1 |
| 5,665,581 A | | 9/1997 | Chen et al. | |
| 5,840,840 A | | 11/1998 | Rybak et al. | |
| 5,866,405 A | | 2/1999 | Choi et al. | |
| 5,882,642 A | | 3/1999 | Choi et al. | |

OTHER PUBLICATIONS

Mattheakis et al. Dph5, a methyltransferase gene required for diphthamide biosynthesis in *Saccharomyces cerevisiae*. Mol. and Cellular Biol. vol. 12(9):4026–4037. Sep. 1992.*
Mattheakis et al. Diphthamide synthesis in *Saccharomyces cerevisiae*: structure of the Dph2 gene. Gene. vol. 132:149–154. 1993.*
Bölker, Michael, et al., "Tagging pathogenicity genes in *Ustilago maydis* restriction enzyme–mediated integration (REMI)", Mol Gen Genet 248:547–552, 1995.
Chen, D–C, et al., "One–step transformation of the dimorphic yeast *Yarrowis lipolytica*" Appl Microbiol Biotechnol 48:232–235, 1997.
Cordero Otero, R., et al., "Efficient selection of hygromycin–B–resistant *Yarrowia liplytical* transformants", Appl Microbiol Biotechnol 46:143–148, 1996.
D'Enfert, Christophe, "Selection of multiple disruption events in *Aspergillus fumigatus* using the orotidine–5'–decarboxylase gene, phyG, as a unique transformation marker", Curr Genet 30:76–82, 1996.
De Ruiter–Jacobs, Yolanda J.J.T., et al., "A gene transfer system based on the homologous phyG gene and efficient expression of bacterial genes in *Aspergillus oryzae*", Curr Genet 16:159–163, 1989.
Fincham, John R.S., "Transformation in Fungi" Microbiol Rev 53:148–170, 1989.

Foley, Brian T., et al., "Mutations in the Elongation Factor 2 Gene Which Confer Resistance to Diphtheria Toxin and Pseudomonas Exotoxin A", J. Biol Chem 270:23218–25, 1995.
Fonzi, William A., et al., "Isogenic Strain Construction and Gene Mapping in *Candida albicans*", Genetics 134:717–728, 1993.
Fotheringham, Scott et al., "Cloning and Disruption of *Ustilago maydis* Genes", Mol Cell Biol 9:4052–4055, 1989.
Gouka, R.J., et al., "A novel strategy for the isolation of defined pyrG mutants and the development of a site–specific integration system for *Aspergillus awamori*", Curr Genet 27:536–540, 1995.
Miller Bruce L., et al., "Direct and Indirect Gene Replacements in *Aspergillus nidulans*", Mol Cell Biol 5:1714–1721, 1985.
Neuvéglise, C., et al., "A shuttle mutagenesis system for tagging genes in the yeast *Yarrowia lipolytica*", Gene 213:47–46, 1998.
Punt, Peter J., et al., "Transformation of Filamentous Fungi Based on Hygromycin B and Phleomycin Resistance Markers", Methods Enzymol 216:447–457, 1992.
Skatrud, Paul L., et al., "Efficient integrative transformation of *Cephalosporium acremonium*", Curr Genet 12:337–348, 1987.
Sweigard, James A., et al., "Disruption of a *Magnaporthe grisea* cutinase gene", Mol Gen Genet 232:183–190, 1992.
Timberlake, William E., et al., "Genetic Engineering of Filamentous Fungi", Science 244:1313–1317, 1989.
Van den Hombergh, Johannes P.T.W., et al., "Regulation of acid phosphatases in an *Aspergillus niger* pacC disruption strain" Mol Gen Genet 251:542–550, 1996.
Walz, Markus, et al., "Targeted integration into the *Acremonium chrysogenum* genome: disruption of the pcbC gene", Curr Genet 24:421–427, 1993.
Weidner, Gerhard, et al., "Development of a homologous transformation system for the human pathogenic fungus *Aspergillus fumigatus* based on the pyrG gene encoding orotidine 5'–monophosphate decarboxylase", Curr Genet 33:378–385, 1998.
Woods, Jon P., et al., "Rare Homologous Gene Targeting in *Histoplasma capsulatum:* Disruption of the URA5 $_{Hc}$ Gene by Allelic Replacement", J Bacteriol 180:5135–5143, 1998.
Chen et al., "Diphtheria toxin–resistant mutants of *Saccharomyces cerevisiae*," Molecular and Cellular Biology 5:3357–3360 (1985).

(List continued on next page.)

*Primary Examiner*—Terry McKelvey
*Assistant Examiner*—William Sandals
(74) *Attorney, Agent, or Firm*—Law Offices of Wayne A. Keown

(57) ABSTRACT

The invention features a method of selectively killing a first microorganism. The method includes: (i) contacting the first microorganism with a second microorganism that has a microcidal compound; and (ii) allowing the first microorganism and the second microorganism to undergo fusion, whereby the microcidal compound is delivered into and kills the microorganism that forms following the fusion.

13 Claims, 31 Drawing Sheets

OTHER PUBLICATIONS

Choi et al., "Hypovirulence of chestnut blight fungus conferred by an infectious viral cDNA," *Science* 257:800–803 (1992).

Database Genbank, Accession No. Z35832 and Y13134, ORF YBL071C (1998).

Foley et al., "A mutation in codon 717 of the CHO–K1 elongation factor 2 gene prevents the first step in the biosynthesis of diphthamide," *Somatic Cell and Molecular Gene* 18:227–231 (1992).

Kimata et al., "Expression of non–adp–ribosylatable, diphtheria toxin–resistant elongation factor 2 in *Saccharomyces cerevisiae*," *Biochemical and Biophysical Research* 191:1145–1151 (1993).

Kohno et al., "Highly frequent single amino acid substitution in mammalian elongation factor 2 (EF–2) results in expression of resistance to EF–2–ADP–ribosylating toxins," *Journal of Biochemistry* 262:12298–12305 (1987).

Logghe et al., "The two genes encoding yeast ribosomal protein S8 reside on different chromosomes, and some are closely linked to the hsp70 stree protein genes SSA3 and SSA4," *Yeast* 10:1093–1100 (1994).

Mattheakis et al., "DPH5, a methyltransferase gene required for diphthamide biosynthesis in *Saccharomyces cerevisiae*," *Molecular and Cellular Biology* 12:4026–4037 (1992).

Mattheakis et al., "Diphthamide synthesis in *Saccharomyces cerevisiae:* structure of the DPH2 gene," *Gene* 132:149–154 (1993).

Moehring et al., "Characterization of the diphtheria toxin-resistance system in chinese hamster ovary cells," *Somatic Cell Genetics* 5:453–468 (1979).

Moehring et al., "Codominant translation mutants of chinese hamster ovary cells selected with diphtheria toxin," *Somatic Cell Genetics* 5:469–480 (1979).

Moehring et al., "Selection and characterization of cells resistant to diphtheria toxin and Pseudomonas exotoxin A: presumptive translation mutants," *Cell* 11:447–454 (1977).

Nuss, "Biological control of chestnut blight: an example of virus–mediated attenuation of fungal pathogenesis," *Microbiological Reviews* 56:561–576 (1992).

Perentesis et al., "Expression of diphtheria toxin fragment A and hormone–toxin fusion proteins in toxin–resistant yeast mutants," *Proc. Natl. Acad. Sci. USA* 85:8386–8390 (1988).

Phan et al., "*Saccharomyces cerevisiae* elongation factor 2; mutagenesis of the histidine precursor of the diphthamide yields a functional protein that is resistant to diphtheria toxin," *Journal of Biological Chemistry* 268:8665–8668 (1993).

\* cited by examiner

Killer — Non-Pathogenic Toxin$^R$

Target — Pathogenic Toxin$^S$

Mating or Fusion

Fusion = Dead

Fig. 1

Seq. ID No. 1

```
  1 TACGTATATAAAGTAGAAAATTCATACCTTTGAACAAGGTGATCTTTTCCTTTAGTTGATATTAATCCCGGGTAAACTTCCGTGTTGCA
    ATGCATATATTTCATCTTTTTAAGTATGAAACTGTTCCACTAGAAAAGGAAATCAACTATAATTAGGGCCCATTTGAAGGCACAACGT

91 CTTTTAAAATTTTTTTTTCAAATCTCACCTAGAAATTTTTTTGCATGAGCCTTCCTTTAATTAATCCATACTGTTCT
    GAAAATTTTAAAAAAAGTTTAGAGTGGATCTTTAAAAAAAACGTACTCGGAAGGAAATTAATTAGAGTTAACGTATGATGACAACA
```

Seq. ID No. 2

```
                                                                                 M  -  -
                                                                                 )- -

181 ATTAAACGCTTCACTGTTTTTTACTTAACCCATTTGCCAGAAAGCCAGACTTCCAAGAATTTTTAATAACAGATAAAAATG
    TAATTTGCGAAGTGACAAAAAAATGAATTGGGTAAACGGTCTTTCGGTCTGACGGTGGTTCTTAAAATTATTGTCTATTTTTAC

V  A  F  T  V  D  Q  M  R  S  L  M  D  K  V  T  N  V  R  N  M  S  V  I  A  H  V  D  H  G

271 GTTGCTTTCACTGTTGACCAAATGCGTTCTTTAATGGACAAAGTTACCAATGTGCGTAACATGTCCGTTATTGCTCACGTCGATCATGGT
    CAACGAAAGTGACAACTGGTTTACGCAAGAAATTACCTGTTCAATGGTTACACGCATTGTACAGGCAATAACGAGTGCAGCTAGTACCA

K  S  T  L  T  D  S  L  V  Q  R  A  G  I  I  S  A  A  K  A  G  E  A  R  F  T  D  T  R  K

361 AAGTCCACTTTGACCGATTCCTTGGTCCAAAGAGCCGGTATTATTTCCGCTGCTAAGGCTGGTGAAGCTCGTTTCACCGATACCAGAAAG
    TTCAGGTGAAACTGGCTAAGGAACCAGGTTTCTCGGCCATAATAAGGCGACGATTCCGACCACTTCGAGCAAAGTGGCTATGGTCTTTC

D  E  Q  E  R  G  I  T  I  K  S  T  A  I  S  L  Y  S  E  M  S  D  E  D  V  K  E  I  K  Q

451 GATGAACAAGAAAGAGGTATCACTATCAAGTCTACCGCTATTTCTCTATACTCTGAAATGTCTGACGAAGATGTCAAGGAAATCAAGCAA
    CTACTTGTTCTTTCTCCATAGTGATAGTTCAGATGGCGATAAAGAGATATGACTTTACAGACTGCTTCTACAGTTCCTTAGTTCGTT

K  T  D  G  N  S  F  L  I  N  L  I  D  S  P  G  H  V  D  F  S  S  E  V  T  A  A  L  R  V

541 AAGACCGACGGTAACTCCTTCTTGATCAACTTGATCGACTCCCCAGGTCACGTTGACTTCTCCTCTGAAGTTACTGCCGCTTTACGTGTC
    TTCTGGCTGCCATTGAGGAAGAACTAGTTGAACTGCTGAGGGTCCAGTGCAACTGAAGAGGAGACTTCAATGACGGCGAAATGCACAG

T  D  G  A  L  V  V  V  D  T  I  E  G  V  C  V  Q  T  E  T  V  L  R  Q  A  L  G  E  R  I

631 ACTGACGGTGCTTTGGTTGTCGTCGACACCATTGAAGGTGTCTGTGTCCAAACCGAAACTGTTTTGAGACAAGCTTTGGGTGAAAGAATC
    TGACTGCCACGAAACCAACAGCAGCTGTGGTAACTTCCACAGACAGGTTTGGCTTTGACAAACTCGTTCGAAACCACTTTCTTAG

K  P  V  V  V  I  N  K  V  D  R  A  L  L  E  L  Q  V  S  K  E  D  L  Y  Q  T  F  A  R  T

721 AAGCCTGTTGTTGTTATCAACAAGGTCGACAGAGCTTTGTTGGAATTGCAAGTTTCTAAGGAAGATTTATACCAAACCTTTGCCAGAACT
    TTCGGACAACAACAATAGTTGTTCCAGCTGTCTGAAACAACCTTAACGTTCAAAGATTCCTTCTAAATATGGTTTGGAAACGGTCTTGA
```

Fig. 3A

```
      V   E   S   V   N   V   I   V   S   T   Y   A   D   E   V   L   G   D   V   Q   V   Y   P   A   R   G   T   V   A   F
811   GTTGAATCCGTTAACGTCATCGTTTCCACTTACGCCGATGATGTCCAAGTTTTGGGTGATGTCCAAGTTTACCCAGCCAGAGGTACCGTTGCCTTC
      CAACTTAGGCAATTGCAGTAGCAAGTGCAATGCCGCTACTACAGGTTCAAAACCCACTACAGTTCAAATGGGTCGGTCGGTCCATGGCAACGGAAG
      G   S   G   L   H   G   W   A   F   T   I   R   Q   F   A   T   R   Y   A   K   K   F   G   V   D   K   A   K   M   M
901   GGTTCCGGTTTGCACGGTTGGGCTTTCACTATCCGTCAATTCGCCACCAGATATGCTAAGAAATTCGGTGTGTGACAAGGCCAAGATGATG
      CCAAGGCCAAACGTGCCAACCCGAAAGTGATAGGCAGTTAAGCGGTGGTCTATACGATTCTTTAAGCCACAGTGTTCCGGTTCTACTAC
      D   R   L   W   G   D   S   F   F   N   P   K   T   K   K   W   T   N   K   D   T   D   A   E   G   K   P   L   E   R
991   GACAGATTATGGGGTGACTCTTTCTTCAACCCAAAGACCAAGAAGTGGACCAACAAGGACACTGATGCTGAAGGTAAGCCATTGGAAAGA
      CTGTCTAATACCCCACTGAGAAAGAAGTTGGGTTTCTGGTTCTTGGACCTGGTTGTTCCTGTGACTACGACTTCCATTCGGTAACCTTTCT
      A   F   N   M   F   I   L   D   P   I   F   R   L   F   T   A   I   M   N   F   K   K   D   E   I   P   V   L   L   E
1081  GCTTTCAACATGTTCATCTTGGACCCAATCTTCAGATTATTCACTGCTATCATGAACTTCAAGAAAGACGAAATTCCAGTTTTGCTAGAA
      CGAAAGTTGTACAAGTAGAACCTGGGTTAGAAGTCTAATAAGTGACGATAGTACTTGAAGTTCTTTCTGCTTTAAGGTCAAACGATCTT
      K   L   E   I   V   L   K   G   D   E   K   D   L   E   G   K   A   L   L   K   V   V   M   R   K   F   L   P   A   A
1171  AAGTTGGAAATTGTCTTGAAGGGTGACGAAAAGGACTTGGAAGGTAAGGCCTTGTTGAAGGTTGTTATGAGAAAGTTCTTGCCAGCTGCC
      TTCAACCTTTAACAGAACTTCCCACTGCTTTTCCTGAACCTTCCATTCCGGAACAACTTCCAACAATACTCTTTCAAGAACGGTCGACGG
      D   A   L   L   E   M   I   V   L   H   L   P   S   P   V   T   A   Q   A   Y   R   A   E   Q   L   Y   E   G   P   A
1261  GATGCCTTATTGGAAATGATTGTCTTGCACTTGCCATCTCCAGTCACTGCTCAAGCTTACAGAGCTGAACAATTATACGAAGGTCCAGCT
      CTACGGAATAACCTTTACTAACAGAACGTGAACGGTAGAGGTCAGTGACGAGTTCGACGATGTCTCGACTTGTTAATATGCTTCCAGGTCGA
      D   D   A   N   C   I   A   I   K   N   C   D   P   K   A   D   L   M   L   Y   V   S   K   M   V   P   T   S   D   K
1351  GACGATGCCAACTGTATTGCTATCAAGAACTGTGATCCAAAGGCTGATTTGATGTTGTACGTCTCCAAGATGTGCCAACCTCTGATAAG
      CTGCTACGGTTGACATAACGATAGTTCTTGACACTAGGTTTCCGACTAAACATGCAGAGTTCTACCACGGTTGGAGACTATTC
      G   R   F   Y   A   F   G   R   V   F   A   G   T   V   K   S   G   Q   K   V   R   I   Q   G   P   N   Y   V   P   G
1441  GGTAGATTCTACGCCTTCGGTAGAGTTTTGCCGGTACTGTTAAGTCCGGTCAAAAGGTCAGAATCCAAGGTCCAAACTACGTTCCAGGT
      CCATCTAAGATGCGGAAGCCATCTCAAAACGGCCATGACAATTCAGGCCAGTTTTCCAGTCTTAGGTTCCAGGTTTGATGCAAGGTCCA
```

Fig. 3B

```
         K  K  D  D  L  F  I  K  A  I  Q  R  V  V  L  M  M  G  R  F  V  E  P  I  D  D  C  P  A  G
       AAGAAGGACGATTTGTTCATCAAGGCCATTCAAAGAGTTGTTTTGATGATGGGTAGATTTGTCGAACCAATCGATGACTGTCCAGCCGGT
1531   ----------------------------------------------------------------------------------------
       TTCTTCCTGCTAAACAAGTAGTTCCGGTAAGTTTCTCAACAAAACTACTACCATCTAAACAGCTTGGTTAGCTACTGACAGGTCGGCCA

N  I  I  G  L  V  G  I  D  Q  F  L  L  K  T  G  T  L  T  T  S  E  T  A  H  N  M  K  V  M
       AACATTATCGGTTTAGTCGGTATCGATCAATTCTTGTTGAAGACTGGTACTTTGACCACCAGTGAAACTGCTCACAACATGAAGGTCATG
1621   ----------------------------------------------------------------------------------------
       TTGTAATAGCCAAATCAGCCATAGCTAGTTAAGAACAACTTCTGACCATGAAACTTCTGACCATGGTGGTCACTTTGACGAGTGTTGTACTTCCAGTAC

K  F  S  V  S  P  V  V  Q  V  A  V  E  V  K  N  A  N  D  L  P  K  L  V  E  G  L  K  R  L
       AAATTCTCTGTCTCTCCAGTTGTCGCAAGTCGCTGTCGAGTCAAGAACGCTAACCACTTACCAAAAATTGGTCGAAGGTTTGAAGAGATTG
1711   ----------------------------------------------------------------------------------------
       TTTAAGAGACAGAGAGGTCAACAGCGTTCAGCGACAGCTCAGTTCTTGCGATTGGTGAATGGTTTTAACCAGCTTCCAAACTTCTCTAAC

S  K  S  D  P  C  V  L  T  Y  M  S  E  S  G  E  H  I  V  A  G  T  G  E  L  H  L  E  I  C
       TCCAAGTCTGATCCATGTGTCTTGACCTATATGTCTGAATCCGGTGAATCGTGCTGGTACCGGTGAATTGCATTTGAATTTGT
1801   ----------------------------------------------------------------------------------------
       AGGTTCAGATGGTACACAGAACTGGATATACAGATTAGGCACTTGTATGCAACGACCATGGCCACTTAAGCTAAACCTTTAAACA

L  Q  D  L  E  H  D  H  A  G  V  P  L  K  I  S  P  P  V  V  A  Y  R  E  T  V  E  S  E  S
       TTGCAAGATTTGGAACACGACCACGCTGGTGTTCCATTGAAGATCTCCCCACCAGTTGTCGCTTACAGAGAAACTGTTGAAAGTGAATCT
1891   ----------------------------------------------------------------------------------------
       AACGTTCTAAACCTTGTGCTGGTGCGACCACAAGGTAACTTCTAGAGGTGGTCAACAGCGAATGTCTCTTTGACAACTTCACTTAGA

S  Q  T  A  L  S  K  S  P  N  K  H  N  R  I  Y  L  K  A  E  P  I  D  E  E  V  S  L  A  I
       TCTCAAACTGCTTTGTCCAAGTCTCCAAACAAGCATAACAGAATCTACTTGAAGGCTGAACCAATTGACGAAGAAGTCTCTTTGGCTATT
1981   ----------------------------------------------------------------------------------------
       AGAGTTTGACGAAACAGGTTCAGAGGTTTGTTCGTATTGTCTTAGATGAACTTCCGACTTGGTTAACTGCTTCTTCAGAGAAACCGATAA

E  N  G  I  I  N  P  R  D  D  F  K  A  R  A  R  I  M  A  D  D  Y  G  W  D  V  T  D  A  R
       GAAAACGGTATCATCAACCCAAGAGATGATTTCAAGGCCAGAGCTAGAATCATGGCTGACGACTACGGTTGGGATGTCACCGATGCCAGA
2071   ----------------------------------------------------------------------------------------
       CTTTTGCCATAGTAGTTGGGTTCTCTACTAAGTTCCGGTCTCGATCTTAGTACCGACTGCTGATGCCAACCTACGTGCTACGGTCT

K  I  W  C  F  G  P  D  G  N  G  P  N  L  V  I  D  Q  T  K  A  V  Q  Y  L  H  E  I  K  D
       AAGATCTGGTGTTTCGGTCCAGACGGTAACGGTCCAAACTTGGTTATTGACCAAACTAAGGCTGTCCAATACTTGCACGAAATCAAGGAT
2161   ----------------------------------------------------------------------------------------
       TTCTAGACCACAAAGCCAGGTCTGCCATTGCCAGGTTTGAACCAATAACTGGTTTGATTCCGACAGGTTATGAACGTGCTTAGTTCCTA
```

Fig. 3C

```
        S   V   V   A   A   F   Q   W   A   T   K   E   G   P   I   F   G   E   E   M   R   S   V   R   V   N   I   L   D   V
2251    TCCGTTGTTGCTGCTTTCCAATGGGCTACCAAGGAAGGTCCAATTTTCGGTGAAGAAATGAGATCTGTCAGAGTTAACATTTTGGATGTT
        AGGCAACAACGACGAAAGGTTACCCGATGGTTCCTTCCAGGTTAAAAGCCACTTCTTTACTCTCTAGACAGTCTCAATTGTAAAACCTACAA

T   L   H   A   D   A   I   H   R   G   G   G   Q   I   I   P   T   M   R   R   A   T   Y   A   G   F   L   L   A   D
2341    ACTTTACATGCCGATGCTATCCACAGAGGTGGTGGTCAAATCATCCCAACCATGAGAGAGTACTTACGCCGGTTCTCTTGTTGGCTGAT
        TGAAATGTACGGCTACGATAGGTGTCTCCACCACCAGTTTAGTAGGGTTGGTACTCTTCTCGATGAATGCGGCCAAGAACAACGACTA

P   K   I   Q   E   P   V   F   L   V   E   I   Q   C   P   E   Q   A   V   G   G   I   Y   S   V   L   N   K   K   R
2431    CCAAAGATCCAAGAACCAGTTTTCTGGTGGTCGAAATTCAATGTCCAGAACAAGCCGTCGGTGGTATCTACTCCGTCTTAAACAAGAAGAGA
        GGTTTCTAGGTTCTTGGTCAAAGACCAGTCTTAAGTTACAGGTCTTGTTCGGCAGCCACCATAGATGAGGCAGAATTTGTTCTTCTCT

G   Q   V   V   S   E   E   Q   R   P   G   T   P   L   F   T   V   K   A   Y   L   P   V   N   E   S   F   G   F   T
2521    GGTCAAGTCGTTTCTGAAGAACAAAGACCAGGTACTCCATTGTTTACCGTCAAGGCCTACTTGCCAGTTAACGAATCTTTCGGTTTCACT
        CCAGTTCAGCAAAGACTTCTTGTTTCTGGTCCATGAGGTAACAAATGGCAGTTCCGATGAACGGTCAATTGCTTAGAAAGCCAAAGTGA

G   E   L   R   Q   A   T   G   G   Q   A   F   P   Q   M   V   F   D   H   W   S   T   L   G   S   D   P   L   D   P
2611    GGTGAATTGAGACAAGCTACCGGTGGTCAAGCTTTTCCCACAAATGGTTTTCGACCATTGGTCTCCACTTTAGGTTCTGACCCATTGGACCCA
        CCACTTAACTCTGTTCGATGGCCACCAGTTCGAAAAGGGTGTTTACCAAAAGCTGGTAACCAGAGGTGAAATCGAAGTCCAAGACTGGTAACCTGGGT

T   S   K   A   G   E   I   V   L   A   A   R   K   R   H   G   M   K   E   E   V   P   G   W   Q   E   Y   Y   D   K
2701    ACCTCTAAGGCTGGTGAATTGTTCTGCTCGTAAGAGACACGGTATGAAGGAAGAAGTTCCAGGCTGGCAAGAATATTACGACAAA
        TGGAGATTCCGACCACTTACCAAGAACGACGAGCATTCTCTGTGCCATACTTCCTTCTTCAAGGTCCGACCGTTCTTATAATGCTGTTT

L
        -->
2791    TTGTAAGAAGTCTAAATGAGAAAAGTGGTTCTGTAAGAGCAAACCTTACCGCCTTATGATCTTTTCATTTATTCTCTGCTTTAAAATT
        AACATTCTTCAGATTTACTCTTTTCCACCAAGACATTCGTTTGGAATGGCGAATACTAGAAAAAGTAAATAAGAGACGAAATTTTAA

2881    TTGTCGTAATAAAAAATAGTATGGTAATAGACTTATATATTCTTACACATTTTGTCATATAGTTATATTCCGAATGTTTACAATC
        AACAGCATTATTTTTATCATACCATTATCTGAATATATAAAGAATGTAAAAACAGTATATCAATATAAGCTTACAAATGTTAG

2971    GAACCCATCATAAAAATGGACCTTTTCGTATTACCGCCCCCCCTTTGTAGAGGGGAGGAAGCGCAACTTCTTGACTATTACGACGTATCAC
        CTTGGGTAGTATTTTACCTGGAAAAGCATAATGCGGGGAAACATCCCCCCTCCTTGCCGTTGAAGAACTGATAATGCTGCATAGTG

Fig. 3D
```

```
3061  CACCCCGTTAGATATACTATGGAAAAAAACTATTAAAAACCATTATAAATTCATTAATGACATCGGTCCTGAGGTAGTATTACGTATAACTT
      GTGGGGCAATCTATATGATACCTTTTTTGATAATTTTTGGTAATATTACTGTAGCCAGGACTCCATCATAATGCATATTGAA
3151  ACCTGGCTCTTGGTCATAGCTTTTTTATCCGTTTACGAAAAAAGGAGAAGAAGATTGGGCTTCCGCGGCTATTGTTGGTTATACCCCGC
      TGGACCCAGAACCAGTATCGAAAATAGGCAAATGCTTTTTCTTAACCCGAAGGCGCCGATAACAAACCAAATATGGGGCG
3241  CGTATGTTGGTGCTTCTATAATTAGAGCCGAAATACAAAAATCCTTGGAGGGGAGGACCAGCCTCATCGGGCTAAAACTCCCT
      GCATACAACCACGAAGATATTAATCTCGCTTTATCCTTTATGTTTTTTAGGAACCTCGGTCGGAGTAGCCCGATTTTGAGGGA
3331  CAAAACCGAGGGGCAACCAAGTATATCCATTATGGCCGATACTTCTAGAGGCGCACTAACAGAAGCACCTCAGCCCCTGCAGGTG
      GTTTTGGCCTCCCCGTTGGTTTCATATAGAGTAATACCGGCTATGAAGATCTCCGCGTGATTGTCTTCGTGGAGTCGGGACGTCCAC
3421  AAAGAAAGAGGTAATTAATTTTCCGGTTACTTACTTCTCGCTATTGGGAAAGCGTTGGTTCGAGGCGTTGAGGTCGAAGACAATCA
      TTTCTTTCTCCATTAATTAAAGGCCAATGAATGAAGAGAGCGATAACCCCTTTCGCAACTCCGCAACTCCAGCTTCTGTTAGT
3511  TTGTTTTCCTTCTTATTTAAGTACATCTTTAGAAGAAATTACACAACTGGAATGAGTAAATCAATACTTGCTTGTGTTCCCATTGTTAG
      AACAAAGAAGAATAAATTCATGTAGAAATCTTCTTTAATGTGTTGACCTTACTCATTAGTTATGAACGAAACACAAGGTAACAATC
3601  ATACTCTTGTTTTAGCATGTGATAGCAGTATATAATAATAACCTGCAAAATAATCGAAACGCGTACACAGGAAAAGAGTACATAAATAACCA
      TATTAGAAGACCAAATCCTAGACTTATAACTTTGCCATGCTTTTCTCATGTATTTATTGGT
3691  TAGTATATTTCTGGACATATCTTATTACAACATAAAATAGA
      ATCATATAAAGACCTGTATAGAATAATGTGTTGTATTTTATCT
```

```
        V  D  T  I  E  G  V  C  V  Q  T  E  T  V  L  R  Q  A  L  G  E  R  I  K  P  V  V  V  I  N
   811  GTCGACACCATTGAAGGTGTCTGTGTCCAAACGAAACTGTTTGAGACAACTGTTCTGAGAGAATCAAGCCTGTTGTTGTTATCAAC
        CAGCTGTGGTAACTTCCACAGACACAGTTTGCTTTGACAAACTCTGTTCGAAACCCACTCTCTTAGTTCGGACAACAATAGTTG

K  V  D  R  A  L  L  E  L  Q  V  S  K  E  D  L  Y  Q  T  F  A  R  T  V  E  S  V  N  V  1
   901  AAGGTCGACAGAGCTTGTTGGAATTGCAAGTTTCTAAGGAAGATTTATACAAACCTTTGCCAGAACCTTTGTTGAATCCGTTAACGTCATC
        TTCCAGCTGTCTCGAACAACAACCTTAACGTTCAAAGATTCCTTCTAAATATGTTTGGAAACGGTCTTGACAACTTAGGCAATTGCAGTAG

V  S  T  Y  A  D  E  V  L  G  D  V  Q  V  Y  P  A  R  G  T  V  A  F  G  S  G  L  H  G  W
   991  GTTTCCACCTACGCCGATGAAGTTTTGGGTGATGTCCAAGTTTACCCAGCCAGAGGTACCGTTGCCTTCGGTTCCGGTTTGCACGGTTGG
        CAAAGGTGGATGCGGCTACTTCAAAACCCACTACAGTTCAAATGGTCGGTCTCCATGCAACGGAAGCCAAGGCCAACTGCCAACC

A  F  T  I  R  Q  F  A  T  R  Y  A  K  K  F  G  V  D  K  A  K  M  M  D  R  L  W  G  D  S
  1081  GCTTTCACTATCCGTCAATTCGCCACCAGATATGCTAAGAAATTCGGTGTGTCGACAAGGCCAAGATGATGGACAGATTATGGGGTGACTCT
        CGAAAGTGATAGGCAGTTAAGCGGTGGTCTATACGATTCTTTAAGCCACAGCTGTTCCGGTTCTACTACCTGTCTAATACCCACTGAGA

F  F  N  P  K  T  K  K  W  T  N  K  D  T  D  A  E  G  K  P  L  E  R  A  F  N  M  F  I  L
  1171  TTCTTCAACCCAAAGACCAAGAAGTGGACCAACAAGGACACTGATGCTGAAGGTAAGCCATTGGAAAGAGCTTTCAACATGTTCATCTTG
        AAGAAGTTGGGTTTCTGGTTCTTCACCTGGTTGTTCCTGTGACTACGACTTCCATTCGGTAACCTTTCTCGAAAGTTGTACAAGTAGAAC

D  P  I  F  R  L  F  T  A  I  M  N  F  K  K  D  E  I  P  V  L  L  E  K  L  E  I  V  L  K
  1261  GACCCAATCTTCAGATTATTCACTGCTATCATGAACTTCAAGAAAGATGAAATTCCAGTTTTGCTAGAAAAGTTGGAAATTGTCTTGAAG
        CTGGGTTAGAAGTCTAATAAGTGACGATAGTACTTGAAGTTCTTTCTACTTAAGGTCAAAACGATCTTTTCAACCTTTAACAGAACTTC

G  D  E  K  D  L  E  G  K  A  L  L  K  V  V  M  R  K  F  L  P  A  A  D  A  L  L  E  M  I
  1351  GGTGACGAAAAGGACTTGGAAGGTAAGGCCTTGTTGAAGGTTGTTATGAGAAAGTTCTTGCCAGCTGCCGATGCCTTATTGGAAATGATT
        CCACTGCTTTTCCTGAACCTTCCATTCCGGAACAACTTCCAACAATACTCTTTCAAGAACGGTCGACGGCTACGGAATAACCTTTACTAA

V  L  H  L  P  S  P  V  T  A  Q  A  Y  R  A  E  Q  L  Y  E  G  P  A  D  D  A  N  C  I  A
  1441  GTCTTGCACTTGCCATCTCCAGTCACTGCTCAAGCCTACAGAGCTGAACAATTATACGAAGGTCCAGCTGACGATGCCAACTGTATTGCT
        CAGAACGTGAACGTAGAGGTCAGTGACGAGTTCGGATGTCTCGACTTGTTAATATGCTTCCAGGTCGACTGCTACGGTTGACATAACGA
```

Fig. 4B

```
          I  K  N  C  D  P  K  A  D  L  M  L  Y  V  S  K  M  V  P  T  S  D  K  G  R  F  Y  A  F  G
1531   ATCAAGAACTGTGATCCAAAGGCTGATTTGATGTTGTACGTCTCCAAGATGGTGCCAACCTCTGATAAGGGTAGATTCTACGCCTTCGGT
       TAGTTCTTGACACTAGGTTTCCGACTAAACTACAACATGCAGAGGTTCTACCACGGTTGAGACTATTCCCATCTAAGATGCGGAAGCCA

R  V  F  A  G  T  V  K  S  G  Q  K  V  R  I  Q  G  P  N  Y  V  P  G  K  K  D  D  L  F  I
1621   AGAGTTTTTGCCGGTACTGTTAAGTCCGGTCAAAAGGTCAGAATCCAAGGTCCAAACTACGTTCCAGGTAAGAAGGACGATTTGTTCATC
       TCTCAAAAACGGCCATGACAATTCAGGCCAGTTTTCAGGTTCCAGTCTTAGGTTCCAGGTTTGATGCAAGGTCCATTCTTCCTGCTAAACAAGTAG

K  A  I  Q  R  V  V  L  M  M  G  R  F  V  E  P  I  D  D  C  P  A  G  N  I  I  G  L  V  G
1711   AAGGCCATTCAAAGAGTTGTTTTGATGATGGGTAGATTTGTCGAACCAATCGATGACTGTCCAGCCGGTAACATTATCGGTTTAGTCGGT
       TTCCGGTAAGTTTCTCAACAAAACTACTACCCATCTAAACAGCTTGGTTAGCTACTGACAGGTCGGCCATTGTAATAGCCAAATCAGCCA

I  D  Q  F  L  L  K  T  G  T  L  T  T  S  E  T  A  H  N  M  K  V  M  K  F  S  V  S  P  V
1801   ATCGATCAATTCTTGTTGAAGACTGGTACTCTGACCACATCTGAAACATGAAGGTCATGAAATTCTCTGTCTCTCCAGTT
       TAGCTAGTTAAGAACAACTTCTGACCATGAGACTGGTGTACTTCCAGTACTTTAAGAGACAGAGAGGTCAA

V  Q  V  A  V  E  V  K  N  A  N  D  L  P  K  L  V  E  G  L  K  R  L  S  K  S  D  P  C  V
1891   GTGCAAGTCGCTGTCGAAGTCAAGAACGCTAACGACTTACCAAAATTGGTCGAAGGTTTGAAGAGATTGTCCAAGTCTGATCCATGTGTC
       CACGTTCAGCGACAGCTTCAGTTCTTGCGATTGCTGAATGGTTTTAACCAGTTCCAAACTTCTCTAACAGGTTCAGACTAGGTACACAG

L  T  Y  M  S  E  S  G  E  H  I  V  A  G  T  G  E  L  H  L  E  I  C  L  Q  D  L  E  H  D
1981   TTGACCTATATGTCTGAATCCGGTGAACATATCGTTGCTGGTACCGGTGAATTGCATTTGGAAATTTGTTTGCAAGATTTGGAACACGAC
       AACTGGATATACAGACTTAGGCCACTTGTATAGCAACGACCATGGCCACTTAACGTAAACCTTTAAACAAACGTTCTAAACCTTGTGCTG

H  A  G  V  P  L  K  I  S  P  P  V  V  A  Y  R  E  T  V  E  S  E  S  S  Q  T  A  L  S  K
2071   CACGCTGGTGTTCCATTGAAGATCTCCCCACCAGTTGTCGCTTACAGAGAAACTGTTGAAAGTGAATCTTCTCAAACTGCTTTGTCCAAG
       GTGCGACCACAAGGTAACTTCTAGAGGGGTGGTCAACAGCAAGTCTCTTTGACAACTTTCACTTAGAAGAGTTTGACGAAACAGGTTC
```

Fig. 4C

```
         S   P   N   K   H   N   R   I   Y   L   K   A   E   P   I   D   E   E   V   S   L   A   I   E   N   G   I   I   N   P
2161  TCTCCAAACAAGCATAACAGAATTACTTGAAGGCTGAACCAATTGACGAAGAAGTCTCTTTGGCTATTGAAAACGGTATCATCAACCA
      AGAGGTTTGTTCGTATTGTCTTAGATGAACTTCCGACTTGGTTAACTGCTTCTTCAGAGAAACCGATAACTTTTGCCATAGTAGTGGGT

R   D   D   F   K   A   R   A   R   I   M   A   D   D   Y   G   W   D   V   T   D   A   R   K   I   W   C   F   G   P
2251  AGAGATGATTTCAAGGCCAGAGCTAGAATCATGGCTGACGACTACGGTTGGGATGTCACCGATGCCAGAAAGATCTGGTGTTTCGGTCA
      TCTCTACTAAAGTTCCGGTCTCGATCTTAGTACCGACCTACTGATGCCAACCCTACAGTGGCTACGGTCTTTCTAGACCACAAAGCCAGT

D   G   N   G   P   N   L   V   I   D   Q   T   K   A   V   Q   Y   L   H   E   I   K   D   S   V   V   A   A   F   Q
2341  GACGGTAACGGTCCAAACTTGGTTATTGACCAAACTAAGGCTGTCCAATACTTGCACGAAATCAAGGATTCCGTTGTTGCTGCTTTCCAA
      CTGCCATTGCCAGGTTTGAACCAATAACTGGTTTGATTCCGACAGTTATGAACGTGCTTTAGTTCCTAAGGCAACAACGACGAAAGGTT

W   A   T   K   E   G   P   I   F   G   E   E   M   R   S   V   R   V   N   I   L   D   V   T   L   H   A   D   A   I
2431  TGGGCTACCAAGGAAGGTCCAATTTTCGGTGAAGAAATGAGATCTGTCAGAGTTAACATTTTGGATGTTACTTTACATGCCGATGCTATC
      ACCCGATGGTTCCTTCCAGGTTAAAAGCCACTTCTTACTCTAGACAGTCAATTGTAAAACCTACAATGTACGGCTACGATAG

H   R   G   G   G   Q   I   I   P   T   M   R   R   A   T   Y   A   G   F   L   L   A   D   P   K   I   Q   E   P   V
2521  CACAGAGGTGGTGGTCAAATCATCCCAACCATGAGAAGAGCTACTTACGCTGGTTTCTTGTTGGCTGATCCAAAGATCCAAGAACCAGTT
      GTGTCTCCACCACCAGTTTAGTAGGGTTGGTACTCTTCTCGATGAATGCGACCAAAGAACAACGACTAGGTTTCTAGGTTCTTGGTCAA

F   L   V   E   I   Q   C   P   P   E   Q   A   V   G   G   I   Y   S   V   L   N   K   K   R   G   Q   V   V   S   E   E
2611  TTCTTGGTCGAAATTCAATGTCCACCAGAACAAGCCGTCGGTGGTATCTACTCCGTCTTAAACAAGAAGAGAGGTCAAGTCGTTTCTGAAGAA
      AAGAACCAGCTTTAAGTTACAGGTCTTGTTCGGCAGCCACCATAGATGAGGCAGAATTGTTCTTCTCCAGTTCAGCAAAGACTTCTT

Q   R   P   G   T   P   L   F   T   V   K   A   Y   L   P   V   N   E   S   F   G   F   T   G   E   L   R   Q   A   T
2701  CAAAGACCAGGTACTCCATTGTTTACCGTCAAGGCCTACTTGCCAGTTAACGAATCTTTCGGTTTCACTGGTGAATTGAGACAAGCTACT
      GTTTCTGGTCCATGAGGTAACAAATGGCAGTTCCGGATGAACGGTCAATTGCTTAGAAAGCCAAAGTGACCACTTAACTCTGTTCGATGA

G   G   Q   A   F   P   P   Q   M   V   F   D   H   W   S   T   L   G   S   D   P   L   D   P   P   T   S   K   A   G   E   I
2791  GGTGGTCAAGCTTTCCCACAAATGGTTTTCGACCATTGGTCTCACTTTAGGTTCTGACCCATTGGACCCAACCTCTAAGGCTGGTGAAATT
      CCACCAGTTCGAAAGGGTGTTTACCAAAAGCTGGTAACCAGAGTGAAATCCAAGACTGGGTTGGAGATTCCGACCACTTTAA
```

Fig. 4D

```
        V  L  A  A  R  K  R  H  G  M  K  E  E  V  P  G  W  Q  E  Y  Y  D  K  L
        ------------------------------------------------------------------------>
2881    GTTCTTGCTGCTCGTAAGAGACACGGTATGAAGGAAGAAGTTCCAGGCTGGCAAGAATATTACGACAAATTGTAAGAATGGTTAAACAAT
        CAAGAACGACGAGCATTCTCTGTGCCATTCTTCCTTCTTCAAGGTCCGACCGTTCTTATAATGCTGTTTAACATTCTTACCAATTTGTTA

2971    TTTTAATTATTAACTTTTTCAGTTTTTGTCGTAATGTATTGGGCACCTTTTATGTCCTTTTGACTTTTTTGTAGTTTATTCTCACGTAT
        AAAATTAATAAATTGAAAAGTCAAAAACAGCATTCAAAAACAGGAAAATACCGTGGAAAATACAGGAAAACATGAAAAACATCAAATAAGAGTGCATA

3061    ACTTACCATCTATAGTGTTATTTCATATTTAATCATATTTCCATATTAGATATCTGCCTTCCCCTGTATAATAGTTACTATGATTTATCT
        TGAATGTAGATATCACAATAAAGTATAAATTAGTATAAAGTATAATCTATAGACGAAGGGACATATTATCAATGATACTAAATAGA

3151    TGCTTTGCCTATTCGCGTCATCAACTTCTTTTCTTACCGATCGCGGTAATGCCCTTTAAGAGTGGCATCAACATTGGCGTAAACAAAGTT
        ACGAAACGGATAAGCGCAGTAGTTGAAGAAAAGAATGGCTAGCGCCATTACGGGAAATTCTCACCGTAGTGTAACCGCATTGTTTCAA

3241    TCAAAGGATTGATACGAACACACATTCCTAGCCATGAAAGCATGAACTCTCATCAAACTTAAAAGACCTATATATTGAATGGTTACAAGA
        AGTTCCTAACTATGCTTGTGTGTAAGGATCGTACTTCGTACCTTGAGAGTAGTTTGAATTTTCTGATATATAACTTACCAATGTTCT

3331    ATTACTTCAACGGATTAACCGATTAAACAAGAACTATGAAAATAGCCTATGAAAAAGCAAAAAGGAATTTACAAAATGCTGAAGGTTCATT
        TAATCAACTGCCTAATTGGGGATTTGTTCTTGTTGAGTTTTATCGGATACTTTTTCGTTTTTCCTTAAATGTTTTACGACTTCCAAGTAA

3421    TTATTATCCTACAGATCTAAAGAAAGTTAAGGGAATT
        AATAATAGGATGTCTAGATTCTTTCAATTCCCTTAA
```

Fig. 4E

Seq. ID No. 5

```
   1 CGATCGAAGGTGTAAACTTCAGTAGTTCTCTTAATGCCGTTAATTCCAAGTCTCCTCGTTACCGTATTTATGTGTCATATACTCGAAA
     GCTAGCTTCCACATTTGAAGTCATCAAGAATTACGGCAATTAAAGGTTCAGAAGGAGCAATGGCATAAATACACAGTATATGAGCCTTT
  91 CATAGTACTCAGGATCAAACTTCAAATTTTCTTTTCTTAACCTTTCAATAACTCTATCGTTCGCGTCAGTGTGTTCAGATCGTCTAATT
     GTATCATGAGTCCTAGTTTGAAGTTTAAAAGAAAAGAATTGGAAAGTTATTGAGATAGCAAGCGCAGTCACACAAGTCTAGCAGATTAA
 181 CATTGATATCGTTCCCGTTGCTTGTCGACACTGATATAACTGTATCATATAAGTTATCAAACCCATATTTGTCTTCAATATTCCATTAT
     GTAACTATAGCAAGGGCAACAGCTGTGACTATATTGACATAGTATATTCAATAGTTGGGTATAAACAGAAGTTATAAGGTAATA
 271 TGGTGCTGGAATCCATCTTTGCTCTATCTCCCAATTAAACCCCTCTCCCATTTGACCAATAGTCTTCACATCATCTTTAATATTATTCG
     ACCACGACCTTAGGTAGAAACGAGATAGAGGGTTAATTTGGGAGAGGTAAACTGGTTATCAGAAGTGTAGTAGAAATTATAATAAGC
 361 ACACGCCATCAGTTTCGACCTCTTGAATAAGGGCTTTTTGGTTTTTTCGCATCAGTATTTCTGTTAATGCATCGGCACCTGCAAGAT
     TGTGCGGTAGTCAAAGCTGGAGAACTTATTCCCGAAAACCCAAAAAAGCTAGTCATAAAGACAATTACGTAGCCGTGGACGTTCTA
 451 CGCCTTGCCTAGCCAACAACTTTGTCGGTAGTCCAAATCTTCAGTTTAGAAGCTTTATAAGTAAAAATAAGTCAAACCGATGAAAATGTAACTACGTAA
     GCGGAACGGATCGGTTGTTGAAACAGCCATCCAGGTTTAGAAGCTTTATAAGTAAAAATAAGTCAAACCGATGAAAATGTAACTACGTAA
 541 CATCTTTGGAATCGTATTGAGCGGTAGACCTCTCATCATCGATTAATTCGTGAGGAAATCTTAATCTTAAATAGTAAGGGATAAGTGAA
     GTAGAAACCTTAGCATAAACTCGCCATCGAGAGTAGCTAATTAAGCACTCCTTTAGAATTAGAATTTATCATTCCCCTATTCACTT
 631 AAATGATCATATTTTCTTGGATGATTAATCTCTAAACCCACTGCACTGAACCTAATATTACTTATGAATATTTATAGCAAGTATATAAAATTCCT
     TTTACTAGTATAAAGAACCTACTAATAGAGATTTGGGTGACGTGACTTGGATTATAATGAATACTTATAAAACTCTTTATATTTAAGGA
 721 CATCCTCGTGTTATAGAGAATCTTGGTGTTATCATTATAGTTCAGAAGTGATGTAGATTATAGCAAGTATTCTTCTTTGTGAATCTTAA
     GTAGGACACAATATCTCTTAGAACCACATAGTAATCAAGTCTTCACTACCATCTAATATCGTTCATAAGAACACACTTAGAATT
 811 TATTACTCTGAGCACTTGACACTTGAAATATTTAGTATTCAAAATTTTTCAGCTGATTTTTGCGATGCGATGGTGATGAAAAAAACATG
     ATAATGAGACTCGTGAACTGTGACTTATAAATCATAAGTTTTAAAAAGTCGACTAAAAACGTACGCTACCACTACTTTTTTTGTAC
 901 TAGTAGTAATAACAATCAAATAAAATAAGTGAAATCTCATGAACTATCTGCTGCGAATTTTAAGGATAATCGGATAGTTGAAGCATTTC
     ATCATCATTATTGTTAGTTTATTTATTCACTTTAGAGTACTTGATAGAGACGACGCTTAAAATTCCTATTAGCTATCGAACTTCGTAAAG
```

Seq. ID No. 6                 M  S  G  S  T  E  S  K  K  Q  P  R  R  R  F  I  G  R  K  S  G  N  S  N  N  D  K
                              ]------------------------------------------------------------------------------[

```
 991 TTTTTCGTAATGAGTGGCTCTACAGAATCTAAAAACAACCAAGAAGAAGATTTATTGGGAGAAAATCTGCAACAGTAATGACAAA
     AAAAAGCATTACTCACCGAGATGTCTTAGATTTTTGTTGGTTCTTCTTCTAAATAACCCTCTTTTAGACCGTTGTCATTATTACTGTTT
```
                              R  K  S  G  N  S  N  N  D  K

Fig. 5A

```
         L   T   T   V   A   E   N   G   N   E   I   I   H   K   Q   K   S   R   I   A   L   G   R   S   V   N   H   V   P   E
1081  TTAACTACAGTGGCTGAAAATGGCAACGAAATAATCCACAAGCAAAAGAGTAGAATCGCCCTAGGTAGGAGTGTTAATCATGTGCCAGAA
      AATTGATGTCACCGACTTTTACCGTTGCTTATTAGGTGTTCGTTTTCTCATCTTAGCGGGATCCATCCTCACAATTAGTACACCGGTCTT
         D   I   L   N   D   K   E   L   N   E   A   I   K   L   L   P   S   N   Y   N   F   E   I   H   K   T   V   W   N   I
1171  GATATATTGAATGACAAAGAGTTGAATGAAGCCATCAAATTATTGCCCTCTAACTACAACTTTGAAATCCACAAAACTGTGTGGAATATC
      CTATATAACTTACTGTTTCTCAACTTACTTCGGTAGTTAATAACGGAGATTGATGTTGAAACTTTAGGTGTTTTGACACACCTTATAG
         R   K   Y   N   A   K   R   I   A   L   Q   M   P   E   G   L   L   I   Y   S   L   I   I   S   D   I   L   E   Q   F
1261  AGGAAATATAATGCTAAAAGAATAGCCCTACAGATGCCTGAAGGTTTGCTGATTTACTCATTGATTATAAGTGACATTTTGGAACAGTTC
      TCCTTTATATTACGATTTTCTTATCGGGATGTCTACGGACTTCCAAACGACTAAGATGAGTAACTAATATTCACTGTAAACCTTGTCAAG
         C   G   V   E   T   L   V   M   G   D   V   S   Y   G   A   C   C   I   D   D   F   T   A   R   A   L   D   C   D   F
1351  TGTGGTGTTGAAACTCTAGTAATGGGGGATGTGTCTTATGGTGCATGCTGTATTGATGATTTTACTGCTAGGCATTGGATTGCGATTTT
      ACACCACAACTTTGAGATCATTACCCCCTACACAGAATACCACGTACGACATAACTACTAAAATGACGATCCCGTAACCTAACGCTAAAA
         I   V   H   Y   A   H   S   C   L   V   P   I   D   V   T   K   I   K   V   L   Y   V   F   V   T   I   N   I   Q   E
1441  ATTGTGCATTACGCTCATTCGTGTTTAGTTCCTATTGACGTTACAAAGATTAAAGTACTATATGTCTTTGTTACTATAAATATTCAAGAA
      TAACACGTAATGCGAGTAAGCACAAATCAAGGATAACTGCAATGTTTCTAATTTCATGATATACAGAAACAATGATATTTATAAGTTCTT
         D   H   I   I   K   T   L   Q   K   N   F   P   K   G   S   R   I   A   T   F   G   T   I   Q   F   N   P   A   V   H
1531  GATCATATTATCAAAACGCTGCAGAAGAATTTCCTAAGGATCTAGAATGCTACACATTGGTACCATTCAGTTAATCCTGCGGTACAC
      CTAGTATAATAGTTTTGCGACGTCTTCTTCTTAAAGGATTCCCTAGATCTTAGCGATGTAACCATGGTAAGTCAATTAGGACGCCATGTG
         S   V   R   D   K   L   L   N   D   E   E   H   M   L   Y   I   I   P   P   Q   I   K   P   L   S   R   G   E   V   L
1621  AGCGTCAGAGATAAACTGCTTAACGATGAAGAACACATGCTGTATATTATTCCACCACAAATCAAGCCCTCTATCGAGGGGTGAAGTATTG
      TCGCAGTCTCTATTTGACGAATTGCTACTTCTTGTGTACGACATATAATAAGGTGGTGTTTAGTTCGAGATAGCTCCCCACTTCATAAC
```

Fig. 5B

```
         G  C  T  S  E  R  L  D  K  E  Q  Y  D  A  M  V  F  I  G  D  G  R  F  H  L  E  S  A  M  I
1711  GGGTGTACTTCTGAAAGATTAGATAAGAACAATACGATGCCATGGTATTCATCGGTGATGGTAGATTTCATTTGGAGTCTGCAATGATA
      CCCACATGAAGACTTTCTAATCTATTCTTGTTATGCTACGGTACCATAAGTAGCCACTACCATCTAAAGTAAACCTCAGACGTTACTAT

H  N  P  E  I  P  A  F  K  Y  D  P  P  Y  N  R  K  F  T  R  E  G  Y  D  Q  K  Q  L  V  E  V
1801  CATAATCCGGAAATTCCTGCATTCAAGTATGACCCATACAGAACAGAAGTTCACTAGAGAAGGATACGATCAAAAGCAACTCGTGGAAGTT
      GTATTAGGCCTTTAAGGACGTAAGTTCATACTGGGTATGTCTTTCAAGTGATCTCTTCCTATGCTAGTTTTCGTTGAGCACCTTCAA

R  A  E  A  I  E  V  A  R  K  G  K  V  F  G  L  I  L  G  A  L  G  R  Q  G  N  L  N  T  V
1891  AGAGCAGAGGCCATTGAAGTCGCTCGGAAGGGTAAAGTTTTTGGTCTGATCTTAGGTGCATTAGGTAGACAAGGTAATTAAACACTGTA
      TCTCGTCTCCGGTAACTTCAGCGAGCCTTCCCATTTCAAAACCAGACTAGAATCCACGTAATCCATCTGTTCCATTAATTTGTGACAT

K  N  L  E  K  N  L  I  A  A  G  K  T  V  V  K  I  I  L  S  E  V  F  P  Q  K  L  A  M  F
1981  AAAAACTTGGAAAAAAACCTGATCGCAGCAGGTAAAACCGTGGTGAAAATTATTCTAAGTGAAGTTTTCCCCAAAGCTCGCAATGTTC
      TTTTTGAACCTTTTTTTTGGACTAGCGTCGTCCATTTGGCACCACTTTTAATAAGATTCACTTCAAAAAGGGGTTTCGAGCGTTACAAG

D  Q  I  D  V  F  V  Q  V  A  C  P  R  L  S  I  D  W  G  Y  A  F  N  K  P  L  L  T  P  Y
2071  GATCAAATTGATGTTTTTGTTCAGGTCGCATGTCCTAGACTGTCCATCGATTGGGGTTATGCCTTCAATAAACCACTATTAACACCATAT
      CTAGTTTAACTACAAAAACAAGTCCAGCTACAGGATCTGACAGTAGCTAACCCCAATACGAAGTTATTTGGTGATAATTGTGGTATA

E  A  S  V  L  L  K  K  D  V  M  F  S  E  K  Y  Y  P  M  D  Y  Y  E  A  K  G  Y  G  R  G
2161  GAGGCTAGTGTCTTACTAAAGAAAGATGTCATGTTCAGCGAAAAATATTATCCAATGGATTATTACGAAGCTAAAGGATACGGGCGTGGG
      CTCCGATCACAGAATGATTTCTTTCTACAGTACAAGTCGCTTTTATAATAGGTTACCTAATAATGCTTCGATTCCTATGCCCGCACCC

E  T  P  K  H  A  I  E
2251  GAAACTCCGAAACATGCGATTGAATAGTTTAAATAGTTTTTGTTGTCACTTGTCTTCCTGTTACATATGTATAAATAGTTAGTATCATAT
      CTTTGAGGCTTTGTACGCTAACTTATCAAATTTATCAAAAACAGTGAACAGAGGACAATGTATACATATTATCAATCATAGTATA

2341  TCTTCGGAGCATCTTTTCTATTGTTTAAACGTTTTTGACGGGCTTGCAGGCGCGAAACTAAATTGTCTAAAATTCAAAACAATGCCTTCTAAC
      AGAAGCCTCGTAGAAAGATAACAAATTTGCAAAACTGCCGAACGTCCGCTTTGATTTAACAGATTTTAAGTTTTGTTACGGAAGATTG
```

Fig. 5C

```
2431  TTGATATCACTGCTGGTCAAGCCTATTTTATTCTGGTTTCTCAGGCAAACCCAAATGATATTGTCAAATTTTCACTGAGTTTGCCAAG
      AACTATAGTGACGACCAGTTCGGATAAAAATAAGACCAAAGAGTCCGTTGGGTTTACTACTATAACAGTTTAAAAAGTGACTCAAACGTTC

2521  CATATTTCCATGGACTTTTGTATGGAAACCGTGATGAGAAATCCGGGATTTCTCATCGAGGAAAGAAGTGACTCGAGCCTCTTAAGGCTT
      GTATAAAGGTACCTGAAAACATACCTTTGGCACTACTCTTTAGGCCCTAAAGAGTAGCTCCTTCTTCACTGAGCTCGGAGAATTCCGAA

2611  AGATTAAACTTTTTCTTTTTTATCGCTGCTGCGTATAAGCAATACACCTAAAACAGAACCAGTTAAAGTAAACCGATCAACAGTAAGAAGAT
      TCTAATTTGAAAAAGAAAAATAGCGACGCATATTCGTTAGTGGATTTTGTCTTGGTCAATTTCATTTGGGCTAGTTGTCATTCTTCTA

2701  GGGCAGGAAATTGCAACATTGCTAGAAATGGGAAGAGTAAACTCACAACTGATTGGAGTTCTGAAGATGGAGTTCTCGAAGATAGGCAGGAGCGA
      CCCGTCCTTTAACGTTGTAACGATCTTTACCCCTTCTCATTTGAGTGTTGACCTAACCTCAAGAGCTAGAGCTTCTATCCGTCCTCGCT

2791  CCATATGACATAATAAGTAAAAGAAGGCAAATAATTACAAAACGGTTCATGAAACTAAACAGACGTTTACTATGCCCAACCGGTGACTA
      GGTATACTGTATTATTCATTTTCTTCCGTTATTATTATGCCAAGTACTTTGATTTGTCTGCAAATGATACGGGTTGGCCACTGAT

2881  TTCACATTTTTGAGCTAGTATTGCATTTAGAGTACACGCAGTCATCAACAGTTTCTTCTTGTATCTCTTTCAAATATATCCTTTACACGGG
      AAGTGTAAAACTCGATCATAACGTAAATCTCATGTGCCTCAGTAGTTGTCAAAGAACATAGAGAAGTTTATATAAGGAAATGTCCCC

2971  AATGGTAGCGAATGAATGTACATTCGAATGGGGAAAGGCGAAAACTCTCCGTGCGAAACTATTCTTTAGACACTGAATAAAGTTGTAGCCTCATTCATA
      TTACGATCGGCTTTACTTACATTCCGGCCTTTGATCAACGCACGCTTTGATAAGAAAATCGTGACTTATTCAACATCGAGTAAGGTAT

3061  ATCTGGGTCAGATTTTATGAAAATGTAGTTATTCTGTTAGTTGCTACGATATTCGTCGCCGTGGTTTAGCTTTCATACTTGA
      TAGACCCAGTTCTAAAATACTTTTACATCAATAAGACAATCAACGACCAAGATGCTATAAGACGACGACCAAATCGAAAGTATGAACT

3151  TTTTTACTCCTTCATCACTCCATATAGGTTGGATATGGCTGAATCTGTTTTATCGAGGCACCCTTATGAACATAAACAACAGTATCCG
      AAAAATGAGGAAGTAGTGAGGTATATCCAACCTATACCGACTTAGACAAAAATAGCTCCGTGGGAATACTTGTATTGTTGTCATAGGGC

3241  TCTAAGAAATACTTTCGCTACAATGACTTCGAAAATT
      AGATTCTTTATGAAAGCGATGTTACTGAAGCTTTTAA
```

Fig. 5D

```
Seq. ID No. 7   1  ATCCATAATGATGGCTATGTGGTGCTAGATTTCTTCCGACTTCTTGCTATTTCATTCAAAAGGTTATACATGTTTATTTTCAACAGT
                   TAGGTATTACTACCGATACCACCACGATCTAAAGAAGCTGAAGAACGATAAAGTAAGTTTTCCAATATGTACAAAATAAAAAGTTGTCA

91  ACCTTAATATATAATAATCGGGGCCAAAATAACAAACAACGAGAAAAAGGAGGAGAGTAAAGTAAGTATAGTATTAACAGGGCTGGTTAT
                   TGGAATTATATATTATTAAGCCCCGGTTTTATTGTTTGCTCTCTCCATTCATTCATATCATAATTGTCCGACCAATA

181  ATAGATATATATATATATATACGGGTCAATCGATCTATTTATATACATACGAATATAATATGACATGGGGTGACACGATACAATATAATAGAG
                   TATCTATATATATATATATATGCCCAGTTAGCTAGATAAATATATGTCTTATATTATATACTGTACCCCACTGTGCTATGTTATATTATCTC

271  CGGGGACGGACACTTAGTTTGCGTCGGGATTGGAAGCGATATAATGACCGTTTCACCAACACTTCTCAACTCATCAGCCACTTGTCAG
                   GCCCCTGCCTGCCTGTGAATCAAACGCAGCCCTAACCTTCGCTATATTAGCTGGCAAAGTTGTGAAGAGTTGAAAACAGTC

361  GGATTTCAATATCAAATTCTCTTCAATAGCTACGAGCAGCTCGACAGTGTCCAAGGAGTCCAACCCCAAATCCTTGTGAAATTGGGTAT
                   CCTAAAGTTTATAGTTTAAGAAGAATTATCGATGCTCGTCGAGCTGTCACAGTTCCTCAGGTTGGGGTTTAGGAACACTTTAACCCATA

451  CGCTGGAGATTTGCTTGTTGGCAATGTTGGGAGAGTTCTTATCAAACGCCTTGATAACATCAATGACCCTTTGAGAAACCTGATCTTTGC
                   GCGACCTCTAAACGAACAACCGTTACAACCGTTCAAGAATAGTTGCGGAACTATTGTAGTTACTGGGAAACTCTTTGACTAGAAACG

541  TCAAGTTTGCAGAATAAAATCTTTGTGCGAGTATGGTGTTGGACATAACGGAACGGCCATTATAGTGCGGTACGCAGAAGGTGCCACGC
                   AGTTCAAACGTCTTATTTTAGAAACACGCTCATACCACAACCTGTATTGCCTGCCGGGTAATATCACGCCATGCGTCTTCCACGGTGCG

631  GGGAAGAAATGCGGCAAACGGATCTAAACATGGCAAGGAAGGTGCTGTATTGAGTTAGTTAGTTGTTGTTGTACTAATTACACTGCAAGTG
                   CCCTTCTTTACGCCGTTTGCCTAGATTTGTACCGTTCCTTCCACGACATAACTCAACACAACATGATTAATGTGACGTTCAC

721  TGACTATTCTTCCTTTGCTTCGTCATCACCACCTTCTCTTTTACTCAGAACCCGTTCGAAGGGGCGAAGAAAGAAGCAATTGACAAAT
                   ACTGATAAGACGAAGCGAAAACGAACGACTAGTGGTGAAGAGAAATGAGTTCTTGGGCAAGCTTCCCCGCTTCTTTCTTAACTGTTTA

811  AATCTGTATTCCGTCAACAGTGATATATGTCACGTAGACTTCAGAATGTCTTTTTAAGTATGCCATTGTGAAAAGAATAAT
                   TTAGACATAAGGCAGTTGTCACTATATACAGTGCACTGAGACTATTTGAGGTACCTCAGAGAAGCCTCACATACACTTTTCTTATTA

901  ACATATAAGACATCACAGGATCAGTCTGATAGTTTAATGCTATGGTAGACTTCAGAATGTCTTTTTAAGTATGCCATTGTTAAATC
                   TGTATATTCTGTAGATGTCCTAGTCAGATCAGATCAGATTATCAAAATTACGATACCATCTGAAGTCTTACAGAAAATTCATACGGTAAACCAATTTAG

991  TGTCCTTTATATGTACTTGGTGCTTCTCTTTTTTTTACTTTTTCTTTTCAGTGAGAAGCTCATCGCAACAAGAGCTCATCGCAACAAGAAAAAGACTAG
                   ACAGGAAAAATACATGAACCACGAAGAAAAAGAAAATGAAAAAAAAAAAGTCACTCTTCGAGTAGCGTTGTTCTTCTTTTTCTGATC
```

```
        F   H   V   P   E   D   V   D   Q   V   G   V   F   E   K   N   S   V   L   F   G   Q   H   D   K   A   D   N   I   S
1801    TTTCACGTTCCCGAAGACGTAGACCAGTGGTGTGTTGTTCGAAAAAAATAGCGTGCTGTTTGGTCAGCACGACGCAAAGCAGACAACATCTCG
        AAAGTGCAAGGGCTTCTGCATCTGGTCACCACACAAGCTTTTTTATCGCACGACAAACCAGTCGTGCTGCTGTTTCGTCGTCGTTGTAGAGC

P   E   D   Y   H   L   F   H   L   T   T   P   Q   D   P   R   L   L   Y   L   S   T   V   F   Q   S   V   H   I   F
1891    CCCGAGGACTATCATCTTTTTCATTTGACCACCCACAAGATCCGAGATTACTGTATTTGTCTCTGTGTTCAATCTGTTCATATTTC
        GGGCTCTGATAGTAGAAAAGTAAACTGGTGGGTGTCCTAGGCTCTAATGACATAAACAGATGACACAAAGTTAGACAAGTATAAAAG

D   P   A   L   P   G   M   V   T   G   P   F   F   P   S   L   M   R   R   Y   K   Y   M   H   V   A   R   T   A   G   C
1981    GATCCGGCTTTACCTGGCATGGTAACGGGGCCATTCCCTCTCTAATGAGGCGTTACAAGTACATGCATGGCAAGAACAGCGGATGT
        CTAGGCCGAAATGGACCGTACCATTGCCCCGGTAAGGGAGAGATTACTCCGCAATGTTCATGTACGTACACCGTTCTTGTCGCCTACA

I   G   I   L   V   N   T   L   S   L   R   N   T   R   E   T   I   N   E   L   V   K   L   I   K   T   R   E   K   K
2071    ATACGTTATTCTGTCAACACACTGTCTCTACGTAATACAACAGAAACTATCAACGAGCTCGTCAAGCTTATCAAAACTCGTGAGAAAAAA
        TATCCATAAGACCAGTTGTGCGACAGGCATGCATTATGTTCTCTTTGATAGTTGCTCGACCAGTTCGAATAGTTTGAGCACTCTTTTT

H   Y   L   F   V   V   G   K   P   N   V   A   K   L   A   N   F   E   D   I   D   W   C   I   L   G   C   S   Q
2161    CACTATTATTTGTTCGTCGGAAAGCCAAATGTGGCCAAGCTAGCAAACTTTGAAGATATTGATATTTGGTGCATTCTCGGTTGTAGCCAA
        GTGATAATAAACAACAGCCTTTCGGTTACACCGGTTCGATCGTTTGAAACTTCTATAACTATAAACCACGTAAGAGCCAACATCGGTT

S   G   I   I   V   D   Q   F   N   E   F   Y   K   P   I   I   T   P   Y   E   L   N   L   A   L   S   E   E   V   T
2251    AGCGGTATCATCGTTGATCAATTCAACGAGTTTTACAAGCCCATTATTACACCTTATGAATTAAACTTGGCCTTGAGCGAAGAGGTCACA
        TCGCCATAGTAGCAAGTAGTTAAGTTGCTCAAAATGTTCGGGTAATAATGTGGAATACTACTTAATTTGAACCGGAACTCGCTTCTCCAGTGT

W   T   G   K   W   V   V   D   F   R   D   A   I   D   E   I   E   Q   N   L   G   G   Q   D   T   I   S   A   S   T
2341    TGGACCGGAAATGGGTTGTGGACTTCAGAGACGCCATTGATGAAATCGAGCAGAATTTGGGCGGACAAGATACCATCTCTGCCAGCACA
        ACCTGGCCCTTTACCCAACACCTGAAGTCTCTGCGATGACTACTTTAGCTCGTCGTTCTATGGTAGAGACGGTCGTGT
```

Fig. 6C

```
        T  S  D  E  P  E  F  D  V  V  R  G  R  Y  T  S  T  S  R  P  L  R  A  L  T  H  L  E  L  E
2431    ACTTCCGATGAACCGGAGTTTGATGTAGTTAGGGGAAGATATACTAGCACATCAAGACCACTGCGAGCGCTAACGCACCTGGAGTTAGAG
        TGAAGGCTACTTGGCCTCAAACTACATCAATCCCCTTCTATATGATCGTGTAGTTCTGGTGACGCTCGCGATTGCGTGACCTCAATCTC

A  A  D  D  D  S  K  Q  L  T  T  R  H  T  A  S  G  A  V  I  K  G  T  V  S  T  G  A  S
2521    GCGGCCGACGACGAGACGATTCCAAACAACTGACTACAAGACATACCGCCTCAGGTGCCGTCATTAAAGGTACTGTATCCACTTCAGCATCA
        CGCCGGCTGCTGCTCTGCTAAGGTTTGTTGACTGATGTTCTGTATGGCGGAGTCCACGGCAGTAATTTCCATGACATAGGTGAAGTCGTAGT

A  L  Q  N  R  S  W  K  G  L  G  S  D  F  D  S  T  E  V  D  N  T  G  A  D  I  E  E  G  I
2611    GCACTGCAGAATCGTTCGTGGAAAGTCTAGGAAGCGATTTCGACTCTACTGAGGTTGATAATACTGGAGCGGATATCGAAGAAGGTATT
        CGTGACGTCTTAGCAAGCACCTTTCAGATCCTTCGCTAAAGCTGAGATGACTCCAACTATTATGACCTCGCCTATAGCTTCTTCCATAA

S  G  V  A  R  G  Y  G  F  D  R  E  D  A  M  K  K  E  N  K
                                                                   ------>
2701    TCCGGTGTCGCACGTGGTTATGGATTTGATCGCGAAGACGCTATGAAAAAGGAAAACAATGACTCTTATAATTGTTTCCCTCGACTTC
        AGGCCACAGCGTGCACCAATACCTAAACTAGCGCTTCTGCGATACTTTCTGCGAATATTAACAAAGGAGCTGAAG

2791    TCTATTTAAATCCAAGATTTTAACTAATAAACTATTAATAATAAACAATTAACTCTTTATATGGAAGCCTTGGAAATTAGCCGCCAAA
        AGATAAATTTAGGTTCTAAAATTGATTATTTGATAAATTATTATTTGTTAATTGAGAAATATACCTTCGGAACCTTTAATCGGCGTTT

2881    ATGGGATATACATTCCGTGCGAAGTGACCGCGTTGGAAGGCCGGTATCATCTTAAAAATCACTAGTTTCTTTTTTAGCGGAATGCAATAA
        TACCCTATATGTAAGGCACGCTTCACTGGCGCACCTTCCGGCCATAGTAGATAGAATTTTAGTGATCAAAGAAAAATCGCCTTACGTTATT

2971    AGGTGCTTTGTGCTGGTGTGTTTACACGGAACATCTAGTAGCAACATGTCCTTGTAGATCATCGATTTGAACCATTGAGTTACCACTAGTCTTAGTATCTTCGTAAAAA
        TCCACGAAACACGACCACCACCAAATGTGCCTTGTAGATCATCGATTTGAACCATTGAGTTACCACTAGTCTTAGTATCTTCGTAAAAA

3061    ATTTCTTAAAATGGGTGCTGCTCCTTCCAAATTG
        TAAAGAATTTTACCCACGACGAGGAAGGTTTTAAC
```

Fig. 6D

Seq. ID No. 9

| | |
|---|---|
| 1 | TCATATGACCATAGCACATACTTTTGTCCTGGTCTGTGTTTATAACGTCTCTTCTTGTGAGTACCAAAAGCAAATGGCAAGTGTAATTTCCT |
| | AGTATACTGGTATCGTGTATGAAAAACAGGACCACACAAATATTGCAGAAGAACACTCATGGTTTTCGTTTACCGTTCACATTAAAGGA |
| 91 | ATAACTTAAGATAGGCCTGTAAATAACGTATATGAAACAGTTCCATCCCGTAACACTGAACACTGCGTAAGAGAAGCCCTCAAGCT |
| | TATTGAAATTCTATCCGGACATTTATTGCATATACTTTCTCAAGGTAGGCATTGTGTACTTGTGACCCATTCTCTTTCGGAGTTCGA |
| 181 | TTCCCAGCGATGCTCGTGTGTAGGACCGAACATGGAGGGGAACTAGGCCCAGCGTTTGGCGAGGCCGCTCGTCTCGCAGCTCAG |
| | AAGGGTCGCTACGAGCACACATCCGGCTTGTACCTGTCGTCCCCCCTGATCCGGGTCGTGCCCAAACCGCTCCGGAGACGAGCGTCGAGTC |
| 271 | GATTCTAAAAGGTTATTCCGCTGAGAAATCAGAAATAGGAACTTCTCCACGGAACTTCTCCAAGTTTAAAGTTGATGAAAAGGAAAATTGTAA |
| | CTAAGATTTTCCAATAAGGCGACTCTTTTAGTCTTTTATCCTTGAAGAGTGCGTTATTAAAATTCAACTACTTTTCCTTTTAAACATT |
| 361 | AAGTGTAAGGGTGTTAAAGAGGGTGTATGGATGTAAAGTCACAAAGTTAGAGCAGATGAAAAGAAATGGTGGAGACAAATCCGAAAA |
| | TTCACATTCCCACAACAATTTCTCCCACATACCTACATTTCAGTGTTTTCAATCTCGTCTACTTTTCTTTACCCACCTCTGTTTAGGCTTTT |
| 451 | AGGACCTATATTATCGCTATAAAGAGCTTCTCATCGCTTTCTTTTTTTTCAAAGACACATACCACGACTGTAAGCACATCATTGTAC |
| | TCCTGGATATAATAGCGATATTTCTGAAGAGTAGCGAAAAAAAAGTTTCTGTGTATGTGCTGACATTCGTGTAGTAAACATG |

Seq. ID No. 10

| | | M S T Y D E I E D M T F E P E N Q M F T Y P |
|---|---|---|
| 541 | AATACATTACCAGCTGAAATGTCAACATATGACGAAATCGAAGATATGACGTTTGAGCCTGAAAATCAAATGTTCACCTATCCT | |
| | TTATGTAATGGTCGACTTTACAGTTGTATACTGCTTTAGCTTCTATACTGCAAACTCGGACTTTTAGTTTACAAGTGATAGGA | |
| | C P C G D R F Q I Y L D D M F E G E K V A V C P S C S L M I | |
| 631 | TGTCCCTGTGTGGAGATAGTTTCAAATATATCTGATGACATGTTTGAGGGCGAAAAAGTTGCTGTTTGTCCCAGCTGCTCACTGATGATC | |
| | ACAGGGACACCTCTATCCAAAGTTTATATAGACCTACTGTACAAACTCCCGCTTTTCAACGACAACAGGGTCGACGAGTGACTACTAG | |
| | D V V F D K E D L A E Y Y E E A G I H P P E P I A A A A > | |
| 721 | GATGTAGTTTTCGATAAAGAAGACTTGGCTGAGTACTACGAAGAGGCAGGCATCCACCCCCCTGAGCCTATTGCCGCTGCTAAAGA | |
| | CTACATCAAAAGCTATTTCTTCTGAACCGACTCATGATGCTTCCTGCCGTCCGTAGGTGGGGACTCCGATAACGGCGACGACGATTTCT | |
| 811 | TGAGAGGCTAGATCGAGAATACAAATAGAAATAAAGAAAGAGCTATATGACTTAGCAACGCAAGCAGAAAAGAAGTTTGCTTCTCGCT | |
| | ACTCTCCGATCTAGCTCTTATGTTTATCTTTATTTCTTTCTCGATATACTGAATCGTTGCGTTCGTCTTTTCTCCAAACGAAGAAGCGA | |

Fig. 7A

```
 901  GGACTCCGGTTGGAATTACTATTCAAAATTCCAAGTGCACTGATGGAAAACGTTTGCTCAGGTTGAGCTCTTTTACTGCATATAAGGAT
      CCTGAGGCCAACCTTAATGATAAGTTTTAAGGTTCACGTTGACTACCTTTTGCAAAACGAGTCCAACTGAGAAAATGACGTATATTCCTA

991  ACTGGGTAGGTGTATATGATTATTTTATACATGATACGTAGGCTAAAATGATTGGACCCATTAAATCATCTTGTCGCATCTCTTTCTT
      TGACCCATCCACATATACTAATAAAATATGTACTATGCATCCGATTTTACTAAACCTGGGTAATTTAGTAGAACAGCGTAGAGAAAGAA

1081  TTTCCTCCATGCTCAGATTTCAATAATATCATCTCAAATGGCTGTGACAAATTTCACCGGAAAGGCGAGGGATTTTCTGTTGACATTAT
      AAAGGAGGTACGAGTCTAAAGTTATTATAGTAGAGTTTACCGACACTGTTTAAAGTGGCCTTTCCGCTCCCTAAAAAGACAACTGTAATA
```

Fig. 7B

```
Seq. ID No. 11   1  CAAGTTTGATTCGTTGGTCTTACACAACACGGTTATTTACCACTACCGAAGACTAAAACTGTGAAGAGGTTAGAAGGTAACCTTGCAGCC
                    GTTCAAAACTAAGCAACCAGAAATGTTGTGCCAATAAATGGTGATGGCTTCTGATTTTGACACTTCTCCAATCTTCCATTGGAACGTCGG

91  TACAACTTTGAACTGTCAGACGAACAGATGAAATTTCTTGATCATCCTGATAGAGCCTACCGATTGGAATGCACAGACGCGCCA
                    ATGTTGAAACTTGACAGTCTGCTTGTCTACTTAAAGAACTAGTAGGACTACGAATATCCGATGCCTAACCCTTACGTCTCGCGGT

181  TAAAAGAAAATGCGAACCGTAGAATAACGTATATAGAACACATATAATAGTTTACGTTTCACAAAGTATTAATTACATGTAGCTTTT
                    ATTTTTCTTTTACGCTTGGCATCTTATTGCATCTTATCTGTATATTAATCAAATGCAAAGTGTTCATAATTATAATGTACATCGAAAAA

271  CAGGACTTTCGATCTAAATCAAAGATTAAGAGAGCTGCTAGAGGTAGAAAAGGAGAAATCATTGACTTTTCTTGAAGATTTATGAGCGGGTA
                    GTCCTGAAAGCTAGATTTAGTTTCTAATTTCCTCGACGATCTCCATCTTTTCCTTAGTAACTGAAAAGAACTTCTAAATACTCGCCCAT

361  ACTGGAGATGGAAATTTCAGAAAAATTGTAAATGATGCGATGACTTCGATGCGACTACTAGTTCTTACCATTGTAACATCTGATAG
                    TGACCTCTACCTTAAAGTCTTTTAAACATTTACTACGCTACTGAAGCTACACTGCAATGATCAGAATGGTAACATTTTGGTGATAG

451  GGTGCCAAAAGATAAGCGCAATCAACTAAGAAATTACCACGCTCTTTGTATTGTATTATCTCCAATTTAATCTTTCTTTTTGGTGTGAA
                    CCACGGTTTCTATTCGCGTTAGTGATTCTTTAAATGGTGCGAGAAACATAACATAAATAGAGGTTAAATTAGAAGAAAACCACACTT

Seq. ID No. 12      M  S  L  V  N  S  L  T  H  Y  E  I  L  R  I  P  S  D  A  T  Q  D  E  I  K  K
                    ]

541  AATTTAGCGAAAATGTCATTGGTAATTCGTTAACACACTCGTTAACACTACGAAATTTAAGAATTCCATCGGATGCAACACAAGATGAAATCAAAAAG
                    TTAAATCGCTTTTACAGTAACCATTAAGCACATTGAGCAATTGTGTGAGCTTAAAATTCTTAAGGTAGCCTACGTTGTGTTCTACTTTAGTTTTTC

A  Y  R  N  R  L  L  N  T  H  P  D  K  L  S  K  S  I  H  D  T  V  S  N  V  T  I  N  K  I

631  GCATATAGGAATCGGTTACTAAATACGCACCCGATAAACTTTCTAAAAGCATACATGATACGGTTAGCAACGTCACAATCAATAAGATT
                    CGTATATCCTTAGCCAATGATTTATGCGTGGGCTATTTGAAAGATTTCGTATGTACTATGCCAATCGTTGCAGTGTTAGTTATTCTAA

Q  D  A  Y  K  I  L  S  N  I  K  T  R  R  E  Y  D  R  L  I  L  E  N  Y  K  R  Q  G  F  H

721  CAAGATGCTTATAAAATACTATCGAATATAAAAACTCGTCGCGAATATGATAGGTTGATCCTTGAAAACTATAAACGCCAAGATTCAT
                    GTTCTACGAATATTTTATGATAGCTTATATTTTTGAGCAGCGCTTATACTATCCAACTAGGAACTTTGATATTGCGGTTCCTAAAGTA

N  C  G  D  G  L  D  E  F  S  L  D  D  F  S  F  E  D  K  L  E  F  M  M  N  C  P  R  C

811  AATTGTGGTGATGGGCTGGATGAATTTCCTTAGACGATTTCTCATTGATGAAGATAAGCTGGAGTTTATGATGAATTGTCCTCGCTGT
                    TTAACACCACTACCCGACCTACTTAAAGGAATCTGCTAAAGAGTAAACTACTTCTATTCGACCTCAAATACTACTTAACAGGAGCGACA
```

Fig. 8A

```
         Q  F  V  G  G  F  H  F  S  E  S  L  L  D  E  C  I  D  N  V  D  A  M  E  R  S  H  S  G  Y
         -----------------------------------------------------------------------------------------
  901    CAATTGTGTTGGTGGTTTCATTTTAGTGAGAGTTTGTTAGATGAATGCATTGATAATGTAGACGCTATGAACGGAGTCATTCTGGTTAT
         GTTAAACAACCACCAAAGTAAAATCACTCTCAAACAATCTACTTACGTGCGATACATCTGCCTCCAGTAAGACCAATA

Q  L  T  Q  C  S  A  C  S  L  W  L  K  V  N  F  D  I  E  E  E  Q  E  G  Q
         ----------------------------------------------------------------------->
  991    CAATTATTAACCCAATGTAGCGCATGCAGCTTATGGCTGAAGGTTAATTTTGACATCGAGGAAGAGCAAGAAGGACAATAATGAAAATGG
         GTTAATAATTGGGTTACATCGCGTACGTCGAATACCGACTTCCAATTAAAACTGTAGCTCCTTCTCGTTCCTGTTATTACTTTTACC

1081    GAGGGGAAATTGAGCTATATCAGATAAATCTGTTTATAGAATTATTATTTTACTTCGTGGGAAATCGAATGGTGTATATAAAGAGGTTGT
         CTCCCCTTTAACTCGATAGTCTATTAGACAAATATCTTAATATCTTAATAATGAAGCACCCTTTAGCTTACCACATATTTTCTCCAACA

1171    AAAATTGACGAAATAAATAGTATTTAGGCAACTAAAGATAAAAGATAAAAATATTATTTATTCGCGGTGCCTGCCAGATTTTTTTGA
         TTTTAACTGCTTATTATCATAATCCGTTGATTTCTATTTTTATAATAAAAATAAGGCCACGGACGAACGGTCTAAAAAAAACT

1261    CATGCGGAATTTTGGTAAAAAGAAAATGCAGATAATGAATAGTAAACAAAGGAATAAAAAGCCTTTCATGAAGAAGTTCGTGTTCGAGAT
         GTACGCCTTAAAACCATTTTCTTTTACGTCTATACTTATCATTGTTTCCTTATTTTCGGAAAGTACTTCTTCAAGCACAAGCTCTA

1351    CTTCTTCCTCTTTTTCGCTGTCGACGATAGATATGAATGCTTTGCCATTGATTTCAAATCCGTCATTAAGCTAACATGACCTGAAGAA
         GAAGAAGGAAGAAAAAGCGACAGCTGCTATCTATACTTACGAAAACGTAACTAAAGTTTAGGCAGTAATTCGATTGTACTGGACTTCTT

Seq. ID. No. 13    1 GCTTCTGGCGTCCGAGTCATTTTCCGTTCCTGGCCATTTGTCATAATCGAACCAAATTGAGAGTGTATAGACACCTGCAAATACTTACC
            CGAAGACCGCCAGGCTCAGTCAGTAAAAGGCAAGACCGGTAAACAGTATTAGCTTGGTTAAACTCTCACATATCTGTGGACGTTTATGAATGG

91 TGTATCATTGTTCAGGTCAGAGCCCATATTCTTTCCAACCATCAAGCTGTTTCCACCAGTTTGAAATTGTTACTTGAACTAGATT
              ACATAGTAACAAGTCCAGTCTCGGTCTGGGTATAATAGAAAGTTGGTAGTTCGACTTGAGGTGGTCAACTTTAAACAATGAACTTGATCTAA

181 CTTTTCTATCACATCTGTGGGCGGCACATGTCCCCTAATATACTGCACTATATGCTGACGCCAAGAAAACTTAATAAACATACCTAGCAG
              GAAAAGATAGTGTAGACACCCGCCGTCGTACAGGGATTATATGACGTGATACGACGCGGTTCCTTGAATTATTTTGTTATGGATCGTC

271 ATATATAATTAAGACACTTTATACTCCGCCAACGAGATTTAATAAGGGTCTCATTGCAACGTGATTCTCACTTCATCATTGAGGAGTTG
              TATATATTAATTCGTGAAATATGAGGCGGTTGCTCTAAATTATTCCCAGAGTAAACGTTGCAACTAGTAAGTAACTCCTCAAC

361 GCTTTCTTCAGTGTTTGGTCTCAACAGTGGTTGAGTTCTCAGATCTTGGTTATCCGCTCTGGGTGAGTTAGTGTGCATCTTAAAAGG
              CGAAAGAAGTCACAAACCAGAGTTGTCACCAACTGTGAACCAATAGGCGGAGCATTCCCACTCAATCACACGTAGAATTTTCC

451 TTCAAGGAGTAATGCACTACACTAAGCAATAAAAAATCCCAAAAACAGGAGGATCTTGTGTCTTCTCCCCTAGACATTCATCTTTTTG
              AAGTTCCTCATTACGTGATGTGATTCGTTATTTTTAGGGTTTTGTCCCTAGAACACAGAAGAGGGGATCTGTCAAGTAGAAAAAC

541 ATTCTGGCTTCGCATTTACCTTTAGAGAAAATTAAATAACCCATGCATGCGATTCTAAAAAAAGTTAACTAAGCGATGGATGAAAT
              TAAGACCCGAAGCGTAAATGGAAATCTCTTTAATTATTGGGTACGTACGCTAAGATTTTTTTCAATTGATTCGCTACCCTACTTTA

Seq. ID No. 14        M  L  Y  L  I  G  L
                                                                              ]-----------------

631 TTTTTTCTGGTGGTTGTTAGCAAAGTAAAAACGAACAGGATATAGAGTGAATAAAGGACAGTGAGAAAAATGCTTTATTGATCGGACTT
              AAAAAAGACCACCAACATCGTTTCATTTTGCTTGTCCTATATCTCACTTATTCCTGTCACTCTTTTTACGAAATAAACTAGCCTGAA
              G  L  S  Y  K  S  D  I  T  V  R  G  L  E  A  I  K  K  C  S  R  V  Y  L  E  H  Y  T  S  I

721 GGTCTCTGTACAAATCAGACATTACCGTTCGTGTTTGGAAGCTATTAAGAAATGTTCTAGAGTTTATCTAGAACACTATACCAGTATC
              CCAGAGAGACATGTTAGTCGTAATGGCAAGCACCAAACCTTCGATAATTCTTTACAAGATCTCAAATAGATCTGTGATATGGTCATAG
              L  M  A  A  S  Q  E  E  L  E  S  Y  Y  G  K  E  I  I  L  A  D  R  E  L  V  E  T  G  S  K

811 CTAATGGCTGCAAGCCAAGAAGAGTTAGAATCTTACTATGGTAAAGAGATCATCTTGGCTGATAGGGAATTAGTTGAGACTGGTTCTAAG
              GATTACCGACGTTCGGTTCTTCAATCTTAGAATGATACCATTTCTAGTAGAACGACTATCCTTAATCAACTCTGACCAAGATTC
              Q  I  L  N  N  A  D  K  E  D  V  A  F  L  V  V  G  D  P  P  F  G  A  T  T  H  T  D  L  V  L

Fig. 9A

```
901   CAGATCCTAAATAACGCCGATAAGGAAGACGTTGCTGCTTTCTTGGTCCTGGGCGATCCATTTGGTGCCACCACACAGATTTAGTTCTC
      GTCTAGGATTATTGCGGCTATTCCTTCTGCAACGAAGAACCAGACACCCGTAGGTAAACCACGGTGGTGTGTGTCTAAATCAAGAG
      R   A   K   R   E   A   I   P   V   E   I   I   H   N   A   S   V   M   N   A   V   G   A   C   G   L   Q   L   Y   N

991   AGAGCTAAACGTGAGGCAATTCCCGTCGAATTATTCATAATGCTCGTTATGAATGCAGTTGGGCATGTGCCTACAACTATACAAT
      TCTCGATTTGCACTCCGTTAAGGGCAGCTTTAATAAGTATTACGCAGGCAATACTTACGTCAACCCGTACACCGGATGTTGATATGTTA
      F   G   Q   T   V   S   M   V   F   F   T   D   N   W   R   P   D   S   W   Y   D   K   I   W   E   N   R   K   I   G

1081  TTCGGTCAAACCGTTTCCATGGTTTTCTTTACCGATAATTGGAGACCAGACTCATGTACGACAAGATCTGGAAATAGAAAAATTGGC
      AAGCCAGTTTGGCAAAGGTACCAAAGAAATGGCTATTAACCTCTGGTCTGAGTACCATGCTGTTCTAGACCCTTTATCTTTTTAACCG
      F   G   Q   T   V   S   M   V   F   F   T   D   N   W   R   P   D   S   W   Y   D   K   I   W   E   N   R   K   I   G
      L   H   T   L   V   L   L   D   I   K   V   K   E   Q   S   I   E   N   M   A   R   G   R   L   I   Y   E   P   P   R

1171  CTTCATACTTTAGTGTTATTGGACATCAAAGTTAAGGAACAAAGCATTGAAAATATGCCCGTGGCAGACTAATCTACGAACCACCAAGA
      GAAGTATGAAATCACAATAACCTGTAGTTTCAATTCCTTGTTTCGTAACTTTTATACCGGGCACCGTCTGATTAGATGCTTGGTGTTCT
      Y   M   S   I   A   Q   C   C   E   Q   L   L   E   I   E   E   K   R   G   T   K   A   Y   T   P   D   T   P   A   V

1261  TACATGTCTATCGCTCAATGTTGTGAACAATTATTAGAAATTGAAGAGAAAAGAGGTACAAAGGCATACACTCCTGATACTCCAGCAGTC
      ATGTACAGATAGCGAGTTACAACACTTGTTAATAATCTTTAACTTCTCTTTTTCCTATGTGAGGACTATGAGGTCGTCAG
      A   I   S   R   L   G   S   S   S   Q   S   F   K   S   G   T   I   S   E   L   A   N   Y   D   S   G   E   P   L   H

1351  GCAATTAGTAGTAGATTAGGCTCGAGCTCCGAGCTCCAAAGCTTTAAGTCTGTAGTCTATAAGTGAGTTAGCCAATTACGATTCAGGAGAGCCACTTCAT
      CGTTAATCATCTAATCGAGCTCGAGGTTTCGAAATTCAGACGATTCACTCAATCGGTTATTCTAAGTCCTCTCGGTGAAGTA
      S   L   V   I   L   G   R   Q   C   H   E   L   E   L   E   Y   L   L   E   F   A   D   D   K   E   K   F   G   K   D

1441  TCGCTTGTCATCCTCGGCAGACAGACAATGTCATGAATTGGAGCTGGAATACCTGCTAGAGTTTGCCGACGACAAAGAAAAGTTTGGGAAAGAT
      AGCGAACAGTAGGAGCCGTCGTTACAGTACTACTTAACCTGACCTTATGACGATCTCAAACGGCTGCTGTTTCTTTTCAAACCCTTCTA
      V   A   N   D   Q   E   Y   F   K   P   A   A   W   V   P   P   T   E   D   D   S   D   E

1531  GTGGCAAATGACCAAGAGTACTTCAAACCTGCGGCATGGGTCCACCCAGGGTGGGTGTCTTCGTCGCTGCTGTGCTGAAGGTAATGCACGCTCA
      CACCGTTTACTGGTTCCATCATGAAGTTTGGACGCCGTACCCAGGGTGGGTGTCTTCGTCGCTGCTGTGCTGAAGGTAATGCACGCTCA
                                          -   -   -   >
```

Fig. 9B

1621 TGTGTAGTTCTTTTTATAATGTATATTGAATAGATCCTTTCAGTCGGTAACAATTCGATCCCAAACGAATCGGGCCCTAACGATATG
     ACACATCAAAGAAAAATATTACATATAACTTATCTAGGAAAGTCAGCCCATTGTTAAGCTAGGGTTTGCTTAGCCCGGATGCTATAC

1711 TGTAAAAATGGCAATGAATGAACAAGAAGTTATAACAACAATTCAGCCAAGAACAAGAGCGATCCTGGAGGAGATTATATACGGATACA
     ACATTTTTACCGTTACTTGTTCTTCAATATGTTGTTAAAGTCGGTTCTTGTTCTCGCTAGGACCTCCTCTAATATATGCCTATGT

1801 CAGGTACACAAGATGACGCAATTAAAATATTTGTTGCTGGTTTCTAGGCAAGAAAAATCAGATTAAAGAAATGTACACGGCAATGTCC
     GTCCATGTGTTCTACTGCGTTAATTTTATAAACAACGACCAAAGATCCGTTCCTTTTAGTCTAATTTCTTTACCATGTGCCGTTACAGG

1891 GCTGGTGAAAGGCAAAAATTGTGAAAGACTTGACACCTACGATATTAGCAAGAAAACCCAAATGTGTAACATCATCGAGTATAATGAC
     CGACCACTTTCCGTTTTTAACACTTTCTGAACTGTGATGCTATAATCGTTCTTTGGGTTTACACATTCGTAGTAGCTCATATTACTG

1981 CACAAAGTAGTATACAAGCGATATGCTAGTCTATATTTATTGTTGGGATGACGCCCGATGTTGACAATGAACTGCTGACCTTGGAAATT
     GTGTTTCATCATATGTTCGCTATACGATCAGATATAAAATAACAACCCTACTGCGGGCTACAACTGTTACTTGACGACTGGAACCTTTAA

2071 ATCCATCGGTTTGTCGAAACAATGACACATATTTCGGCAATGTTTGTGAGCTAGACATTATATTAACTTCAGTAAGGTCTACGATATC
     TAGGTAGCCAAACAGCTTTGTTACCTGTGTATAAAGCCGTTACAAACACTCGATCTGTAATATAAATTGAAGTCATTCCAGATGCTATAG

2161 TTGAATGAGATGATTATGTGCGATGGCTCCATCGCAGAGAGCAGTAGGAAGGAAGTACTGCACCATGTGACCGTGATGACACCATGGAG
     AACTTACTCTAATACACGCTACCGAGGTAGCGTCTCTCGTCATCCTTCCTTCATGACGTGGTACACTGGCACTACCTGTGTACCTC

2251 AGCAACGATAATCTTGAAAGGGTATTGAGTTAGGACCACTAAAAAACAA
     TCGTTGCTATTAGAACTTTCCCATAACTCAATCCTGGTGATTTTTGTT

Fig. 9C

| Gene/Sequence Origin DPH1 | Size | Locus | Gene Name | Score |
|---|---|---|---|---|
| Annotated Sequences | | | | |
| S. cerevisiae | 534aa | 416911 | DPH2 | 4e-13 |
| C. elegans | 954aa | 1730588 | YKY5_CAEEL | 5e-93 |
| | 495aa | 2496888 | C09G5 | 6e-12 |
| S. pombe | 503aa | 1723275 | C13F4.15C | 3e-27 |
| M. thermoautotrophicum | 330aa | 2622425 | MTH1319 | 6e-27 |
| A. fulgidus | 310aa | 2648743 | AF1803 | 2e-19 |
| M. jannaschii | 340aa | 2496001 | MJ0483 | 2e-17 |
| H. sapiens | 443aa | 1438796 | OVCA1 | 1e-105 |
| ESTs | | | | |
| D. melanogaster | 565bp | AA567531 | HL01407 | 1e-48 |
| | | AA440344 | LD14920 | 9e-37 |
| | | AA264244 | LD07965 | 8e-32 |
| | | AA536461 | LD17078 | 4e-25 |
| M. musculus | 520bp | AA667431 | 1222706 | 4e-40 |
| B. malayi | 437bp | AA283566 | SW3ICA2711 | 6e-33 |
| | | AA280486 | SWMFCA2172SK | 1e-26 |
| C. elegans | | C45088 | yk376a7 | 4e-29 |
| H. sapiens | | AA292364 | zt51g03.r1 | 7e-25 |
| | | H44194 | yo73f10.r1 | 4e-24 |
| | | H80963 | yu58g04.r1 | 6e-24 |
| | | H26521 | yl13e02.r1 | 1e-19 |
| P. faciparum | | T09561 | 0163m3 | 3e-10 |

Fig. 10A

| Gene/Sequence Origin | Size | Accesion | Gene Name | Score |
|---|---|---|---|---|
| DPH2 | | | | |
| Annotated Sequences | | | | |
| S. cerevisiae | 425aa | 731852 | DPH1/YIL103w | 2e-11 |
| S. pombe | 503aa | 1723275 | C13F4.15c | 6e-44 |
| C. elegans | 495aa | 2496888 | C09G5.2 | 4e-21 |
|  | 954aa | 1730588 | C14B1.5 | 6e-6 |
| H. sapiens | 363aa | 438781 | DPH2L | 2e-8 |
|  | 443aa | 1438796 | OVCA1 | 3e-12 |
| ESTs | | | | |
| C. elegans |  | C71510 | yk446a6 | 3e-10 |
| A. thaliana |  | N37933 | 21306T7 | 4e-8 |
| D. melanogaster |  | AA697424 | HL02446 | 2e-6 |
|  |  | AA696128 | GM05116 | 8e-5 |
|  |  | AA390565 | LD09414 | 1e-5 |
| M. musculus |  | AA155133 | mr97g06.r1 | 3e-5 |
| H. sapiens |  | H52976 | yq82f03.r1 | 1e-4 |
| DPH3 | | | | |
| Annotated Sequences | | | | |
| C. elegans | 80aa | 1122819 | K01H12.1 | 4e-15 |
| ESTs | | | | |
| O. sativa (rice) | 276bp | C19915 |  | 9e-16 |
|  |  | RICR0153A | R0153_1A | 2e-14 |
| B. malayi |  | AA471545 | MBAFCX3G01T3 | 5e-14 |
|  |  | AA241420 | MBL2SJ9E9T3 | 5e-14 |
|  |  | AA41619 | MBL2SJ2C5T3 | 5e-14 |
|  |  | N44462 | SWMFCA184SK | 5e-14 |
|  |  | AA542688 | MB4SLY2B03T3 | 2e-13 |
|  |  | AA514136 | SWMFCA2240SK | 4e-13 |
| O. volvulus |  | AA294252 | SWOv3MCA221SK | 5e-13 |
|  |  | AA294195 | SWOv3MCA1590SK | 7e-10 |
| M. musculus |  | AA016825 | mh42f09.r1 | 1e-14 |
|  |  | AA184808 | mu45g08.r1 | 1e-14 |
|  |  | AA065470 | ml51g09.r1 | 1e-14 |
|  |  | W78238 | me77e03.r1 | 1e-14 |
|  |  | AA276213 | vc31f07.r1 | 7e-14 |
|  |  | AA717576 | vt97b09 | 5e-11 |
|  |  | AA199191 | mv42h11.r1 | 5e-10 |
| H. sapiens |  | C17048 | GEN-537F01 | 1e-10 |
|  |  | R67792 | yi24b12.r1 | 8-15 |
|  |  | Ne3990 | yw70a10.r1 | 1e-14 |
|  |  | AA625207 | af70e11.r1 | 1e-14 |
|  |  | H72496 | ys07d8.r1 | 5e-10 |
|  |  | R67101 | yi31b05.r1 | 8e-13 |
|  |  | H12887 | yj14g09.r1 | 5e-10 |

Fig. 10B

| Gene/Sequence Origin DPH5 | Size | Accesion | Gene Name | Score |
|---|---|---|---|---|
| Annotated Sequences | | | | |
| C. elegans | 274aa | 872040 | B0491.7 | 9e-82 |
| M. jannaschii | 257aa | 2127853 | | 1e-47 |
| M. thermoautotrophicum | 264aa | 2623012 | MTH1874 | 3e-42 |
| A. fulgidus | 251aa | 2650252 | DPH5 | 1e-36 |
| P. furiosus | 213aa | e314266 | DPH5 | 1e-29 |
| ESTs | | | | |
| C. intestinalis | | AJ227693 | 74A | 2e-36 |
| B. malayi | | AA180573 | MBAFCF7F10T3 | 3e-6 |
| Leishmania major | | T67355 | lmEST0057 | 2e-17 |
| A. thaliana | | N97026 | 246H11T7 | 2e-19 |
| D. melanogaster | | AA390572 | LD09450 | 7e-58 |
| | | AA392956 | LD12153 | 2e-43 |
| M. musculus | | AA671897 | 963817 | 7e-44 |
| | | AA142820 | mq63g08.r1 | 2e-23 |
| H. sapiens | | AA385447 | ATCC189616 | 2e-29 |
| | | N98264 | 293903 | 3e-28 |
| | | AA316398 | EST188117 | 2e-21 |
| | | R96579 | yq54b09.s1 | 2e-20 |
| | | AA088658 | zk71h07.r1 | 1e-18 |
| | | AA371380 | EST83159 | 7e-16 |
| | | AA366110 | EST77012 | 9e-16 |
| | | AA334618 | EST38861 | 7e-14 |
| | | N28882 | yx60h09 | 5e-9 |

Fig. 10C

List of Strains and Relevant Genotypes:

Target: TMY407 *MAT*α <pRS426: *URA3 2μ*>

ToxinR Target: TMY403 *MAT*α *dph1Δ::TRP1* <pRS426: *URA3 2μ*>

Killer + DT: TMY401 *MATa dph1Δ::TRP1* <pTM147: *EFT2:DT HIS3 CEN*>

Killer no DT: TMY401 *MATa dph1Δ::TRP1* <pRS313: *HIS3 CEN*>

METHOD FOR EFFICIENT AND HIGHLY SELECTIVE CONTROL OF MICROORGANISMS

CROSS-REFERENCE TO RELATED APPLICATIONS

This application claims benefit from provisional application "Mate and Die (MAD): Novel method for efficient and highly selective control of microorganisms" (U.S. Ser. No. 60/082,089), filed Apr. 17, 1998.

STATEMENT AS TO FEDERALLY SPONSORED RESEARCH

The invention has been sponsored in part by Grant GM 35010 from the National Institutes of Health. The Government has certain rights in the invention. The invention has also been supported by funding from Damon Runyon—Walter Winchell Cancer Research Grant DRG 1378.

BACKGROUND OF THE INVENTION

Microbial pathogens greatly reduce yields of a variety of important food crops (e.g., corn, rice), threaten entire industries (e.g., rubber, tobacco), and devastate ornamental plants and trees (e.g., elm, chestnut, ash). Unfortunately, treatment with broad-spectrum antimicrobial agents destroys, in addition to the pathogen, important commensal or non-pathogenic organisms and, thus, can facilitate the subsequent colonization by additional pathogens. Therefore, the ideal antimicrobial treatment or therapy is a substance that selectively kills or eliminates specific pathogenic organisms while having minimal effects on the microbial ecology. The importance of the microbial ecology is well-illustrated in the successful use of "antagonistic yeasts," such as *Epicoccum nigrum, Penicillium oxalicum*, and *Candida sake*, in the control of brown rot of peaches and other fruit. In these examples, protection is a result of the ability of the applied fungal strains to rapidly colonize the fruit and prevent subsequent colonization by organisms associated with post-harvest decay. While these antagonistic approaches can serve as prophylactic treatments, they are much less effective displacing or selectively killing pathogenic or undesirable microorganisms once colonization has occurred.

Selective killing of a microorganism can be achieved by development of a substance that is either selectively toxic or one that is generally toxic but selectively targeted. Development of either type of antimicrobial agent is plagued by the inherent similarities between pathogenic and non-pathogenic organisms at the level of physiology, nutrient requirements, and biology.

Virtually all organisms mate or fuse to allow exchange of genetic and/or other intracellular components. In fungi, fusion is not a random event, but rather is restricted to occur only between members of the same species, and often includes a further dependency on secondary characteristics such as mating type and vegetative compatibility group (VCG). For instance, haploid strains of *S. cerevisiae* will mate and fuse only if they are of opposite mating types. In addition to mating, many filamentous fungi are also able to undergo anastomosis (hyphal fusion) but only if they are of the same vegetative compatibility group. Importantly, these fusion reactions occur with absolute selectivity.

SUMMARY OF THE INVENTION

We have harnessed the biological discriminatory mechanisms described above to selectively target and kill pathogens.

Accordingly, in a first aspect, the invention features a method of selectively killing a first microorganism. The method includes: (i) contacting the first microorganism with a second microorganism that contains a microcidal compound; and (ii) allowing the first microorganism and the second microorganism to undergo fusion, whereby the microcidal compound is delivered into and kills the microorganism that forms following the fusion.

In a preferred embodiment, the first microorganism is fungus. Preferred fungi include Absidia spp., *Actinomadura madurae*, Actinomyces spp., *Allescheria boydii*, Altemaria spp., *Anthopsis deltoidea*, Aphanomyces spp., *Apophysomyces eleqans*, Armillaria spp., *Arnium leoporinum*, Aspergillus spp., Aureobasidium pullulans, *Basidiobolus ranarum*, Bipolaris spp., *Blastomyces dermatitidis*, Botrytis spp., Candida spp., Centrospora spp., Cephalosporium spp., Ceratocystis spp., Chaetoconidium spp., Chaetomium spp., Cladosporium spp., *Coccidioides immitis*, Colletotrichum spp, Conidiobolus spp., *Corynebacterium tenuis*, Cryptoporiopsis spp., Cylindrocladium spp., Cryptococcus spp., *Cunninghamella bertholletiae*, Curvularia spp., Dactylaria spp., Diplodia spp., Epidermophyton spp., *Epidermophyton floccosum*, Exserophilum spp., Exophiala spp., Fonsecaea spp., Fulvia spp., Fusarium spp., Geotrichum spp., Guignardia spp., Helminthosporium spp., Histoplasma spp., Lecythophora spp., Macrophomina spp., Madurella spp., Magnaporthe spp., Malasseziafurfur, Microsporum spp., Monilinia spp., Mucor spp., *Mycocentrospora acerina*, Nectria spp., Nocardia spp., Oospora spp., Ophiobolus spp., Paecilomyces spp., *Paracoccidioides brasiliensis*, Penicillium spp., *Phaeosclera dematioides*, Phaeoannellomyces spp., Phialemonium obovatum, Phialophora spp., Phlyctaena spp., Phoma spp., Phomopsis spp., Phymatotrichum spp., Phytophthora spp., Pythium spp., *Piedraia hortai, Pneumocystis carinii*, Puccinia spp., *Pythium insidiosum, Rhinocladiella aquaspersa, Rhizomucor pusillus*, Rhizoctonia spp., Rhizopus spp., Saccharomyces spp., *Saksenaea vasiformis, Sarcinomyces phaeomuriformis*, Scerotium spp., Sclerotinia spp., Sphaerotheca spp., *Sporothrix schenckii, Syncephalastrum racemosum, Taeniolella boppii*, Taphrina spp., Thielaviopsis spp., Torulopsosis spp., Trichophyton spp., Trichosporon spp., *Ulocladium chartarum*, Ustilago spp., Venturia spp., Verticillium spp., *Wangiella dermatitidis*, Whetxelinia spp., Xylohypha spp., and their synonyms.

In another preferred embodiment, the compound is a toxic compound or is a compound that causes a toxic compound to be produced in the microorganism that forms following fusion. Preferably, the toxic compound is a toxin or fragment thereof selected from the group consisting of: diphtheria toxin, diphtheria toxin F2 fragment, diphtheria toxin A domain, Pseudomonas exotoxin A, and the A domain of Pseudomonas exotoxin A. Alternatively, the compound is a biosynthetic enzyme that causes a toxic compound to be produced in the microorganism that forms following fusion.

In a related embodiment, the second microorganism is resistant to the microcidal compound. In preferred embodiments, the second microorganism is a nonpathogenic fungus.

In a second aspect, the invention features a method for producing a diphtheria toxin-resistant fungus. The method includes introducing into the fungus a mutation in its DPH1, DPH3, or DPH4 gene that prevents the biosynthesis of diphthamide, wherein the fungus is selected from the group consisting of: Absidia spp., *Actinomadura madurae*, Actinomyces spp., *Allescheria boydii*, Altemaria spp., Anthopsis deltoidea, Aphanomyces spp., *Apophysomyces eleqans*, Armillaria spp., *Arnium leoporinum*, Aspergillus spp., *Aureobasidium pullulans, Basidiobolus ranarum*, Bipolaris spp., *Blastomyces dermatitidis*, Botrytis spp., Candida spp., Centrospora spp., Cephalosporium spp., Ceratocystis spp., Chaetoconidium spp., Chaetomium spp., Cladosporium spp., *Coccidioides immitis*, Colletotrichum spp, Conidiobolus spp., *Corynebacterium tenuis*, Cryptoporiopsis spp., Cylindrocladium spp., Cryptococcus spp., *Cunninghamella bertholletiae*, Curvularia spp., Dactylaria spp., Diplodia spp., Epidermophyton spp., *Epidermophyton floccosum*, Exserophilum spp., Exophiala spp., Fonsecaea spp., Fulvia spp., Fusarium spp., Geotrichum spp., Guignardia spp., Helminthosporium spp., Histoplasma spp., Lecythophora spp., Macrophomina spp., Madurella spp., Magnaporthe spp., *Malassezia furfur*, Microsporum spp., Monilinia spp., Mucor spp., *Mycocentrospora acerina*, Nectria spp., Nocardia spp., Oospora spp., Ophiobolus spp., Paecilomyces spp., *Paracoccidioides brasiliensis*, Penicillium spp., *Phaeosclera dematioides*, Phaeoannellomyces spp., *Phialemonium obovatum*, Phialophora spp., Phlyctaena spp., Phoma spp., Phomopsis spp., Phymatotrichum spp., Phytophthora spp., Pythium spp., *Piedraia hortai, Pneumocystis carinii*, Puccinia spp., *Pythium insidiosum, Rhinocladiella aquaspersa, Rhizomucor pusillus*, Rhizoctonia spp., Rhizopus spp., Saccharomyces spp., *Saksenaea vasiformis, Sarcinomyces phaeomuriformnis*, Scerotium spp., Sclerotinia spp., Sphaerotheca spp., *Sporothrix schenckii, Syncephalastrum racemosum, Taeniolella boppii*, Taphrina spp., Thielaviopsis spp., Torulopsosis spp., Trichophyton spp., Trichosporon spp., *Ulocladium chartarum*, Ustilago spp., Venturia spp., Verticillium spp., *Wangiella dermatitidis*, Whetxelinia spp., and Xylohypha spp.

In a third aspect, the invention features a diphtheria toxin-resistant fungus containing a mutation in its DPH1, DPH3, or DPH4 gene that prevents the biosynthesis of diphthamide, wherein the fungus is selected from the group consisting of: Absidia spp., *Actinomadura madurae*, Actinomyces spp., *Allescheria boydii*, Alternaria spp., *Anthopsis deltoidea*, Aphanomyces spp., *Apophysomyces eleqans*, Armillaria spp., *Arnium leoporinum*, Aspergillus spp., *Aureobasidium pullulans, Basidiobolus ranarum*, Bipolaris spp., *Blastomyces dermatitidis*, Botrytis spp., Candida spp., Centrospora spp., Cephalosporium spp., Ceratocystis spp., Chaetoconidium spp., Chaetomium spp., Cladosporium spp., *Coccidioides immitis*, Colletotrichum spp, Conidiobolus spp., *Corynebacterium tenuis*, Cryptoporiopsis spp., Cylindrocladium spp., Cryptococcus spp., *Cunninghamella bertholletiae*, Curvularia spp., Dactylaria spp., Diplodia spp., Epidermophyton spp., *Epidermophyton floccosum*, Exserophilum spp., Exophiala spp., Fonsecaea spp., Fulvia spp., Fusarium spp., Geotrichum spp., Guignardia spp., Helminthosporium spp., Histoplasma spp., Lecythophora spp., Macrophomina spp., Madurella spp., Magnaporthe spp., *Malassezia furfur*, Microsporum spp., Monilinia spp., Mucor spp., *Mycocentrospora acerina*, Nectria spp., Nocardia spp., Oospora spp., Ophiobolus spp., Paecilomyces spp., *Paracoccidioides brasiliensis*, Penicillium spp., Phaeosclera dematioides, Phaeoannellomyces spp., *Phialemonium obovatum*, Phialophora spp., Phlyctaena spp., Phoma spp., Phomopsis spp., Phymatotrichum spp., Phytophthora spp., Pythium spp., *Piedraia hortai, Pneumocystis carinii*, Puccinia spp., *Pythium insidiosum, Rhinocladiella aquaspersa, Rhizomucor pusillus*, Rhizoctonia spp., Rhizopus spp., Saccharomyces spp., *Saksenaea vasiformis, Sarcinomyces phaeomuriformis*, Scerotium spp., Sclerotinia spp., Sphaerotheca spp., *Sporothrix schenckii, Syncephalastrum racemosum, Taeniolella boppii*, Taphrina spp., Thielaviopsis spp., Torulopsosis spp., Trichophyton spp., Trichosporon spp., *Ulocladium chartarum*, Ustilago spp., Venturia spp., Verticillium spp., *Wangiella dermatitidis*, Whetxelinia spp., and Xylohypha spp. In a preferred embodiment of the second or third aspect, the gene hybridizes at high stringency to *S. cerevisiae* DPH1, DPH3, or DPH4 and has DPH activity.

In a fourth aspect, the invention features a substantially pure preparation of a Dph3 polypeptide.

In preferred embodiments, the Dph3 polypeptide is at least 55% identical to the amino acid sequence of FIG. 7 (SEQ ID No: 10), is from a fungus (e.g., *Saccharomyces cerevisiae*), and has DPH biological activity.

In a fifth aspect, the invention features DNA encoding a Dph3 polypeptide.

In preferred embodiments, the DNA includes the DPH3 gene of FIG. 7 (SEQ ID No: 9) and complements a DPH3 mutation in Saccharomyces cerevisiae.

By "fusion" is meant any combination of two organisms or cells that leads to the exchange, mixing, or transfer of intracellular contents. Preferred forms of fusion are mating and anastomosis.

By "kill" is meant to induce death in the microorganism that forms following fusion, resulting in a reduction in the number of microorganisms. Preferably, the reduction is at least 25%; more preferably the reduction is 50%; and most preferably the reduction in the number of microorganisms is 75% or even 95%.

By a "microcidal compound" is meant a molecule that leads to the induction of death of the microorganism. Exemplary microcidal compounds include, but are not limited to, molecules that are themselves toxic, molecules that induce production of a toxic compound, molecules that are toxic when combined with additional molecules, and DNA or RNA molecules encoding any of the foregoing molecules.

By "DPH biological activity" is meant an activity required for the biosynthesis of diphthamide; lack of said activity confers resistance to toxic compounds, including diphtheria toxin, diphtheria toxin F2 fragment, diphtheria toxin A domain, Pseudomonas exotoxin A, and the A domain of Pseudomonas exotoxin A.

By "polypeptide" is meant any chain of amino acids, regardless of length or post-translational modification (for example, glycosylation or phosphorylation).

By "high stringency conditions" is meant hybridization in 2× SSC at 40° C. with a DNA probe length of at least 40 nucleotides. For other definitions of high stringency conditions, see F. Ausubel et al., *Current Protocols in Molecular Biology*, pp. 6.3.1–6.3.6, John Wiley & Sons, New York, N.Y., 1994, hereby incorporated by reference.

By a "substantially pure polypeptide" is meant a polypeptide (for example, a polypeptide such as a Dph3 polypeptide) that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a Dph3 polypeptide. A substantially pure Dph3 polypeptide may be obtained, for example, by extraction from a natural source (for example, a fungal cell); by expression of a recombinant nucleic acid encoding a Dph3 polypeptide; or by chemically synthesizing the protein. Purity can be measured by any appropriate method, for example, column chromatography, polyacrylamide gel electrophoresis, or by HPLC analysis.

By "isolated DNA" is meant DNA that is free of the genes which, in the naturally-occurring genome of the organism from which the DNA of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA which is part of a hybrid gene encoding additional polypeptide sequence.

This invention provides significant advances over existing methods of controlling pathogenic microorganisms.

First, in contrast to chemical agents, this method is highly selective; only the target microorganism is eliminated and, thus, protective elements of the microbial ecosystem are left intact.

Second, unlike the application of "antagonistic" biocontrols to control post-harvest disease, the method of the invention actively kills target organisms and, thus, is expected to be more successful in eliminating established infections.

Third, unlike the use of hypoviruses to attenuate pathogenic strains of Cryphonectria parasitica (the causative agent of chestnut blight), the method described herein is broadly adaptable and can utilize a variety of toxic compounds and strains. It is not restricted by the identification of a suitable virus or the limited host-range of the infectious agent.

Finally, because mutation of DPH1, DPH2, DPH4, or DPH5 does not significantly affect cell growth, the killer organism is expected to grow robustly and perform well in the environment.

Other features and advantages of the invention will be apparent from the following description of the preferred embodiments thereof, and from the claims.

BRIEF DESCRIPTION OF THE DRAWINGS

FIG. 1 is a schematic representation of the present method, referred to as Mate and Die (MAD) technology.

FIGS. 3A–3E show the DNA sequence of a gene encoding EF-2 (EFT1) (SEQ ID No.: 1) and the encoded amino acid sequence of EF-2 protein (SEQ ID No.: 2), in which amino acid residue 699 (bold) is listed as a histidine. In the mature, toxin$^S$ protein, this histidine has been post-translationally modified by the DPH gene products to a diphthamide residue, the target of diphtheria toxin.

FIGS. 4A–4E show the DNA sequence of a gene encoding EF-2 (EFT2) (SEQ ID No.: 3) and the encoded amino acid sequence of EF-2 protein (SEQ ID No.: 4). Amino acid residue 699 (bold), listed as a histidine, is post-translationally modified as described in FIG. 3. The DNA of the EFT2 gene differs slightly from that of the EFT1 gene, but encodes an identical protein.

FIGS. 5A–5D show the DNA sequence of the DPHJ gene (SEQ ID No.: 5) and the resulting Dph1 amino acid sequence (SEQ ID No.: 6).

FIGS. 6A–6D show the DNA sequence of the DPH2 gene (SEQ ID No.: 7) and the resulting Dph2 amino acid sequence (SEQ ID No.: 8).

FIGS. 7A and 7B show the DNA sequence of the DPH3 gene (SEQ ID No.: 9) and the resulting Dph3 amino acid sequence (SEQ ID No.: 10).

FIGS. 8A and 8B show the DNA sequence of the DPH4 gene (SEQ ID No. 11) and the resulting Dph4 amino acid sequence (SEQ ID No.: 12).

FIGS. 9A–9C show the DNA sequence of the DPH5 gene (SEQ ID No.: 13) and the resulting Dph5 amino acid (SEQ ID No.: 14).

FIGS. 10A–10C show examples of structural homologs of DPH gene products. Analysis was performed February 1998 using the Capped BLAST datab ase search tool. Entries are organized by gene (DPH1, DPH2, DPH3, or DPH5), by database origin of the sequence (either annotated in GenBank or as an expressed sequence tag (EST), and the corresponding species from which it was isolated. Where available, the predicted size of the protein product is indicated a s well as the GenBank Accession number. Relative similarity is denoted by the "Score" corresponding to the probability (p value ) that the observed similarity could occur by random chance.

DETAILED DESCRIPTION OF THE INVENTION

Figure 2:
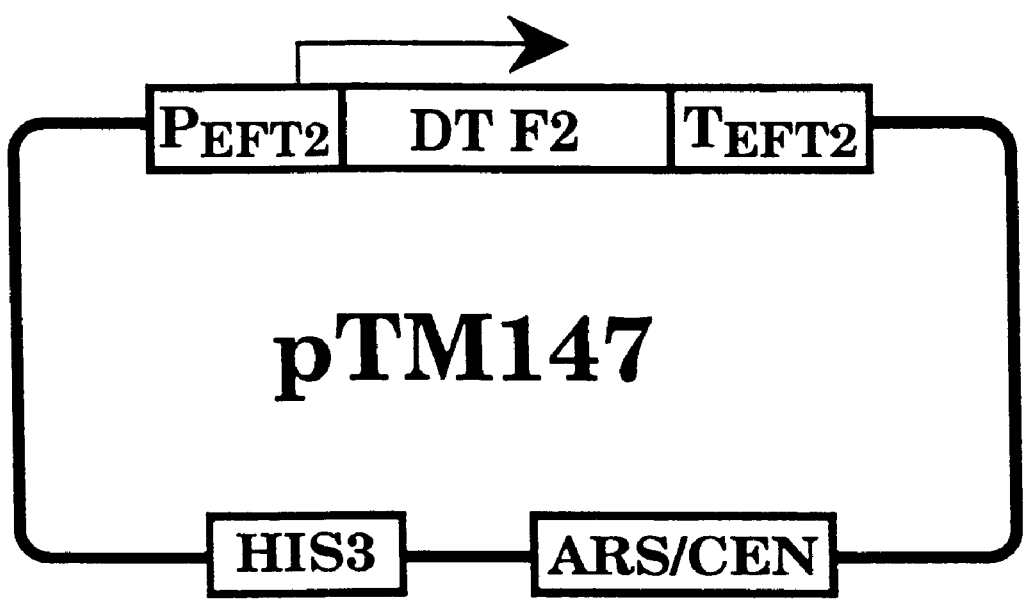
FIG. 2 is a schematic representation of plasmid pTM147, which expresses the diphtheria toxin F2 fragment (DT F2) under the control of the EFT2 promoter ($P_{EFT2}$) Transcription is indicated by the arrow and is terminated in the EFT2 transcription termination sequences ($T_{EFT2}$). ARS/CEN represents sequences for replication and segregation in yeast and HIS3 represents a selectable auxotrophic marker. Also present (but not shown) are sequences enabling replication in E. coli.

We have discovered methods of biological control that (i) selectively target a microorganism that has an undesirable attribute; and (ii) introduce into the target microorganism a compound (e.g., a protein, peptide, DNA, or RNA) that kills the cell that forms following fusion. Undesirable attributes include pathogenicity and excessive or unwanted growth.

The present invention provides a method of selectively delivering a microcidal compound into a target microorganism, such as a bacterium or fungus, by fuising the target microorganism with a second microorganism. The second microorganism is referred to as a killer microorganism, as the delivered microcidal compound kills the microorganism that forms following the fusion.

The killer microorganism has been altered in two key respects. First, it has been altered so that it expresses the toxic compound or a product, such as a biosynthetic enzyme, which will make a toxic compound in the microorganism. Toxic compounds include compounds that are themselves toxic (e.g., bacterial toxins) or result in the production of a toxic compound (e.g., a biosynthetic enzyme which causes production of a toxic compound) in the microorganism. DNA or RNA encoding the toxic compound can be introduced into the killer microorganism (or an ancestor) either extrachromosomally (e.g., in a plasmid) or stably integrated into chromosomal DNA. In either case, the toxic compound is expressed in the killer microorganism.

Second, the killer microorganism has been modified in such a manner that it is resistant to the toxic compound. This is done, for example, by mutating or deleting all or a portion of a gene(s) which renders the wild-type or unmodified microorganism sensitive to the toxic compound. As a result, the modified microorganism is itself resistant to its effects.

For certain uses, the killer strain is also altered in such a manner that it does not exhibit the undesirable characteristic (e.g., pathogenicity, rapid or unwanted growth) of the target microorganism. Alternatively, a nonpathogenic microorganism (nonpathogenic wild-type) which undergoes fusion with the target microorganism can be used as a progenitor for the killer microorganism.

In various embodiments of the present method, the target microorganism is a fungus, such as Absidia spp., *Actinomadura madurae*, Actinomyces spp., *Allescheria boydii*, Altemaria spp., *Anthopsis deltoidea*, Aphanomyces spp., *Apophysomyces eleqans*, Armillaria spp., *Arnium leoporinum*, Aspergillus spp., *Aureobasidium pullulans*, *Basidiobolus ranarum*, Bipolaris spp., *Blastomyces dermatitidis*, Botrytis spp., Candida spp., Centrospora spp., Cephalosporium spp., Ceratocystis spp., Chaetoconidium spp., Chaetomium spp., Cladosporium spp., *Coccidioides immitis*, Colletotrichum spp, Conidiobolus spp., *Corynebacterium tenuis*, Cryptoporiopsis spp., Cylindrocladium spp., Cryptococcus spp., *Cunninghamella bertholletiae*, Curvularia spp., Dactylaria spp., Diplodia spp., Epidermophyton spp., *Epidernophyton floccosum*, Exserophilum spp., Exophiala spp., Fonsecaea spp., Fulvia spp., Fusarium spp., Geotrichum spp., Guignardia spp., Helminthosporium spp., Histoplasma spp., Lecythophora spp., Macrophomina spp., Madurella spp., Magnaporthe spp., *Malassezia furfur*, Microsporum spp., Monilinia spp., Mucor spp., *Mycocentrospora acerina*, Nectria spp., Nocardia spp., Oospora spp., Ophiobolus spp., Paecilomyces spp., *Paracoccidioides brasiliensis*, Penicillium spp., *Phaeosclera dematioides*, Phaeoannellomyces spp., *Phialemonium obovatum*, Phialophora spp., Phlyctaena spp., Phoma spp., Phomopsis spp., Phymatotrichum spp., Phytophthora spp., Pythium spp., *Piedraia hortai, Pneumocystis carinii*, Puccinia spp., *Pythium insidiosum, Rhinocladiella aquaspersa, Rhizomucor pusillus*, Rhizoctonia spp., Rhizopus spp., Saccharomyces spp., *Saksenaea vasiformis, Sarcinomyces phaeomuriformis*, Scerotium spp., Sclerotinia spp., Sphaerotheca spp., *Sporothrix schenckii, Syncephalastrum racemosum*, Taeniolella boppii, Taphrina spp., Thielaviopsis spp., Torulopsosis spp., Trichophyton spp., Trichosporon spp., *Ulocladium chartarum*, Ustilago spp., Venturia spp., Verticillium spp., *Wangiella dermatitidis*, Whetxelinia spp., and Xylohypha spp. The method is particularly applicable to organisms that (i) are predominantly of a single mating type in their pathogenic forms (e.g., *Cryptococcus neoformans, Histoplasma capsulatum*); (ii) require fusion for pathogenesis (e.g., smuts such as *Ustilago maydis*); (iii) outbreed at high frequency (e.g., powdery mildews); or (iv) have limited numbers of VCGs (e.g., *Fusarium circinatum*).

According to the method described herein, the toxic compound expressed in the killer strain diffuses to and makes contact with components of the target microorganism which are sensitive to it (inactivated or otherwise rendered nonfunctional). At the same time, the cytoplasm of the target cell can furnish the means (e.g., the enzymatic machinery) necessary to render the killer strain sensitive to the toxic compound. As a result of the mating or fusion, the toxic compound inhibits a process or processes (e.g., protein synthesis) essential for viability/growth of the fused cells (e.g., the fused zygote) and cell death occurs.

Killer Strain Properties

A key element in this invention is the use of the natural physiology of the killer strain, and its propensity to undergo fusion, as a means to destroy or inactivate the target (e.g., pathogenic) species. Therefore, the spectrum of antimicrobial activity is determined by the physiology of the killer and target strains and the conditions and determinants that regulate the selection of partners and orchestration of the mating and/or fusion event (including mating type and VCG). In some circumstances, these determinants may be undesirably restrictive (e.g., the presence of many VCGs in pathogenic strains). Therefore, it may be desirable to develop killer strains that tolerate differences at one or more incompatibility loci (for instance, the tol mutants of *Neurospora tetrasperma*).

It is desirable that the toxic compounds are unable to cross cellular membranes or are able to do so only to a very limited extent, in order that the killer strain is substantially non-toxic if consumed, lysed, or ingested. The toxins act intracellularly. As a result, with cell-impermeable toxic compounds, the only means of toxin entry into a cell would be upon fusion. The cell death that results from the transfer of the toxic compound is not necessarily restricted to the site of the cell fusion, however, as the hyphae of many filamentous fungi are characterized by pores in the septae that allow transport of molecules among hyphal cells. Therefore, by using a toxin (such as diphtheria toxin) that is very stable and acts catalytically, it is possible to kill entire hyphal filaments as a consequence of a single fusion event.

For application as a biological control agent, it is also desirable that the killer strain be engineered or attenuated such that it is itself non-pathogenic. This enables the treatment of an infected plant or organism with an excess of killer strain relative to the pathogen. Killer cells that undergo fusion with their pathogenic counterparts will be killed or inactivated. Killer cells that do not undergo fusion, or do so with another killer cell, will persist in a non-pathogenic form, growing superficially and awaiting challenge by toxin-sensitive pathogenic strains.

Microcidal Compounds

The microcidal compound in the killer strain can be any of a variety of toxic products (e.g., enzymes, proteins, small molecules) which act intracellularly. Preferably, the toxic compounds cross cellular membranes only to a limited extent or not at all. Toxic compounds which can be produced by killer cells include diphtheria toxin, diphtheria toxin F2 fragment, diphtheria toxin A domain, Pseudomonas exotoxin A, or the A domain of Pseudomonas exotoxin A. They can be expressed individually in killer cells or two or more can be expressed. DNA or RNA encoding the toxic compound(s) is introduced into an appropriately modified wild-type cell, using known methods. For example, it can be incorporated into an expression vector, such as a plasmid, which is introduced into a microorganism to produce a killer strain. In this case, introduced DNA or RNA is expressed extrachromosomally. Alternatively, the introduced DNA is incorporated into the genomic DNA of the recipient. This can be carried out, for example, by means of a vector that introduces toxic compound-encoding DNA into host cell genomic DNA through homologous, non-homologous, or site specific recombination. As a result, DNA directing synthesis the toxic compound is maintained as part of the genome.

Applications of the Method

The method, killer cells, and toxin resistant strains of the present invention have broad applicability to any microorganism that undergoes fusion. They are also broadly applicable to a wide variety of contexts in which selective biological control of microorganisms is desired. For example, potential applications include, but are not limited to: prophylactic or retroactive treatment of microbial infections of agricultural crops (e.g. corn, rice, rubber, tobacco, etc.) or ornamental trees (e.g., elm, chestnut); prevention of the post-harvest colonization of fruits and vegetables by microbes that cause rotting or other damage; prophylactic or retroactive treatment of ventilation units to eliminate microorganisms that produce volatile organic compounds (VOCs) implicated in "sick building" syndrome; and treatment of humans, pets or livestock colonized or infected by microorganisms, particularly pathogenic forms of a microorganism.

The present invention is illustrated by the following examples, which is not intended to be limiting in any way.

EXAMPLE 1

In this embodiment, the killer strain is a yeast strain of the opposite mating type from that of the target yeast. The killer strain has been modified such that it expresses a toxic compound, is resistant to the toxic compound and is non-pathogenic. For example, the killer strain is engineered to produce a toxic molecule (e.g., diphtheria toxin, diphtheria toxin F2 fragment, diphtheria toxin A domain, Pseudomonas exotoxin A, or the A domain of Pseudomonas exotoxin A) and to be resistant to the toxin. The killer strain can be rendered resistant by deletion of a gene required for biosynthesis of diphthamide, the intracellular target of diphtheria toxin.

In this case, diphtheria toxin resistant mutants were isolated by selecting for yeast strains that were viable when expressing diphtheria toxin under a regulated promoter (GAL-DT). Mutations were identified in a total of five genes that blocked the biosynthesis of diphthamide (FIGS. 5–9). Three of these genes (DPK1, DPH3, and DPH4) were previously uncharacterized and, thus, were not known to be involved in diphthamide biosynthesis. Additionally, prior to this work, DPH3 had not been recognized as a potential protein coding sequence due to its small size (246 bp ORF encoding a predicted protein product of 82 amino acids). Strains with mutations in any of the DPH genes (including the three novel genes identified herein) enable the non-toxic intracellular expression of diphtheria toxin suitable for the methods described herein, as well as for other applications.

In the specific example, DNA sequences encoding the DPK1 gene were replaced with the TRP1 marker DNA to generate a dph1::TRP1 strain. This strain does not make diphthamide, and is viable and can be propagated even while expressing diphtheria toxin. The target yeast and the killer yeast are combined or contacted with one another, whereby they undergo fusion. Subsequently, nuclei also fuse to generate a diploid organism with a genome reflecting the sum of each of the two mating partners. As a result of the initial cell fusion, toxin contained within the cytoplasm of the killer strain diffuses to, and enzymatically inactivates, toxin sensitive components of the target cell. In the provided example with diphtheria toxin, the toxin ADP-ribosylates translation elongation factor 2 (EF-2) on a diphthamide residue to inactivate the protein and consequently block protein synthesis. At the same time, the cytoplasm of the target cell furnishes the enzymatic machinery to synthesize diphthamide on the toxin-resistant EF-2 of the killer cell to convert it into a toxin-sensitive form. As a result of the mating reaction, the toxin inhibits protein synthesis in the microorganism formed following fusion, causing cessation of growth of this fused, resultant zygote and ultimately cell death.

EXAMPLE 2

The following are experiments performed in S. cerevisiae. Analogous modifications can be performed in any microorganism, using analogous genes and standard methods.

Toxin Expression

The diphtheria toxin F2 fragment contains the catalytic activity of diphtheria toxin and thus is sufficient to catalyze the ADP-ribosylation of the diphthamide residue of translation elongation factor 2 (EF-2). The F2 fragment lacks the determinants for binding to cell surface receptors and for translocating across cellular membranes. The DNA sequence encoding this fragment was inserted between the transcriptional initiation and termination regions of the EFT2 gene (FIG. 2). This allows high level, constitutive transcription of the DNA sequence corresponding to the F2 fragment and the subsequent translation into active F2 protein. In this particular case, this EFT2-DT-EFT2 fusion was introduced into a plasmid vector that allows extrachromosomal replication in yeast (pRS313). For construction of a biological control agent, this fusion might preferably be integrated into the genome of the killer strain such that it is more stably maintained.

Toxin Resistance

Diphtheria toxin specifically catalyzes the ADP-ribosylation of EF-2 on a diphthamide residue. Diphthamide is a unique post-translationally modified amino acid residue found only in EF-2. Mutants that fail to make diphthamide or lack the histidine precursor of diphthamide are resistant to toxin. Therefore, mutations in any one of seven or more genes is sufficient to provide resistance to diphtheria toxin. These are the genes encoding EF-2 (two genes), Dph1, Dph2, Dph3, Dph4, and Dph5. The sequences of these genes are displayed in FIGS. 3–9. Deletion of any one of the DPH genes is sufficient to yield nearly complete resistance to diphtheria toxin. The toxin resistant phenotype is completely recessive such that strains that carry at least one functional copy of a given DPH gene are toxin-sensitive regardless of the number of mutant or deleted copies. In contrast, mutations in the genes encoding EF-2 (EFT1 and EFT2) that confer toxin resistance, generally behave in a dominant fashion and, thus, are less useful for construction of an effective killer strain. Strains mutant or deleted for DPH3 exhibit pleiotropic growth defects, including but not limited to slow growth, hypersensitivity to a variety of drugs, and defects in invasion of an agar substrate. The pleiotropic and significant defects of dph3 mutant strains make this an excellent candidate mutation for a killer strain as it simultaneously provides resistance to toxin while attenuating cellular vitality and several growth characteristics of pathogenic organisms (e.g., substrate invasion). Alternatively, it was found that mutations in DPH1, DPH2, DPH4, or DPH5 impair the ability of the organism to survive long periods of starvation. While mutations in the latter group of genes are not sufficient to attenuate the pathogenesis of the killer strain alone, they may be useful to effectively limit the persistence of the killer strain in the environment. The dph1, dph2, dph4, and dph5 mutations do not significantly impair the growth and mating of the microorganism, and, thus, would be expected to perform well in the environment. The sequences displayed in FIGS. 3–9 detail S. cerevisiae genes that can be mutated to give diphtheria toxin resistance. Additionally, analysis of DNA sequence databases reveals the clear presence of genes in a variety of organisms that are structurally, and presumably functionally, related (FIGS. 10A–10C).

Construction and Mating of Killer and Target Strains

Prototypical killer and target strains were constructed in *S. cerevisiae*. The killer strain, TMY401 (MATa dph1::TPRP1 ura3-52 leu2-3,112 his3-11,15 trp1-1 ade2-1) was transformed with pTM147 (EFT2:DT:EFT2 HIS3 CEN). This strain is also His+ as a result of the HIS3 marker of pTM147. TMY407 <pRS426>was selected as a sample target strain. It was constructed by transforming TMY407 (MATα ura3-52 leu2-3, 112 his3-11,15 trp1 63 ade2-1) with pRS426 (2 μ URA3) which confers uracil prototrophy.

Killer and target strains were patched to SC-His and SC-Ura media, respectively and grown overnight at 30° C. The killer and target strains were mixed and allowed to mate (i.e., undergo fusion) by transferring them (by replica plating) to rich media (YPD). After incubation overnight at 30° C., mating mixtures were then transferred to media (SC-Ura, His) that selects for growth of the mated diploids. Diploids appear on these plates as growing patches (many colonies) at the intersection of the two mating partners. Neither of the haploid mating partners will grow on the SC-Ura, His plates as a result of either Ura or His auxotrophies.

Figure 11:
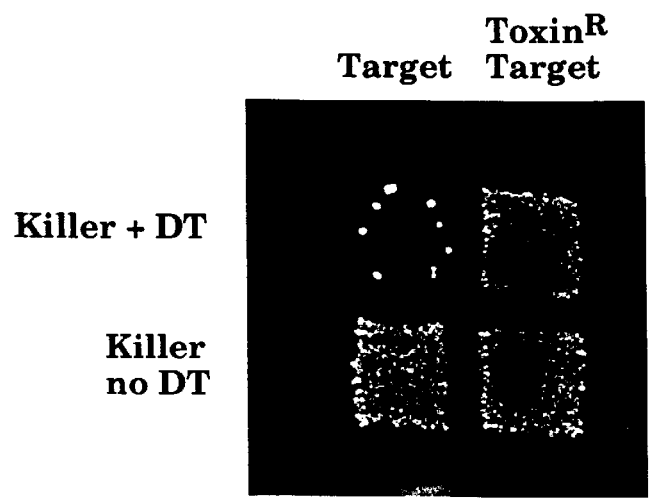
FIG. 11 is a photograph of results of mating a killer strain expressing diphtheria toxin (DT; Killer+DT) with a target strain (Target) and of matings between either the target and a killer strain that does not express toxin (Killer no DT); the toxin-expressing killer strain (Killer+DT) and a toxin$^R$ derivative of the target (Toxin$_R$Target); or the toxic$_R$ derivative of the target (Toxin$_R$Target) and a killer strain that does not express toxin (Killer no DT).

As is illustrated in FIG. 11, very few viable diploids appear at the intersection of the killer and target strains. In contrast, if the killer strain is mated with a Ura+ strain that is resistant to diphtheria toxin, TMY403(MATα dph1::TRP1 ura3-52 leu2-3,112 his3-11,15 trp1-1 ade2-1<HIS3 CEN>), healthy diploids are readily obtained.

Production of diphtheria toxin-resistant fungi

It is possible to isolate fingi that are resistant to toxin and, thus, are usefull as killer strains. In one example, following isolation of any specific homolog of a *S. cerevisiae* DPH gene from another fuingus, one can engineer this second fungus to be a killer strain by introducing a mutation into the homologous gene. Mutating any such gene is likely to make the fungus diphtheria toxin-resistant. Alternatively, one can use the selection described herein to isolate toxin-resistant strains. These strains are likely to contain a mutation in one of the DPH genes described herein, including genes that are homologous to DPH1, DPH3, and DPH4.

Genetic engineering methods, including transformation and homologous recombination techniques, are practiced in many fingi (Punt and van den Hondel, Methods Enzymol. 1992, 216:447–457; Timberlake and Marshall, Science, 1989, 244:1313–1317; Fincham, Microbiol Rev. 1989, 53:148–170). Gene deletion techniques are currently practiced in many fungi, including, but not limited to, *Candida albicans* (Fonzi and Irwin, Genetics 1993, 134: 717–728), *Ustilago maydis* (Fotheringham and Hollman, Mol. Cell Biol. 1989, 9:4052–4055; Bolker et al., Mol. Gen. Genet. 1995, 248:547–552), *Yarrowia lipolytica* (Neuveglise et al., Gene 1998, 213:37–46; Chen et al., Appl. Microbiol. Biotechnol. 1997, 48:232–235; Cordero et al., Appl. Microbiol. Biotechnol. 1996, 46:143–148), *Acremonium chrysogenum* (Skatrud et al., Curr. Genet. 1987, 12:337–348; Walz and Kuck, Curr. Genet. 1993, 24:421–427), *Magnaporthe grisea* (Sweigard et al., Mol. Gen. Genet. 1992, 232:183–190); Kershaw et al., EMBO J. 1998, 17:3838–3849), *Histoplasma capsulatum* (Woods et al., J. Bacteriol. 1998, 180:5135–5143) and Aspergillus sp. (Miller et al., Mol. Cell Biol. 1985, 5:1714–1721; de Ruiter-Jacobs et al., Curr. Genet. 1989, 16:159–163; Gouka et al., Curr. Genet. 1995, 27:536–540; van den Hombergh et al., Mol. Gen. Genet. 1996, 251:542–550; D'Enfert, Curr. Genet. 1996, 30:76–82; Weidner et al., Curr. Genet. 1998, 33:378–385).

Other Embodiments

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

SEQUENCE LISTING

```
<160> NUMBER OF SEQ ID NOS: 14

<210> SEQ ID NO 1
<211> LENGTH: 3733
<212> TYPE: DNA
<213> ORGANISM: Saccharomyces cerevisiae

<400> SEQUENCE: 1
tacgtatata aagtagaaaa ttcatacctt tgaacaaggt gatctttttc ctttagttga     60
tattaatccc gggtaaactt ccgtgttgca cttttaaaat ttttttttcaa atctcaccta    120 gaaaattttt ttttgccatg agccttcctt taattaatct caattgcata ctactgttgt    180
attaaacgct tcactggttt ttttacttaa ccccatttgc cagaaagcca gacctacgca    240
cccaagaatt tttaataaca gataaaaatg gttgctttca ctgttgacca aatgcgttct    300
ttaatggaca aagttaccaa tgtgcgtaac atgtccgtta ttgctcacgt cgatcatggt    360
aagtccactt tgaccgattc cttggtccaa agagccggta ttatttccgc tgctaaggct    420
ggtgaagctc gtttcaccga taccagaaag gatgaacaag aaagaggtat cactatcaag    480
```

-continued

```
tctaccgcta tttctctata ctctgaaatg tctgacgaag atgtcaagga aatcaagcaa    540
aagaccgacg gtaactcctt cttgatcaac ttgatcgact ctccaggtca cgttgacttc    600
tcctctgaag ttactgccgc tttacgtgtc actgacggtg ctttggttgt cgtcgacacc    660
attgaaggtg tctgtgtcca aaccgaaact gttttgagac aagctttggg tgaaagaatc    720
aagcctgttg ttgttatcaa caaggtcgac agagctttgt tggaattgca agtttctaag    780
gaagatttat accaaaacctt tgccagaact gttgaatccg ttaacgtcat cgtttccacc    840
tacgccgatg aagtttttggg tgatgtccaa gtttacccag ccagaggtac cgttgccttc    900
ggttccggtt tgcacggttg ggctttcact atccgtcaat cgccaccag atatgctaag     960 aaattcggtg tcgacaaggc caagatgatg gacagattat ggggtgactc tttcttcaac   1020
ccaaagacca agaagtggac caacaaggac actgatgctg aaggtaagcc attggaaaga   1080
gctttcaaca tgttcatctt ggacccaatc ttcagattat tcactgctat catgaacttc   1140
aagaaagacg aaattccagt tttgctagaa aagttggaaa ttgtcttgaa gggtgacgaa   1200
aaggacttgg aaggtaaggc cttgttgaag gttgttatga aaagttctt gccagctgcc   1260 gatgccttat tggaaatgat tgtcttgcac ttgccatctc cagtcactgc tcaagcctac   1320
agagctgaac aattatacga aggtccagct gacgatgcca actgtattgc tatcaagaac   1380
tgtgatccaa aggctgattt gatgttgtac gtctccaaga tggtgccaac ctctgataag   1440
ggtagattct acgccttcgg tagagttttt gccggtactg ttaagtccgg tcaaaaggtc   1500
agaatccaag gtccaaacta cgttccaggt aagaaggacg atttgttcat caaggccatt   1560
caaagagttg ttttgatgat gggtagattt gtcgaaccaa tcgatgactg tccagccggt   1620
aacattatcg gtttagtcgg tatcgatcaa ttcttgttga agactggtac tttgaccacc   1680
agtgaaactg ctcacaacat gaaggtcatg aaattctctg tctctccagt tgtgcaagtc   1740
gctgtcgaag tcaagaacgc taacgactta ccaaaattgg tcgaaggttt gaagagattg   1800
tccaagtctg atccatgtgt cttgacctat atgtctgaat ccggtgaaca tatcgttgct   1860
ggtaccggtg aattgcattt ggaaatttgt ttgcaagatt tggaacacga ccacgctggt   1920
gttccattga agatctcccc accagttgtc gcttacagag aaactgttga agtgaatct    1980 tctcaaactg ctttgtccaa gtctccaaac aagcataaca gaatctactt gaaggctgaa   2040
ccaattgacg aagaagtctc tttggctatt gaaaacggta tcatcaaccc aagagatgat   2100
ttcaaggcca gagctagaat catggctgac gactacggtt gggatgtcac cgatgccaga   2160
aagatctggt gtttcggtcc agacggtaac ggtccaaact tggttattga ccaaactaag   2220
gctgtccaat acttgcacga aatcaaggat tccgttgttg ctgctttcca atgggctacc   2280
aaggaaggtc caattttcgg tgaagaaatg agatctgtca gagttaacat tttggatgtt   2340
actttacatg ccgatgctat ccacagaggt ggtggtcaaa tcatcccaac catgagaaga   2400
gctacttacg ccggtttctt gttggctgat ccaaagatcc aagaaccagt tttcttggtc   2460
gaaattcaat gtccagaaca agccgtcggt ggtatctact ccgtcttaaa caagaagaga   2520
ggtcaagtcg tttctgaaga acaaagacca ggtactccat gtttaccgt caaggcctac    2580 ttgccagtta acgaatcttt cggtttcact ggtgaattga caagctac cggtggtcaa     2640 gctttcccac aaatggtttt cgaccattgg tccactttag gttctgaccc attggaccca   2700
acctctaagg ctggtgaaat tgttcttgct gctcgtaaga gacacggtat gaaggaagaa   2760
gttccaggct ggcaagaata ttacgacaaa ttgtaagaag tctaaatgag aaaaggtggt   2820
tctgtaagag caaaccttac cgccttatga tcttttttcat ttattctctg ctttaaaatt   2880
```

-continued

```
ttgtcgtaat aaaaatagta tggtaataga cttatatatt attttcttac acattttttgt    2940 catatagtta tattccgaat gtttacaatc gaacccatca taaaaatgga ccttttcgta    3000
ttaccgcccc ctttgtagag ggggaggaac ggcaacttct tgactattac gacgtatcac    3060 cacccccgtta gatatactat ggaaaaaact attaaaaacc attataattc attaatgaca    3120
tcggtcctga ggtagtatta cgtataactt acctggctct tggtcatagc tttttatccg    3180
tttacgaaaa aaggagaaga agattgggct tccgcggcta ttgtttggtt tatacccccgc    3240 cgtatgttgg tgcttctata attagagcga aataggaaat acaaaaaatc cttggagggg    3300
aggaccagcc tcatcgggct aaaactccct caaaaccgga ggggcaacca agtatatat    3360 ctcattatgg ccgatacttc tagaggcgca ctaacagaag cacctcagcc cctgcaggtg    3420
aaagaaagag gtaattaatt ttccggttac ttactttctc tcgctattgg ggaaagcgtt    3480
ggttcgaggc gttgaggtcg aagacaatca ttgttttctt cttatttaag tacatcttta    3540
gaagaaaatt acacaactgg aatgagtaaa tcaatacttg ctttgtgttc ccattgttag    3600
atactcttgt tttagcatgt gatagcagta tataatataa cctgcaaaat aatcgaaacg    3660
cgtacacagg aaagagtaca taaataacca tagtatattt ctggacatat cttattacac    3720
aacataaaat aga                                                      3733
```

<210> SEQ ID NO 2
<211> LENGTH: 842
<212> TYPE: PRT
<213> ORGANISM: Saccharomyces cerevisiae

<400> SEQUENCE: 2

```
Met Val Ala Phe Thr Val Asp Gln Met Arg Ser Leu Met Asp Lys Val
 1               5                  10                  15

Thr Asn Val Arg Asn Met Ser Val Ile Ala His Val Asp His Gly Lys
            20                  25                  30

Ser Thr Leu Thr Asp Ser Leu Val Gln Arg Ala Gly Ile Ile Ser Ala
        35                  40                  45

Ala Lys Ala Gly Glu Ala Arg Phe Thr Asp Thr Arg Lys Asp Glu Gln
    50                  55                  60

Glu Arg Gly Ile Thr Ile Lys Ser Thr Ala Ile Ser Leu Tyr Ser Glu
 65                  70                  75                  80

Met Ser Asp Glu Asp Val Lys Glu Ile Lys Gln Lys Thr Asp Gly Asn
                85                  90                  95

Ser Phe Leu Ile Asn Leu Ile Asp Ser Pro Gly His Val Asp Phe Ser
            100                 105                 110

Ser Glu Val Thr Ala Ala Leu Arg Val Thr Asp Gly Ala Leu Val Val
        115                 120                 125

Val Asp Thr Ile Glu Gly Val Cys Val Gln Thr Glu Thr Val Leu Arg
    130                 135                 140

Gln Ala Leu Gly Glu Arg Ile Lys Pro Val Val Ile Asn Lys Val
145                 150                 155                 160

Asp Arg Ala Leu Leu Glu Leu Gln Val Ser Lys Glu Asp Leu Tyr Gln
                165                 170                 175

Thr Phe Ala Arg Thr Val Glu Ser Val Asn Val Ile Val Ser Thr Tyr
            180                 185                 190

Ala Asp Glu Val Leu Gly Asp Val Gln Val Tyr Pro Ala Arg Gly Thr
        195                 200                 205

Val Ala Phe Gly Ser Gly Leu His Gly Trp Ala Phe Thr Ile Arg Gln
```

```
            210                 215                 220
Phe Ala Thr Arg Tyr Ala Lys Lys Phe Gly Val Asp Lys Ala Lys Met
225                 230                 235                 240

Met Asp Arg Leu Trp Gly Asp Ser Phe Asn Pro Lys Thr Lys Lys
                245                 250                 255

Trp Thr Asn Lys Asp Thr Asp Ala Glu Gly Lys Pro Leu Glu Arg Ala
                260                 265                 270

Phe Asn Met Phe Ile Leu Asp Pro Ile Phe Arg Leu Phe Thr Ala Ile
                275                 280                 285

Met Asn Phe Lys Lys Asp Glu Ile Pro Val Leu Leu Glu Lys Leu Glu
            290                 295                 300

Ile Val Leu Lys Gly Asp Glu Lys Asp Leu Glu Gly Lys Ala Leu Leu
305                 310                 315                 320

Lys Val Val Met Arg Lys Phe Leu Pro Ala Ala Asp Ala Leu Leu Glu
                325                 330                 335

Met Ile Val Leu His Leu Pro Ser Pro Val Thr Ala Gln Ala Tyr Arg
                340                 345                 350

Ala Glu Gln Leu Tyr Glu Gly Pro Ala Asp Asp Ala Asn Cys Ile Ala
            355                 360                 365

Ile Lys Asn Cys Asp Pro Lys Ala Asp Leu Met Leu Tyr Val Ser Lys
370                 375                 380

Met Val Pro Thr Ser Asp Lys Gly Arg Phe Tyr Ala Phe Gly Arg Val
385                 390                 395                 400

Phe Ala Gly Thr Val Lys Ser Gly Gln Lys Val Arg Ile Gln Gly Pro
                405                 410                 415

Asn Tyr Val Pro Gly Lys Asp Asp Leu Phe Ile Lys Ala Ile Gln
                420                 425                 430

Arg Val Val Leu Met Met Gly Arg Phe Val Glu Pro Ile Asp Asp Cys
                435                 440                 445

Pro Ala Gly Asn Ile Ile Gly Leu Val Gly Ile Asp Gln Phe Leu Leu
            450                 455                 460

Lys Thr Gly Thr Leu Thr Thr Ser Glu Thr Ala His Asn Met Lys Val
465                 470                 475                 480

Met Lys Phe Ser Val Ser Pro Val Val Gln Val Ala Val Glu Val Lys
                485                 490                 495

Asn Ala Asn Asp Leu Pro Lys Leu Val Glu Gly Leu Lys Arg Leu Ser
            500                 505                 510

Lys Ser Asp Pro Cys Val Leu Thr Tyr Met Ser Glu Ser Gly Glu His
            515                 520                 525

Ile Val Ala Gly Thr Gly Glu Leu His Leu Glu Ile Cys Leu Gln Asp
            530                 535                 540

Leu Glu His Asp His Ala Gly Val Pro Leu Lys Ile Ser Pro Pro Val
545                 550                 555                 560

Val Ala Tyr Arg Glu Thr Val Glu Ser Glu Ser Ser Gln Thr Ala Leu
                565                 570                 575

Ser Lys Ser Pro Asn Lys His Asn Arg Ile Tyr Leu Lys Ala Glu Pro
                580                 585                 590

Ile Asp Glu Glu Val Ser Leu Ala Ile Glu Asn Gly Ile Ile Asn Pro
            595                 600                 605

Arg Asp Asp Phe Lys Ala Arg Ala Arg Ile Met Ala Asp Asp Tyr Gly
            610                 615                 620

Trp Asp Val Thr Asp Ala Arg Lys Ile Trp Cys Phe Gly Pro Asp Gly
625                 630                 635                 640
```

-continued

```
Asn Gly Pro Asn Leu Val Ile Asp Gln Thr Lys Ala Val Gln Tyr Leu
            645                 650                 655
His Glu Ile Lys Asp Ser Val Val Ala Ala Phe Gln Trp Ala Thr Lys
        660                 665                 670
Glu Gly Pro Ile Phe Gly Glu Met Arg Ser Val Arg Val Asn Ile
    675                 680                 685
Leu Asp Val Thr Leu His Ala Asp Ala Ile His Arg Gly Gly Gln
690                 695                 700
Ile Ile Pro Thr Met Arg Arg Ala Thr Tyr Ala Gly Phe Leu Leu Ala
705                 710                 715                 720
Asp Pro Lys Ile Gln Glu Pro Val Phe Leu Val Glu Ile Gln Cys Pro
                725                 730                 735
Glu Gln Ala Val Gly Gly Ile Tyr Ser Val Leu Asn Lys Lys Arg Gly
            740                 745                 750
Gln Val Val Ser Glu Glu Gln Arg Pro Gly Thr Pro Leu Phe Thr Val
        755                 760                 765
Lys Ala Tyr Leu Pro Val Asn Glu Ser Phe Gly Phe Thr Gly Glu Leu
770                 775                 780
Arg Gln Ala Thr Gly Gly Gln Ala Phe Pro Gln Met Val Phe Asp His
785                 790                 795                 800
Trp Ser Thr Leu Gly Ser Asp Pro Leu Asp Pro Thr Ser Lys Ala Gly
                805                 810                 815
Glu Ile Val Leu Ala Ala Arg Lys Arg His Gly Met Lys Glu Glu Val
            820                 825                 830
Pro Gly Trp Gln Glu Tyr Tyr Asp Lys Leu
        835                 840
```

<210> SEQ ID NO 3
<211> LENGTH: 3457
<212> TYPE: DNA
<213> ORGANISM: Saccharomyces cerevisiae

<400> SEQUENCE: 3

```
aacgatatgg agaattcaaa atgggtgcga aatacctgga acgtaagcgt tctgagaaat    60
acacagacgc attaacctga caaaaacaca actagtttgg gaaagggatt tggtcttttcc  120
tctcgggtct ctcgtgtggt tcctttcttt ctcagatctc cctgcacact gggctgttgt   180
cctccaggtt atggtttgtt ctcttcaggt attacaatgc agtaggcttt tggagtgagc   240
aaaacgaaga gagaaaaaaa ttttttctta aaagtttttt ttcattttgt gagcttattc   300
ttcttttcta tatattcttg atatcttaga ttatacatat tattctctta catttcacga   360
ttgccctttt ggtgtttagc attcagactc aaagaccaca aacacaaact ataacataat   420
tgcaagatgg ttgctttcac tgttgaccaa atgcgttctt taatgacaa agttaccaat    480
gtgcgtaaca tgtccgttat tgctcacgtc gatcatggta agtccacttt gaccgattcc   540
ttggtccaaa gagccggtat tatttccgct gctaaggctg gtgaagctcg tttcaccgat   600
accagaaagg atgaacaaga aagaggtatc actatcaagt ctaccgctat ttctctatac   660
tctgaaatgt ctgacgaaga tgtcaaggaa atcaagcaaa agaccgacgg taactccttc   720
ttgatcaact tgatcgactc tccaggtcac gttgacttct cctctgaagt tactgccgct   780
ttacgtgtca ctgacggtgc tttggttgtc gtcgacacca ttgaaggtgt ctgtgtccaa   840
accgaaactg ttttgagaca gctttgggt gagagaatca agcctgttgt tgttatcaac    900
aaggtcgaca gagctttgtt ggaattgcaa gtttctaagg aagatttata ccaaaccttt   960
```

-continued

```
gccagaactg ttgaatccgt taacgtcatc gtttccacct acgccgatga agttttgggt    1020
gatgtccaag tttacccagc cagaggtacc gttgccttcg gttccggttt gcacggttgg    1080
gctttcacta tccgtcaatt cgccaccaga tatgctaaga aattcggtgt cgacaaggcc    1140
aagatgatgg acagattatg gggtgactct ttcttcaacc caaagaccaa gaagtggacc    1200
aacaaggaca ctgatgctga aggtaagcca ttggaaagag ctttcaacat gttcatcttg    1260
gacccaatct tcagattatt cactgctatc atgaacttca agaaagatga aattccagtt    1320
ttgctagaaa agttggaaat tgtcttgaag ggtgacgaaa aggacttgga aggtaaggcc    1380
ttgttgaagg ttgttatgag aaagttcttg ccagctgccg atgccttatt ggaaatgatt    1440
gtcttgcact tgccatctcc agtcactgct caagcctaca gagctgaaca attatacgaa    1500
ggtccagctg acgatgccaa ctgtattgct atcaagaact gtgatccaaa ggctgatttg    1560
atgttgtacg tctccaagat ggtgccaacc tctgataagg gtagattcta cgccttcggt    1620 agagttttg ccggtactgt taagtccggt caaaaggtca gaatccaagg tccaaactac    1680
gttccaggta agaaggacga tttgttcatc aaggccattc aaagagttgt tttgatgatg    1740
ggtagatttg tcgaaccaat cgatgactgt ccagccggta acattatcgg tttagtcggt    1800
atcgatcaat tcttgttgaa gactggtact ttgaccacca gtgaaactgc tcacaacatg    1860
aaggtcatga aattctctgt ctctccagtt gtgcaagtcg ctgtcgaagt caagaacgct    1920
aacgacttac caaaattggt cgaaggtttg aagagattgt ccagtctga tccatgtgtc    1980 ttgacctata tgtctgaatc cggtgaacat atcgttgctg gtaccggtga attgcatttg    2040
gaaatttgtt tgcaagattt ggaacacgac cacgctggtg ttccattgaa gatctcccca    2100
ccagttgtcg cttacagaga aactgttgaa agtgaatctt ctcaaactgc tttgtccaag    2160
tctccaaaca agcataacag aatctacttg aaggctgaac caattgacga agaagtctct    2220
ttggctattg aaaacggtat catcaaccca agagatgatt caaggccag agctagaatc    2280 atggctgacg actacggttg ggatgtcacc gatgccagaa agatctggtg tttcggtcca    2340
gacggtaacg gtccaaactt ggttattgac caaactaagg ctgtccaata cttgcacgaa    2400
atcaaggatt ccgttgttgc tgcttttcaa tgggctacca aggaaggtcc aattttcggt    2460
gaagaaatga gatctgtcag agttaacatt ttggatgtta ctttacatgc cgatgctatc    2520
cacagaggtg gtgtcaaat catcccaacc atgagaagag ctacttacgc tggtttcttg    2580
ttggctgatc caaagatcca agaaccagtt ttcttggtcg aaattcaatg tccagaacaa    2640
gccgtcggtg gtatctactc cgtcttaaac aagaagagag gtcaagtcgt ttctgaagaa    2700
caaagaccag gtactccatt gtttaccgtc aaggcctact gccagttaa cgaatctttc    2760 ggtttcactg gtgaattgag acaagctact ggtggtcaag ctttcccaca aatggttttc    2820
gaccattggt ccactttagg ttctgaccca ttggacccaa cctctaaggc tggtgaaatt    2880
gttcttgctg ctcgtaagag acacggtatg aaggaagaag ttccaggctg caagaatat    2940 tacgacaaat tgtaagaatg gttaaacaat ttttaattat ttaactttt cagttttgt    3000 cgtaatgtat tgggcacctt ttatgtcctt ttgactttt tgtagtttat tctcacgtat    3060
acttaccatc tatagtgtta tttcatattt aatcatattt ccatattaga tatctgcctt    3120 ccctgtata atagttacta tgatttatct tgctttgcct attcgcgtca tcaacttctt    3180
ttcttaccga tcgcggtaat gccctttaag agtggcatca acattggcgt aaacaaagtt    3240
tcaaaggatt gatacgaaca cacattccta gcatgaaagc atggaactct catcaaactt    3300
```

```
aaaagaccta tatattgaat ggttacaaga attagttgac ggattaaccc ctaaacaaga    3360
acaactcaaa atagcctatg aaaaagcaaa aaggaattta caaatgctg aaggttcatt    3420 ttattatcct acagatctaa agaaagttaa gggaatt                            3457
```

<210> SEQ ID NO 4
<211> LENGTH: 842
<212> TYPE: PRT
<213> ORGANISM: Saccharomyces cerevisiae

<400> SEQUENCE: 4

```
Met Val Ala Phe Thr Val Asp Gln Met Arg Ser Leu Met Asp Lys Val
 1               5                  10                  15

Thr Asn Val Arg Asn Met Ser Val Ile Ala His Val Asp His Gly Lys
            20                  25                  30

Ser Thr Leu Thr Asp Ser Leu Val Gln Arg Ala Gly Ile Ile Ser Ala
        35                  40                  45

Ala Lys Ala Gly Glu Ala Arg Phe Thr Asp Thr Arg Lys Asp Glu Gln
 50                  55                  60

Glu Arg Gly Ile Thr Ile Lys Ser Thr Ala Ile Ser Leu Tyr Ser Glu
 65                  70                  75                  80

Met Ser Asp Glu Asp Val Lys Glu Ile Lys Gln Lys Thr Asp Gly Asn
            85                  90                  95

Ser Phe Leu Ile Asn Leu Ile Asp Ser Pro Gly His Val Asp Phe Ser
        100                 105                 110

Ser Glu Val Thr Ala Ala Leu Arg Val Thr Asp Gly Ala Leu Val Val
        115                 120                 125

Val Asp Thr Ile Glu Gly Val Cys Val Gln Thr Glu Thr Val Leu Arg
130                 135                 140

Gln Ala Leu Gly Glu Arg Ile Lys Pro Val Val Ile Asn Lys Val
145                 150                 155                 160

Asp Arg Ala Leu Leu Glu Leu Gln Val Ser Lys Glu Asp Leu Tyr Gln
                165                 170                 175

Thr Phe Ala Arg Thr Val Glu Ser Val Asn Val Ile Val Ser Thr Tyr
            180                 185                 190

Ala Asp Glu Val Leu Gly Asp Val Gln Val Tyr Pro Ala Arg Gly Thr
        195                 200                 205

Val Ala Phe Gly Ser Gly Leu His Gly Trp Ala Phe Thr Ile Arg Gln
210                 215                 220

Phe Ala Thr Arg Tyr Ala Lys Lys Phe Gly Val Asp Lys Ala Lys Met
225                 230                 235                 240

Met Asp Arg Leu Trp Gly Asp Ser Phe Asn Pro Lys Thr Lys Lys
                245                 250                 255

Trp Thr Asn Lys Asp Thr Asp Ala Glu Gly Lys Pro Leu Glu Arg Ala
            260                 265                 270

Phe Asn Met Phe Ile Leu Asp Pro Ile Phe Arg Leu Phe Thr Ala Ile
        275                 280                 285

Met Asn Phe Lys Lys Asp Glu Ile Pro Val Leu Leu Glu Lys Leu Glu
        290                 295                 300

Ile Val Leu Lys Gly Asp Glu Lys Asp Leu Glu Gly Lys Ala Leu Leu
305                 310                 315                 320

Lys Val Val Met Arg Lys Phe Leu Pro Ala Ala Asp Ala Leu Leu Glu
                325                 330                 335

Met Ile Val Leu His Leu Pro Ser Pro Val Thr Ala Gln Ala Tyr Arg
            340                 345                 350
```

-continued

```
Ala Glu Gln Leu Tyr Glu Gly Pro Ala Asp Asp Ala Asn Cys Ile Ala
    355                 360                 365
Ile Lys Asn Cys Asp Pro Lys Ala Asp Leu Met Leu Tyr Val Ser Lys
    370                 375                 380
Met Val Pro Thr Ser Asp Lys Gly Arg Phe Tyr Ala Phe Gly Arg Val
385                 390                 395                 400
Phe Ala Gly Thr Val Lys Ser Gly Gln Lys Val Arg Ile Gln Gly Pro
                405                 410                 415
Asn Tyr Val Pro Gly Lys Lys Asp Leu Phe Ile Lys Ala Ile Gln
            420                 425                 430
Arg Val Val Leu Met Met Gly Arg Phe Val Glu Pro Ile Asp Asp Cys
            435                 440                 445
Pro Ala Gly Asn Ile Ile Gly Leu Val Gly Ile Asp Gln Phe Leu Leu
    450                 455                 460
Lys Thr Gly Thr Leu Thr Thr Ser Glu Thr Ala His Asn Met Lys Val
465                 470                 475                 480
Met Lys Phe Ser Val Ser Pro Val Val Gln Val Ala Val Glu Val Lys
                485                 490                 495
Asn Ala Asn Asp Leu Pro Lys Leu Val Glu Gly Leu Lys Arg Leu Ser
            500                 505                 510
Lys Ser Asp Pro Cys Val Leu Thr Tyr Met Ser Glu Ser Gly Glu His
            515                 520                 525
Ile Val Ala Gly Thr Gly Glu Leu His Leu Glu Ile Cys Leu Gln Asp
    530                 535                 540
Leu Glu His Asp His Ala Gly Val Pro Leu Lys Ile Ser Pro Pro Val
545                 550                 555                 560
Val Ala Tyr Arg Glu Thr Val Glu Ser Glu Ser Ser Gln Thr Ala Leu
                565                 570                 575
Ser Lys Ser Pro Asn Lys His Asn Arg Ile Tyr Leu Lys Ala Glu Pro
            580                 585                 590
Ile Asp Glu Glu Val Ser Leu Ala Ile Glu Asn Gly Ile Ile Asn Pro
    595                 600                 605
Arg Asp Asp Phe Lys Ala Arg Ala Arg Ile Met Ala Asp Asp Tyr Gly
    610                 615                 620
Trp Asp Val Thr Asp Ala Arg Lys Ile Trp Cys Phe Gly Pro Asp Gly
625                 630                 635                 640
Asn Gly Pro Asn Leu Val Ile Asp Gln Thr Lys Ala Val Gln Tyr Leu
                645                 650                 655
His Glu Ile Lys Asp Ser Val Val Ala Ala Phe Gln Trp Ala Thr Lys
            660                 665                 670
Glu Gly Pro Ile Phe Gly Glu Glu Met Arg Ser Val Arg Val Asn Ile
            675                 680                 685
Leu Asp Val Thr Leu His Ala Asp Ala Ile His Arg Gly Gly Gly Gln
    690                 695                 700
Ile Ile Pro Thr Met Arg Arg Ala Thr Tyr Ala Gly Phe Leu Leu Ala
705                 710                 715                 720
Asp Pro Lys Ile Gln Glu Pro Val Phe Leu Val Glu Ile Gln Cys Pro
                725                 730                 735
Glu Gln Ala Val Gly Gly Ile Tyr Ser Val Leu Asn Lys Lys Arg Gly
            740                 745                 750
Gln Val Val Ser Glu Glu Gln Arg Pro Gly Thr Pro Leu Phe Thr Val
            755                 760                 765
```

```
Lys Ala Tyr Leu Pro Val Asn Glu Ser Phe Gly Phe Thr Gly Glu Leu
    770                 775                 780

Arg Gln Ala Thr Gly Gly Gln Ala Phe Pro Gln Met Val Phe Asp His
785                 790                 795                 800

Trp Ser Thr Leu Gly Ser Asp Pro Leu Asp Pro Thr Ser Lys Ala Gly
                805                 810                 815

Glu Ile Val Leu Ala Ala Arg Lys Arg His Gly Met Lys Glu Glu Val
                820                 825                 830

Pro Gly Trp Gln Glu Tyr Tyr Asp Lys Leu
            835                 840

<210> SEQ ID NO 5
<211> LENGTH: 3277
<212> TYPE: DNA
<213> ORGANISM: Saccharomyces cerevisiae

<400> SEQUENCE: 5
```

| | | | | | |
|---|---|---|---|---|---|
| cgatcgaagg | tgtaaacttc | agtagttctt | taatgccgtt | aatttccaag | tcttcctcgt | 60 |
| taccgtattt | atgtgtcata | tactcggaaa | catagtactc | aggatcaaac | ttcaaatttt | 120 |
| cttttcttaa | cctttcaata | actctatcgt | tcgcgtcagt | gtgttcagga | tcgtctaatt | 180 |
| cattgatatc | gttcccgttg | cttgtcgaca | ctgatataac | tgtatcatat | aagttatcaa | 240 |
| acccatatttt | tgtcttcaat | attccattat | tggtgctgga | atccatcttt | tgctctatct | 300 |
| cccaattaaa | cccctctccc | atttgaccaa | tagtcttcac | atcatcttta | atattattcg | 360 |
| acacgccatc | agtttcgacc | tcttgaataa | ggggcttttg | ggttttttc | gcatcagtat | 420 |
| tttctgttaa | tgcatcggca | cctgcaagat | cgccttgcct | agccaacaac | tttgtcggta | 480 |
| ggtccaaatc | ttcgaaatat | tcattttat | tcagtttggc | tacttttaca | ttgatgcatt | 540 |
| catctttgga | atcgtattga | gcggtagacc | tctcatcatc | gattaattcg | tgaggaaatc | 600 |
| ttaatcttaa | atagtaaggg | gataagtgaa | aaatgatcat | attttcttgg | atgattatct | 660 |
| ctaaacccac | tgcactgaac | ctaatattac | ttatgaatat | tttgagaaat | ataaattcct | 720 |
| catcctgtgt | tatagagaat | cttggtgtta | tcattatagt | tcagaagtga | tggtagatta | 780 |
| tagcaagtat | tcttcttttg | tgaatcttaa | tattactctg | agcacttgac | actgaatatt | 840 |
| tagtattcaa | aattttcag | ctgattttg | cgatgcgatg | gtgatgaaaa | aaaaaacatg | 900 |
| tagtagtaat | aacaatcaaa | taaaataagt | gaaatctcat | gaactatctg | ctgcgaattt | 960 |
| taaggataat | cggatagctt | gaagcatttc | tttttcgtaa | tgagtggctc | tacagaatct | 1020 |
| aaaaaacaac | caagaagaag | atttattggg | agaaaatctg | gcaacagtaa | taatgacaaa | 1080 |
| ttaactacag | tggctgaaaa | tggcaacgaa | ataatccaca | agcaaaagag | tagaatcgcc | 1140 |
| ctaggtagga | gtgttaatca | tgtgccagaa | gatatattga | atgacaaaga | gttgaatgaa | 1200 |
| gccatcaaat | tattgccctc | taactacaac | tttgaaatcc | acaaaactgt | gtggaatatc | 1260 |
| aggaaatata | atgctaaaag | aatagcccta | cagatgcctg | aaggtttgct | gatttactca | 1320 |
| ttgattataa | gtgacatttt | ggaacagttc | tgtggtgttg | aaactctagt | aatgggggat | 1380 |
| gtgtcttatg | gtgcatgctg | tattgatgat | tttactgcta | gggcattgga | ttgcgatttt | 1440 |
| attgtgcatt | acgctcattc | gtgtttagtt | cctattgacg | ttacaaagat | taaagtacta | 1500 |
| tatgtctttg | ttactataaa | tattcaagaa | gatcatatta | tcaaaacgct | gcagaagaat | 1560 |
| tttcctaagg | gatctagaat | cgctacattt | ggtaccattc | agtttaatcc | tgcggtacac | 1620 |
| agcgtcagag | ataaactgct | taacgatgaa | gaacacatgc | tgtatattat | tccaccacaa | 1680 |

-continued

```
atcaagcctc tatcgagggg tgaagtattg gggtgtactt ctgaaagatt agataaagaa     1740
caatacgatg ccatggtatt catcggtgat ggtagatttc atttggagtc tgcaatgata     1800
cataatccgg aaattcctgc attcaagtat gacccataca acagaaagtt cactagagaa     1860
ggatacgatc aaaagcaact cgtggaagtt agagcagagg ccattgaagt cgctcggaag     1920
ggtaaagttt ttggtctgat cttaggtgca ttaggtagac aagtaatttt aaacactgta     1980
aaaaacttgg aaaaaaacct gatcgcagca ggtaaaaccg tggtgaaaat tattctaagt     2040 gaagttttc cccaaaagct cgcaatgttc gatcaaattg atgttttgt tcaggtcgca       2100 tgtcctagac tgtccatcga ttggggttat gccttcaata accactatt aacaccatat      2160 gaggctagtg tcttactaaa gaaagatgtc atgttcagcg aaaaatatta tccaatggat     2220
tattacgaag ctaaaggata cgggcgtggg gaaactccga acatgcgat tgaatagttt       2280 aaatagtttt tgttgtcact tgtcttcctg ttacatatgt ataaatagtt agtatcatat     2340
tcttcggagc atcttttcta ttgtttaaac gttttttgacg gcttgcaggc gaaactaaat    2400
tgtctaaaat tcaaacaat gccttctaac ttgatatcac tgctggtcaa gcctatttt       2460 attctggttt ctcaggcaaa cccaaatgat attgtcaaat ttttcactga gtttgccaag    2520
catatttcca tggactttg tatggaaacc gtgatgagaa atccgggatt tctcatcgag      2580
gaaagaagtg actcgagcct cttaaggctt agattaaact ttttctttt tatcgctgcg     2640 tataagcaat acacctaaaa cagaaccagt taaagtaaac ccgatcaaca gtaagaagat     2700
gggcaggaaa attgcaacat tgctagaaat ggggaagagt aaactcacaa ctggattgga    2760
gttctcgatc tcgaagatag gcaggagcga ccatatgaca taataagtaa aagaaggca     2820 aataattaca aaacggttca tgaaactaaa cagacgttta ctatgcccaa ccggtgacta    2880
ttcacatttt tgagctagta ttgcatttag agtacacgca gtcatcaaca gtttctttgt     2940
atctctttca aatatattcc tttacacggg aatgctagcg gaaatgaatg taaggcggaa    3000
aagctctccg tgcgaaacta ttctttagaa cactgaataa agttgtagcc tcattccata    3060
atctgggtca gattttatga aaatgtagtt atttctgtta gttgctgggt tctacgatat     3120
tctgctgcgt ggtttagctt tcatacttga ttttactcc ttcatcactc catataggtt      3180
ggatatggct gaatctgttt ttatcgaggc acccttatga acataaacaa cagtatcccg     3240
tctaagaaat actttcgcta caatgacttc gaaaatt                              3277
```

<210> SEQ ID NO 6
<211> LENGTH: 425
<212> TYPE: PRT
<213> ORGANISM: Saccharomyces cerevisiae

<400> SEQUENCE: 6

```
Met Ser Gly Ser Thr Glu Ser Lys Lys Gln Pro Arg Arg Phe Ile
 1               5                  10                  15

Gly Arg Lys Ser Gly Asn Ser Asn Asn Asp Lys Leu Thr Thr Val Ala
                20                  25                  30

Glu Asn Gly Asn Glu Ile Ile His Lys Gln Lys Ser Arg Ile Ala Leu
            35                  40                  45

Gly Arg Ser Val Asn His Val Pro Glu Asp Ile Leu Asn Asp Lys Glu
        50                  55                  60

Leu Asn Glu Ala Ile Lys Leu Leu Pro Ser Asn Tyr Asn Phe Glu Ile
    65                  70                  75                  80

His Lys Thr Val Trp Asn Ile Arg Lys Tyr Asn Ala Lys Arg Ile Ala
                85                  90                  95
```

-continued

```
Leu Gln Met Pro Glu Gly Leu Leu Ile Tyr Ser Leu Ile Ile Ser Asp
             100                 105                 110
Ile Leu Glu Gln Phe Cys Gly Val Glu Thr Leu Val Met Gly Asp Val
         115                 120                 125
Ser Tyr Gly Ala Cys Cys Ile Asp Asp Phe Thr Ala Arg Ala Leu Asp
     130                 135                 140
Cys Asp Phe Ile Val His Tyr Ala His Ser Cys Leu Val Pro Ile Asp
145                 150                 155                 160
Val Thr Lys Ile Lys Val Leu Tyr Val Phe Val Thr Ile Asn Ile Gln
                 165                 170                 175
Glu Asp His Ile Ile Lys Thr Leu Gln Lys Asn Phe Pro Lys Gly Ser
             180                 185                 190
Arg Ile Ala Thr Phe Gly Thr Ile Gln Phe Asn Pro Ala Val His Ser
         195                 200                 205
Val Arg Asp Lys Leu Leu Asn Asp Glu His Met Leu Tyr Ile Ile
     210                 215                 220
Pro Pro Gln Ile Lys Pro Leu Ser Arg Gly Glu Val Leu Gly Cys Thr
225                 230                 235                 240
Ser Glu Arg Leu Asp Lys Glu Gln Tyr Asp Ala Met Val Phe Ile Gly
                 245                 250                 255
Asp Gly Arg Phe His Leu Glu Ser Ala Met Ile His Asn Pro Glu Ile
             260                 265                 270
Pro Ala Phe Lys Tyr Asp Pro Tyr Asn Arg Lys Phe Thr Arg Glu Gly
         275                 280                 285
Tyr Asp Gln Lys Gln Leu Val Glu Val Arg Ala Glu Ala Ile Glu Val
     290                 295                 300
Ala Arg Lys Gly Lys Val Phe Gly Leu Ile Leu Gly Ala Leu Gly Arg
305                 310                 315                 320
Gln Gly Asn Leu Asn Thr Val Lys Asn Leu Glu Lys Asn Leu Ile Ala
                 325                 330                 335
Ala Gly Lys Thr Val Val Lys Ile Ile Leu Ser Glu Val Phe Pro Gln
             340                 345                 350
Lys Leu Ala Met Phe Asp Gln Ile Asp Val Phe Val Gln Val Ala Cys
         355                 360                 365
Pro Arg Leu Ser Ile Asp Trp Gly Tyr Ala Phe Asn Lys Pro Leu Leu
     370                 375                 380
Thr Pro Tyr Glu Ala Ser Val Leu Leu Lys Asp Val Met Phe Ser
385                 390                 395                 400
Glu Lys Tyr Tyr Pro Met Asp Tyr Tyr Glu Ala Lys Gly Tyr Gly Arg
                 405                 410                 415
Gly Glu Thr Pro Lys His Ala Ile Glu
             420                 425
```

<210> SEQ ID NO 7
<211> LENGTH: 3095
<212> TYPE: DNA
<213> ORGANISM: Saccharomyces cerevisiae

<400> SEQUENCE: 7

```
atccataatg atggctatgt ggtgctagat ttcttccgac ttcttgctat tttcattcaa    60
aaggttatac atgtttatt tttcaacagt accttaatat ataataattc ggggccaaaa   120
taacaaacaa cgagaaaaag ggaggagaga gtaaagtata gtattaacag ggctggttat   180
atagatatat atatatacgg gtcaatcgat ctatttatat acatacgaat ataatatgac   240
```

-continued

```
atggggtga cacgatacaa tataatagag cggggacgga cacttagttt gcgtcgggat      300
tggaagcgat ataatcgacc gtttcaccaa cacttctcaa ctcatcagcc actttgtcag      360
ggatttcaat atcaaattct tcttcaatag ctacgagcag ctcgacagtg tccaaggagt      420
ccaaccccaa atccttgtga aattgggtat cgctggagat ttgcttgttg caatgttgg       480 gagagttctt atcaaacgcc ttgataacat caatgaccct tgagaaacc tgatctttgc       540 tcaagtttgc agaataaaat ctttgtgcga gtatggtgtt ggacataacg aacggccca       600 ttatagtgcg gtacgcagaa ggtgccacgc gggaagaaat gcggcaaacg gatctaaaca      660
tggcaaggaa ggtgctgtat tgagttagtt gtgttgtttg tactaattac actgcaagtg      720
tgactattct tccttttgct tcgtcatcac cacctttctc ttttactcag aacccgttcg      780
aaggggcgaa gaaagaagca attgacaaat aatctgtatt ccgtcaacag tgatatatgt      840
cacgtgactc tgataaaaact ccatggagtc tcttcggagt gtatgtgtga aaagaataat     900
acatataaga catctacagg atcagtctga tagttttaat gctatggtag acttcagaat      960
gtctttttaa gtatgccatt tggttaaatc tgtccttta tatgtacttg gtgcttcttt       1020
tttctttact tttttttttt tcagtgagaa gctcatcgca acaagaagaa aaaagactag      1080
ttcaaaggta aaagagttaa gatgattagt gatggatttc taagtggcag cgttgaaaga     1140
tcgtgcaaag gttgaaaaat ggaagttgca ccggccttat cgactactca gtcggacgtg      1200
gcgtttcaga aggtggagac acatgaaatt gacaggtctt catacttggg gccatgttat      1260
aatagcgatg agcttatgca acttatctcg gcttattaca atgtcgagcc tctcgtgggt      1320
tatctggaac agcacccgga gtaccaaaac gtgaccttgc agtttcctga cgatttaatc      1380
aaggactcct cgttgatagt aaggctgctg caatcgaaat ttccccatgg aagataaag       1440 ttttgggttt tagctgacac agcgtacagt gcatgctgtg tagacgaggt cgctgctgaa      1500
cacgtacatg cagaagtcgt ggtacatttt ggtgacgcat gtttgaacgc atccaaaac      1560 ttgcccgtgg tttactcatt cggaactcca tttttggatt tggcactggt ggtggagaac      1620
tttcagaggg cattcccaga cttatcctcc aaaatttgtt tgatggcaaa cgcacccttc      1680
tctaagcatt tgtcacagct gtacaatatt ttgaagggcg acctgcacta cacaaatatc      1740
atatattccc aagtgaacac ctctgcggta gaagaaaaaat tcgtaaccat acttgacacc      1800
tttcacgttc ccgaagacgt agaccaggtg ggtgtgttcg aaaaaaatag cgtgctgttt      1860
ggtcagcacg acaaagcaga caacatctcg cccgaggact atcatctttt ccatttgacc      1920
accccacagg atccgagatt actgtatttg tctactgtgt ttcaatctgt tcatattttc      1980
gatccggctt tacctggcat ggtaacgggg ccatttccct ctctaatgag gcgttacaag      2040
tacatgcatg tggcaagaac agcgggatgt ataggtattc tggtcaacac gctgtcgcta      2100
cgtaatacaa gagaaactat caacgagctg gtcaagctta tcaaaactcg tgagaaaaaa      2160
cactatttat tgttgtcgg aaagccaaat gtggccaagc tagcaaactt tgaagatatt      2220
gatatttggt gcattctcgg ttgtagccaa agcggtatca tcgttgatca attcaacgag      2280
ttttacaagc ccattattac accttatgaa ttaaacttgg ccttgagcga agaggtcaca      2340
tggaccggga aatggggttgt ggacttcaga gacgccattg atgaaatcga gcagaatttg      2400
ggcggacaag ataccatctc tgccagcaca acttccgatg aaccggagtt tgatgtagtt      2460 agggaagat atactagcac atcaagacca ctgcgagcgc taacgcacct ggagttagag      2520
gcggccgacg acgacgattc caaacaactg actacaagac ataccgcctc aggtgccgtc      2580
```

-continued

```
attaaaggta ctgtatccac ttcagcatca gcactgcaga atcgttcgtg aaaggtcta      2640 ggaagcgatt tcgactctac tgaggttgat aatactggag cggatatcga agaaggtatt    2700
tccggtgtcg cacgtggtta tggatttgat cgcgaagacg ctatgaaaaa ggaaaacaaa    2760
tgactcttat aatttgtttc cctcgacttc tctatttaaa tccaagattt taactaataa    2820
actatttaat aataaaacaa ttaactcttt atatggaagc cttggaaatt agccgccaaa    2880
atgggatata cattccgtgc gaagtgaccg cgtggaaggc cgggtatcat cttaaaaatc    2940
actagtttct tttttagcgg aatgcaataa aggtgctttg tgctggtgtg gtttacacgg    3000
aacatctagt agctaaaact tggtaactca atggtgatca gaatccatag aagcattttt    3060
atttcttaaa atgggtgctg ctccttccaa aattg                               3095
```

<210> SEQ ID NO 8
<211> LENGTH: 534
<212> TYPE: PRT
<213> ORGANISM: Saccharomyces cerevisiae

<400> SEQUENCE: 8

```
Met Glu Val Ala Pro Ala Leu Ser Thr Thr Gln Ser Asp Val Ala Phe
 1               5                  10                  15

Gln Lys Val Glu Thr His Glu Ile Asp Arg Ser Ser Tyr Leu Gly Pro
            20                  25                  30

Cys Tyr Asn Ser Asp Glu Leu Met Gln Leu Ile Ser Ala Tyr Tyr Asn
        35                  40                  45

Val Glu Pro Leu Val Gly Tyr Leu Glu Gln His Pro Glu Tyr Gln Asn
    50                  55                  60

Val Thr Leu Gln Phe Pro Asp Asp Leu Ile Lys Asp Ser Ser Leu Ile
65                  70                  75                  80

Val Arg Leu Leu Gln Ser Lys Phe Pro His Gly Lys Ile Lys Phe Trp
                85                  90                  95

Val Leu Ala Asp Thr Ala Tyr Ser Ala Cys Cys Val Asp Glu Val Ala
            100                 105                 110

Ala Glu His Val His Ala Glu Val Val His Phe Gly Asp Ala Cys
        115                 120                 125

Leu Asn Ala Ile Gln Asn Leu Pro Val Val Tyr Ser Phe Gly Thr Pro
    130                 135                 140

Phe Leu Asp Leu Ala Leu Val Val Glu Asn Phe Gln Arg Ala Phe Pro
145                 150                 155                 160

Asp Leu Ser Ser Lys Ile Cys Leu Met Ala Asn Ala Pro Phe Ser Lys
                165                 170                 175

His Leu Ser Gln Leu Tyr Asn Ile Leu Lys Gly Asp Leu His Tyr Thr
            180                 185                 190

Asn Ile Ile Tyr Ser Gln Val Asn Thr Ser Ala Val Glu Glu Lys Phe
        195                 200                 205

Val Thr Ile Leu Asp Thr Phe His Val Pro Glu Asp Val Asp Gln Val
    210                 215                 220

Gly Val Phe Glu Lys Asn Ser Val Leu Phe Gln His Asp Lys Ala
225                 230                 235                 240

Asp Asn Ile Ser Pro Glu Asp Tyr His Leu Phe His Leu Thr Thr Pro
                245                 250                 255

Gln Asp Pro Arg Leu Leu Tyr Leu Ser Thr Val Phe Gln Ser Val His
            260                 265                 270

Ile Phe Asp Pro Ala Leu Pro Gly Met Val Thr Gly Pro Phe Pro Ser
        275                 280                 285
```

```
Leu Met Arg Arg Tyr Lys Tyr Met His Val Ala Arg Thr Ala Gly Cys
    290                 295                 300
Ile Gly Ile Leu Val Asn Thr Leu Ser Leu Arg Asn Thr Arg Glu Thr
305                 310                 315                 320
Ile Asn Glu Leu Val Lys Leu Ile Lys Thr Arg Glu Lys Lys His Tyr
                325                 330                 335
Leu Phe Val Val Gly Lys Pro Asn Val Ala Lys Leu Ala Asn Phe Glu
            340                 345                 350
Asp Ile Asp Ile Trp Cys Ile Leu Gly Cys Ser Gln Ser Gly Ile Ile
        355                 360                 365
Val Asp Gln Phe Asn Glu Phe Tyr Lys Pro Ile Ile Thr Pro Tyr Glu
    370                 375                 380
Leu Asn Leu Ala Leu Ser Glu Glu Val Thr Trp Thr Gly Lys Trp Val
385                 390                 395                 400
Val Asp Phe Arg Asp Ala Ile Asp Glu Ile Glu Gln Asn Leu Gly Gly
                405                 410                 415
Gln Asp Thr Ile Ser Ala Ser Thr Thr Ser Asp Glu Pro Glu Phe Asp
            420                 425                 430
Val Val Arg Gly Arg Tyr Thr Ser Thr Ser Arg Pro Leu Arg Ala Leu
        435                 440                 445
Thr His Leu Glu Leu Glu Ala Ala Asp Asp Asp Ser Lys Gln Leu
    450                 455                 460
Thr Thr Arg His Thr Ala Ser Gly Ala Val Ile Lys Gly Thr Val Ser
465                 470                 475                 480
Thr Ser Ala Ser Ala Leu Gln Asn Arg Ser Trp Lys Gly Leu Gly Ser
                485                 490                 495
Asp Phe Asp Ser Thr Glu Val Asp Asn Thr Gly Ala Asp Ile Glu Glu
            500                 505                 510
Gly Ile Ser Gly Val Ala Arg Gly Tyr Gly Phe Asp Arg Glu Asp Ala
        515                 520                 525
Met Lys Lys Glu Asn Lys
    530

<210> SEQ ID NO 9
<211> LENGTH: 1170
<212> TYPE: DNA
<213> ORGANISM: Saccharomyces cerevisiae

<400> SEQUENCE: 9
tcatatgacc atagcacata cttttttgtcc tggtgtgttt ataacgtctt cttgtgagta      60
ccaaaaagca aatggcaagt gtaatttcct ataactttaa gataggcctg taaataacgt     120
atatgaaaca gttccatccc gtaacaccat gaacactgcg taagagaaag ccctcaagct     180
ttcccagcga tgctcgtgtg taggaccgaa catggagggg ggaactaggc ccagcacggg     240
tttggcgagg ccgctctgct cgcagctcag gattctaaaa ggttattccg ctgagaaaat     300
cagaaaatag gaacttctca cgcaataatt ttaaagttga tgaaaagga aaatttgtaa     360 aagtgtaagg gtgttaaaga gggtgtatgg atgtaaagtc acaaaagtta gagcagatga     420 aaagaaatg ggtggagaca aatccgaaaa aggacctata ttatcgctat aaagagcttc     480
tcatcgcttt tttttttcaa agacacatac ataccacgac tgtaagcaca tcatttgtac     540
aatacattac cagctgaaat gtcaacatat gacgaaatcg aaatcgaaga tatgacgttt     600
gagcctgaaa atcaaatgtt cacctatcct tgtccctgtg gagataggtt tcaaatatat     660
```

```
ctggatgaca tgtttgaggg cgaaaaagtt gctgtttgtc ccagctgctc actgatgatc    720
gatgtagttt tcgataaaga agacttggct gagtactacg aagaggcagg catccacccc    780
cctgagccta ttgccgctgc tgcctaaaga tgagaggcta atcgagaat acaaatagaa     840 ataaagaaag agctatatga cttagcaacg caagcagaaa agaaggtttg cttcttcgct    900
ggactccggt tggaattact attcaaaatt ccaagtgcac tgatgaaaa cgttttgctc     960 aggttgagct cttttactgc atataaggat actgggtagg tgtatatgat tattttatac   1020
atgatacgta ggctaaaatg atttggaccc attaaatcat cttgtcgcat ctctttttctt  1080 tttcctccat gctcagattt caataatatc atctcaaatg gctgtgacaa atttcaccgg   1140
aaaggcgagg gattttttctg ttgacattat                                    1170
```

<210> SEQ ID NO 10
<211> LENGTH: 82
<212> TYPE: PRT
<213> ORGANISM: Saccharomyces cerevisiae

<400> SEQUENCE: 10

```
Met Ser Thr Tyr Asp Glu Ile Glu Ile Glu Asp Met Thr Phe Glu Pro
 1               5                  10                  15

Glu Asn Gln Met Phe Thr Tyr Pro Cys Pro Cys Gly Asp Arg Phe Gln
            20                  25                  30

Ile Tyr Leu Asp Asp Met Phe Glu Gly Glu Lys Val Ala Val Cys Pro
        35                  40                  45

Ser Cys Ser Leu Met Ile Asp Val Val Phe Asp Lys Glu Asp Leu Ala
    50                  55                  60

Glu Tyr Tyr Glu Glu Ala Gly Ile His Pro Pro Glu Pro Ile Ala Ala
65                  70                  75                  80

Ala Ala
```

<210> SEQ ID NO 11
<211> LENGTH: 1619
<212> TYPE: DNA
<213> ORGANISM: Saccharomyces cerevisiae

<400> SEQUENCE: 11

```
aatccagatt tattaaaagt ttgcaaagag gtggaccgta atccaggtca agttttgatt     60
cgttggtctt tacaacacgg ttatttacca ctaccgaaga ctaaaactgt gaagaggtta    120
gaaggtaacc ttgcagccta caactttgaa ctgtcagacg aacagatgaa atttcttgat    180
catcctgatg cttatgagcc taccgattgg gaatgcacag acgcgccata aaagaaaat    240 gcgaaccgta gaataacgta tagaacat ataattagtt tacgtttcac aaagtattaa    300
tattacatgt agctttttca ggactttcga tctaaatcaa agattaaagg agctgctaga   360
ggtagaaaag gaaatcattg acttttcttg aagatttatg agcgggtaac tggagatgga   420
aattttcaga aaaattgtaa atggatgcga tgacttcgat gtgacgttac tagtcttacc   480
attgtaaaaa ccactatcgg tgccaaaaga taagcgcaat caactaagaa atttaccacg   540
ctctttgtat tgtatttatc tccaatttaa tcttctttt ggtgtgaaaa tttagcgaaa   600
atgtcattgg tgaattcgtt aacacactac gaaattttaa gaattccatc ggatgcaaca   660
caagatgaaa tcaaaaaggc atataggaat cggttactaa atacgcaccc cgataaactt    720
tctaaaagca tacatgatac ggttagcaac gtcacaatca ataagattca agatgcttat    780
aaaatactat cgaatataaa aactcgtcgc gaatatgata ggttgatcct tgaaaactat    840
```

-continued

```
aaacgccaag gatttcataa ttgtggtgat gggctggatg aatttccctt agacgatttc     900
tcatttgatg aagataagct ggagtttatg atgaattgtc ctcgctgtca atttgttggt     960
ggttttcatt ttagtgagag tttgttagat gaatgcattg ataatgtaga cgctatggaa    1020
cggagtcatt ctggttatca attattaacc caatgtagcg catgcagctt atggctgaag    1080
gttaattttg acatcgagga agagcaagaa ggacaataat gaaatgggaa ggggaaattg    1140
agcatatcag ataaatctgt ttatagaatt attattttac ttcgtgggaa atcgaatggt    1200
gtatataaaa gaggttgtaa aattgacgaa ataaatagta tttaggcaac taagataaaa    1260
aaaatattat ttatttttat tcgcggtgcg ttgccagatt ttttttgaca tgcggaattt    1320
tggtaaaaag aaaaatgcag atatgaatag taaacaaagg aataaaaagc ctttcatgaa    1380
gaagttcgtg ttcgagatct tcttccttct ttttcgctgt cgacgataga tatgaatgct    1440
tttgccattg atttcaaatc cgtcattaag ctaacatgac ctgaagaact ggcgatttta    1500
caaacaactg gaaagcctct ctgttcaggc aataaccatt tatggtgaac aacaccgtcg    1560
cccggaccat agtaaaaatc ttcataattc ccatcttta tatcttgtat accgttcac     1619
```

<210> SEQ ID NO 12
<211> LENGTH: 172
<212> TYPE: PRT
<213> ORGANISM: Saccharomyces cerevisiae

<400> SEQUENCE: 12

```
Met Ser Leu Val Asn Ser Leu Thr His Tyr Glu Ile Leu Arg Ile Pro
 1               5                  10                  15

Ser Asp Ala Thr Gln Asp Glu Ile Lys Lys Ala Tyr Arg Asn Arg Leu
            20                  25                  30

Leu Asn Thr His Pro Asp Lys Leu Ser Lys Ser Ile His Asp Thr Val
        35                  40                  45

Ser Asn Val Thr Ile Asn Lys Ile Gln Asp Ala Tyr Lys Ile Leu Ser
    50                  55                  60

Asn Ile Lys Thr Arg Arg Glu Tyr Asp Arg Leu Ile Leu Glu Asn Tyr
65                  70                  75                  80

Lys Arg Gln Gly Phe His Asn Cys Gly Asp Gly Leu Asp Glu Phe Ser
                85                  90                  95

Leu Asp Asp Phe Ser Phe Asp Glu Asp Lys Leu Glu Phe Met Met Asn
            100                 105                 110

Cys Pro Arg Cys Gln Phe Val Gly Gly Phe His Phe Ser Glu Ser Leu
        115                 120                 125

Leu Asp Glu Cys Ile Asp Asn Val Asp Ala Met Glu Arg Ser His Ser
    130                 135                 140

Gly Tyr Gln Leu Leu Thr Gln Cys Ser Ala Cys Ser Leu Trp Leu Lys
145                 150                 155                 160

Val Asn Phe Asp Ile Glu Glu Glu Gln Glu Gly Gln
                165                 170
```

<210> SEQ ID NO 13
<211> LENGTH: 2299
<212> TYPE: DNA
<213> ORGANISM: Saccharomyces cerevisiae

<400> SEQUENCE: 13

```
gcttctggcg tccgagtcat tttccgttcc tggccatttg tcataatcga accaaatttg      60
agagtgtata gacacctgca aatacttacc tgtatcattg ttcaggtcag agcccatatt     120
```

-continued

```
atctttccaa ccatcaagct gaaactccac cagtttgaaa tttgttactt gaactagatt    180
cttttctatc acatctgtgg gcggcacatg tcccctaata tactgcacta tgctgacgcc    240
aaagaaactt aataaaacaa tacctagcag atatataatt aagcacttta tactccgcca    300
acgagattta taagggtct catttgcaac gttgattctc acttcatcat tgaggagttg     360
gctttcttca gtgtttggtc tcaacagtgg ttgagtttct agatcttggt tatccgctcg    420
taagggtgag ttagtgtgca tcttaaaagg ttcaaggagt aatgcactac actaagcaat    480
aaaaaatccc aaaaacagga ggatcttgtg tcttcttccc ctagacagtt catcttttg     540
attctgggct tcgcatttac ctttagagaa aattaaataa ccccatgcat gcgattctaa    600
aaaaaagtta actaagcgat gggatgaaat ttttttctgg tggttgttag caaagtaaaa    660
acgaacagga tatagagtga ataaaggaca gtgagaaaaa tgctttattt gatcggactt    720
ggtctctcgt acaaatcaga cattaccgtt cgtggtttgg aagctattaa gaaatgttct    780
agagtttatc tagaacacta taccagtatc ctaatggctg caagccaaga gagttagaa    840
tcttactatg gtaaagagat catcttggct gataggggaat tagttgagac tggttctaag   900
cagatcctaa ataacgccga taaggaagac gttgctttct tggtcgtggg cgatccattt    960
ggtgccacca cacacacaga tttagttctc agagctaaac gtgaggcaat tcccgtcgaa    1020
attattcata atgcgtccgt tatgaatgca gttggggcat gtggcctaca actatacaat   1080
ttcggtcaaa ccgtttccat ggttttcttt accgataatt ggagaccaga ctcatggtac   1140
gacaagatct gggaaaatag aaaaattggc cttcatactt tagtgttatt ggacatcaaa   1200
gttaaggaac aaagcattga aaatatggcc cgtggcagac taatctacga accaccaaga   1260
tacatgtcta tcgctcaatg ttgtgaacaa ttattgaaaa ttgaagagaa aagaggtaca   1320
aaggcataca ctcctgatac tccagcagtc gcaattagta gattaggctc gagctcccaa   1380
agctttaagt ctggtaccat aagtgagtta gccaattacg attcaggaga gccacttcat   1440
tcgcttgtca tcctcggcag acaatgtcat gaattggagc tggaatacct gctagagttt   1500
gccgacgaca agaaaaagtt tgggaaagat gtggcaaatg accaagagta cttcaaacct   1560
gcggcatggg tcccacccac agaagacgac agcgacgagt aaaggtaatg cacacgctca   1620
tgtgtagttt cttttttata atgtatattg aatagatcct ttcagtcggg taacaattcg   1680
atcccaaacg aatcgggccc taacgatatg tgtaaaaatg gcaatgaatg aacaagaagt   1740
tataacaaca atttcagcca agaacaagag cgatcctgga ggagattata tacggataca   1800
caggtacaca agatgacgca attaaaatat ttgttgctgg tttctaggca aggaaaaatc   1860
agattaaaga aatggtacac ggcaatgtcc gctggtgaaa aggcaaaaat tgtgaaagac   1920
ttgacaccta cgatattagc aagaaaaccc aaaatgtgta acatcatcga gtataatgac   1980
cacaaagtag tatacaagcg atatgctagt ctatatttta ttgttgggat gacgcccgat   2040
gttgacaatg aactgctgac cttggaaatt atccatcggt ttgtcgaaac aatggacaca   2100
tatttcggca atgtttgtga gctagacatt atatttaact tcagtaaggt ctacgatatc   2160
ttgaatgaga tgattatgtg cgatggctcc atcgcagaga gcagtaggaa ggaagtactg   2220
caccatgtga ccgtgatgga caccatggag agcaacgata tcttgaaaag ggtattgagt   2280
taggaccact aaaaaacaa                                                 2299
```

<210> SEQ ID NO 14
<211> LENGTH: 300
<212> TYPE: PRT
<213> ORGANISM: Saccharomyces cerevisiae

```
<400> SEQUENCE: 14

Met Leu Tyr Leu Ile Gly Leu Gly Leu Ser Tyr Lys Ser Asp Ile Thr
1               5                   10                  15

Val Arg Gly Leu Glu Ala Ile Lys Lys Cys Ser Arg Val Tyr Leu Glu
            20                  25                  30

His Tyr Thr Ser Ile Leu Met Ala Ala Ser Gln Glu Glu Leu Glu Ser
        35                  40                  45

Tyr Tyr Gly Lys Glu Ile Ile Leu Ala Asp Arg Glu Leu Val Glu Thr
    50                  55                  60

Gly Ser Lys Gln Ile Leu Asn Asn Ala Asp Lys Glu Asp Val Ala Phe
65                  70                  75                  80

Leu Val Val Gly Asp Pro Phe Gly Ala Thr Thr His Thr Asp Leu Val
            85                  90                  95

Leu Arg Ala Lys Arg Glu Ala Ile Pro Val Glu Ile Ile His Asn Ala
            100                 105                 110

Ser Val Met Asn Ala Val Gly Ala Cys Gly Leu Gln Leu Tyr Asn Phe
            115                 120                 125

Gly Gln Thr Val Ser Met Val Phe Phe Thr Asp Asn Trp Arg Pro Asp
130                 135                 140

Ser Trp Tyr Asp Lys Ile Trp Glu Asn Arg Lys Ile Gly Leu His Thr
145                 150                 155                 160

Leu Val Leu Leu Asp Ile Lys Val Lys Glu Gln Ser Ile Glu Asn Met
                165                 170                 175

Ala Arg Gly Arg Leu Ile Tyr Glu Pro Pro Arg Tyr Met Ser Ile Ala
            180                 185                 190

Gln Cys Cys Glu Gln Leu Leu Glu Ile Glu Glu Lys Arg Gly Thr Lys
        195                 200                 205

Ala Tyr Thr Pro Asp Thr Pro Ala Val Ala Ile Ser Arg Leu Gly Ser
        210                 215                 220

Ser Ser Gln Ser Phe Lys Ser Gly Thr Ile Ser Glu Leu Ala Asn Tyr
225                 230                 235                 240

Asp Ser Gly Glu Pro Leu His Ser Leu Val Ile Leu Gly Arg Gln Cys
            245                 250                 255

His Glu Leu Glu Leu Glu Tyr Leu Leu Glu Phe Ala Asp Asp Lys Glu
            260                 265                 270

Lys Phe Gly Lys Asp Val Ala Asn Asp Gln Glu Tyr Phe Lys Pro Ala
            275                 280                 285

Ala Trp Val Pro Pro Thr Glu Asp Asp Ser Asp Glu
            290                 295                 300
```

What is claimed is:

1. A method of selectively killing a first microorganism, said method comprising:
   a) contacting said first microorganism with a second microorganism that recombinantly expresses a microcidal compound; and
   b) allowing said first microorganism and said second microorganism to undergo fusion, whereby said microcidal compound is delivered into and kills the microorganism that forms following said fusion.

2. The method of claim 1, wherein said first microorganism is a fungus.

3. The method of claim 2, wherein said fungus is *Saccharomyces cerevisiae*.

4. The method of claim 1, wherein said second microorganism is resistant to said microcidal compound.

5. The method of claim 1, wherein said second microorganism is a nonpathogenic fungus.

6. The method of claim 1, wherein said second microorganism is *Saccharomyces cerevisiae*.

7. The method of claim 1, wherein said fusion results from the mating of said first microorganism and said second microorganism.

8. The method of claim 1, wherein said fusion results from the anastomosis of said first organism and said second microorganism.

9. The method of claim 2, wherein said fungus is a pathogenic fungus.

10. The method of claim 9, wherein said pathogenic fungus is selected from the group consisting of: Absidia spp., *Actinomadura madurae*, Actinomyces spp., Allescheria boydii, Alternaria spp., *Anthopsis deltoidea*, Aphanomyces spp., *Apophysomyces eleqans*, Armillaria spp., *Arnium leoporinum*, Aspergillus spp., Aureobasidium pullulans, *Basidiobolus ranarum*, Bipolaris spp., *Blastomyces dermatitidis*, Botrytis spp., Candida spp., Centrospora spp., Cephalosporium spp., Ceratocystis spp., Chaetoconidium spp., Chaetomium spp., Cladosporium spp., Coccidioides immitis, Colletotrichum spp, Conidiobolus spp., Cryptoporiopsis spp., Cylindrocladium spp., Cryptococcus spp., *Cunninghamella bertholletiae*, Curvularia spp., Dactylaria spp., Diplodia spp., Epidermophyton spp., *Epidermophyton floccosum*, Exserophilum spp., Exophiala spp., Fonsecaea spp., Fulvia spp., Fusarium spp., Geotrichum spp., Guignardia spp., Helminthosporium spp., Histoplasma spp., Lecythophora spp., Macrophomina spp., Madurella spp., Magnaporthe spp., *Malassezia furfur*, Microsporum spp., Monilinia spp., Mucor spp., *Mycocentrospora acerina*, Nectria spp., Nocardia spp., Oospora spp., Ophiobolus spp., Paecilomyces spp., *Paracoccidioides brasiliensis*, Penicillium spp., *Phaeosclera dematioides*, Phaeoannellomyces spp., Phialemonium obovatum, Phialophora spp., Phylctaena spp., Phoma spp., Phomopsis spp., Phymatotrichum spp., Phytophthora spp., Pythium spp., *Piedraia hortai*, *Pneumocystis carinii*, Puccinia spp., *Pythium insidiosum*, *Rhinocladiella aquaspersa, Rhizomucor pusillus*, Rhizoctonia spp., Rhizopus spp., Saccharomyces spp., *Saksenaea vasiformis, Sarcinomyces phaeomuriformis*, Scerotium spp., Sclerotinia spp., Sphaerotheca spp., *Sporothrix schenckii, Syncephalastrum racemosum, Taeniolella boppii*, Taphrina spp., Thielaviopsis spp., Torulopsosis spp., Trichophyton spp., Trichosporon spp., *Ulocladium chartarum*, Ustilago spp., Venturia spp., Verticillium spp., *Wangiella dermatitidis*, Whetxelinia spp., and Xylohypha spp.

11. The method of claim 1, wherein said microcidal compound is a toxic compound or is a compound that causes a toxic compound to be produced in said microorganism that forms following fusion.

12. The method of claim 11, wherein said toxic compound is a toxin or fragment thereof selected from the group consisting of: diphtheria toxin, diphtheria toxin F2 fragment, diphtheria toxin A domain, Pseudomonas exotoxin A, and the A domain of Pseudomonas exotoxin A.

13. The method of claim 11, wherein said microcidal compound is a biosynthetic enzyme that causes a toxic compound to be produced in said microorganism that forms following fusion.

* * * * *